United States Patent
Engel et al.

[11] Patent Number: 6,083,879
[45] Date of Patent: Jul. 4, 2000

[54] HERBICIDAL BENZOYLISOTHIAZOLES

[75] Inventors: Stefan Engel, Idstein; Wolfgang von Deyn, Neustadt; Regina Luise Hill, Speyer; Uwe Kardorff, Mannheim; Martina Otten, Ludwigshafen; Peter Plath, Frankenthal; Marcus Vossen, Mannheim; Ulf Misslitz, Neustadt; Helmut Walter, Obrigheim; Karl-Otto Westphalen, Speyer, all of Germany

[73] Assignee: BASF Aktiengesellschaft, Germany

[21] Appl. No.: 09/171,196

[22] PCT Filed: Apr. 14, 1997

[86] PCT No.: PCT/EP97/01854

§ 371 Date: Oct. 15, 1998

§ 102(e) Date: Oct. 15, 1998

[87] PCT Pub. No.: WO97/38987

PCT Pub. Date: Oct. 23, 1997

[30] Foreign Application Priority Data

Apr. 16, 1996 [DE] Germany ............... 196 14 859

[51] Int. Cl.[7] ............... A01N 43/80; C07D 275/02; C07D 275/03
[52] U.S. Cl. ............... 504/269; 548/214; 548/213
[58] Field of Search ............... 548/214, 213; 504/269

[56] References Cited

U.S. PATENT DOCUMENTS

| | | | |
|---|---|---|---|
| 4,187,099 | 2/1980 | Franz et al. | 71/90 |
| 5,201,932 | 4/1993 | Maywald et al. | 504/271 |
| 5,338,857 | 8/1994 | Ohto et al. | 548/248 |

FOREIGN PATENT DOCUMENTS

| | | |
|---|---|---|
| 418 175 | 3/1991 | European Pat. Off. . |
| 449 223 | 10/1991 | European Pat. Off. . |
| 524 781 | 1/1993 | European Pat. Off. . |
| 527 036 | 2/1993 | European Pat. Off. . |
| 527 037 | 2/1993 | European Pat. Off. . |
| 560 482 | 9/1993 | European Pat. Off. . |
| 580 439 | 1/1994 | European Pat. Off. . |
| 588 357 | 3/1994 | European Pat. Off. . |
| 609 797 | 8/1994 | European Pat. Off. . |
| 609 798 | 8/1994 | European Pat. Off. . |
| 617 010 | 9/1994 | European Pat. Off. . |
| 636 622 | 2/1995 | European Pat. Off. . |
| 2-091076 | 3/1990 | Japan . |
| 2 284 600 | 6/1995 | United Kingdom . |
| 94/14782 | 7/1994 | WIPO . |
| 94/18179 | 8/1994 | WIPO . |
| 95/15691 | 6/1995 | WIPO . |
| 95/16678 | 6/1995 | WIPO . |
| 95/22903 | 8/1995 | WIPO . |
| 95/22904 | 8/1995 | WIPO . |
| 95/25105 | 9/1995 | WIPO . |

OTHER PUBLICATIONS

Rajappa et al., CA 71:30395, 1969.
Arya et al., CA 90:72098, 1979.
Machon et al., CA 110:231498, 1989.
Matsubara et al., CA 115:114491, 1991.
Chem. Abs. vol. 102, No. 13, Apr. 1, 1985, Abst. No. 113477d, S. 713.
Jrl. of Heterocyclic Chem., Bd. 25, No. 1, Jan. 1988, S 235–240.

*Primary Examiner*—Laura L. Stockton
*Attorney, Agent, or Firm*—Keil & Weinkauf

[57] ABSTRACT

4-Benzoylisothiazoles of the formula 1

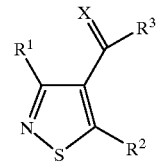

wherein
x is oxygen or sulfur;
$R^1$ is hydrogen, alkyl, alkenyl, alkynyl; or is optionally substituted alkoxycarbonyl, aryl, heterocyclyl or hetaryl;
$R^2$ is hydrogen, halogen, cyano, nitro, alkylsulfonyl or alkoxycarbonyl; or is optionally substituted alkyl, alkenyl, alkynyl, cycloalkyl, cycloalkenyl, aryl, aryloxy, arylthio, alkylamino, arylamino, hetaryl or heterocyclyl;
$R^3$ is optionally substituted alkyl, cycloalkyl or aryl, or their salts, their manufacture and herbicidal compositions containing them.

23 Claims, No Drawings

HERBICIDAL BENZOYLISOTHIAZOLES

This application is a 371 of PCT/EP97/01854 filed Apr. 14, 1997.

DESCRIPTION

The present invention relates to novel substituted benzoylisothiazoles, processes for their preparation, and their use as herbicides.

The patent literature (EP 0 527 036, EP 0 527 037, EP 0 560 482, EP 0 580 439, EP 0 588 357, EP 609 797, EP 0 609 798, EP 0 636 622, WO 94/14782, WO 94/18179, WO 95/15691 and WO 95/16678) discloses substituted 4-benzoyl-5-cycloalkylisoxazoles as a class of compounds which have a pronounced herbicidal activity pre-emergence. 4-(2-Sulfonylmethyl-4-trifluoromethylbenzoyl)-5-cyclopropyl-isoxazole, a representative of this class of compound, is developed by Rhône-Poulenc as a herbicidally active substance used pre-emergence against harmful mono- and dicotyledons in maize (RPA 201772, Technical Bulletin).

Moreover, the herbicidal and insecticidal activity of substituted 4-alkyl- and 4-cycloalkyl-5-aryl- or -5-hetarylisoxazoles has been disclosed (GB 2 284 600, WO 95/22903, WO 95/22904 and WO 95/25105).

The herbicidal activity of the known compounds is not only insufficiently effective post-emergence, but also only partly satisfactory pre-emergence and combined with incomplete crop plant compatibility.

Herbicidal or insecticidal 4-benzoylisothiazoles according to the invention have not been found in the prior art as yet.

As yet, 4-benzoylisothiazoles have only been of moderate interest with a view to their synthesis. While substituted isothiazoles and their carbocycle-fused derivatives have been the object of basic investigations (for example: D. L. Pain, B. J. Peart, K. R. H. Wooldridge, Comprehensive Heterocyclic Chemistry, Vol. 6, Part 4B, p. 131, Ed. A. R. Katritzky, Pergamon Press, Oxford 1984), only individual cases of acylated and, in particular, benzoylated derivatives have been described in the literature (for example: A. J. Layton, E. Lunt, J. Chem. Soc. (1968) 611, A. Alberola, F. Alonso, P. Cuadrado, C. M. Sanudo, Synth. Commun. 17 (1987) 1207, A. Alberola, F. Alonso, P. Cuadrado, C. M. Sanudo, J. Heterocycl. Chem. 25 (1988) 235).

Some hydroxypropylaminocarbonyl-substituted 4-benzoylisothiazoles have been investigated in EP 0 524 781 and EP 0 617 010 as muscle-relaxing agents and as suitable therapeutic amides to treat incontinence. EP 0 449 223 maintains that 3,5-di(tertiary-butyl)-4-hydroxybenzoylisothiazoles are inhibitors of 5-lipoxygenase and cyclooxygenase and thus have an anti-inflammatory action.

It is an object of the present invention to provide novel herbicidally active ingredients with an improved profile of action and improved crop plant compatibility.

Surprisingly, the benzoylisothiazoles of the general formula 1 according to the invention show a pronounced herbicidal activity against harmful plants combined with crop plant compatibility.

The present invention relates to 4-benzoylisothiazoles of the general formula 1

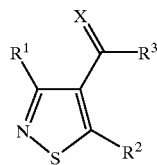

where the substituents have the following meanings:

X is oxygen or sulfur;

$R^1$ is hydrogen, alkyl, alkenyl, alkynyl; unsubstituted or substituted alkoxycarbonyl; unsubstituted or substituted aryl, unsubstituted or substituted heterocyclyl or unsubstituted or substituted hetaryl;

$R^2$ is hydrogen, alkyl, alkenyl, alkynyl, cycloalkyl or cycloalkenyl, it being possible for these radicals to have attached to them one or more of the following groups: halogen, alkyl, alkenyl or alkynyl; aryl, it being possible for this radical to have attached to it one or more of the following groups: alkyl, alkenyl, alkynyl, alkoxy, alkenyloxy, alkynyloxy, alkylthio or alkenylthio, it being possible for these radicals to be partially or fully halogenated or to have attached to them one or more of the following groups:

alkoxy, alkenyloxy, aryloxy, alkylsulfonyl, alkenylsulfonyl or arylsulfonyl;

alkylsulfonyl or alkoxycarbonyl;

unsubstituted or substituted aryloxy or unsubstituted or substituted arylthio;

unsubstituted or substituted mono- or dialkylamino, unsubstituted or substituted mono- or diarylamino or unsubstituted or substituted N-alkyl-N-arylamino, it being possible for alkyl and aryl to be identical or different;

halogen, cyano or nitro;

hetaryl or heterocyclyl, it being possible for these radicals to be partially or fully halogenated or to have attached to them one or more of the following groups:

alkyl, alkoxy or aryl, it being possible in the case of heterocyclyl for at least one of the nitrogens to have attached to it one of the following groups:

alkyl, alkenyl, alkynyl, cycloalkyl, haloalkyl, alkoxy, alkenyloxy, alkynyloxy, cycloalkyloxy, haloalkoxy, unsubstituted or substituted aryl or unsubstituted or substituted aryloxy;

$R^3$ is alkyl or cycloalkyl, it being possible for these radicals to be partially or fully halogenated or to have attached to them one or more of the following groups:

alkyl, alkenyl, alkynyl, alkoxy, alkenyloxy, alkynyloxy, alkylthio, alkenylthio, alkynylthio, alkoxycarbonyl, alkenyloxycarbonyl, alkynyloxycarbonyl, haloalkyl, haloalkenyl, haloalkynyl, haloalkoxy, haloalkenyloxy, haloalkynyloxy, haloalkylthio, haloalkenylthio, haloalkynylthio, haloalkoxycarbonyl, haloalkenyloxycarbonyl or haloalkynyloxycarbonyl;

a radical of the general formula 2

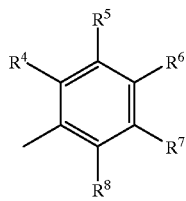

2 where the substituents have the following meanings:
$R^4$–$R^8$ can be identical or different and independently of one another are hydrogen, alkyl, alkenyl, alkynyl, cycloalkyl, cycloalkenyl, cycloalkylalkyl, cycloalkylalkenyl, cycloalkylalkynyl, aryl, arylalkyl, arylalkenyl, arylalkynyl, hydroxyl, alkoxy, alkenyloxy, alkynyloxy, cycloalkoxy, cycloalkylalkoxy, cycloalkylalkenyloxy, cycloalkylalkynyloxy, cycloalkenyloxy, aryloxy, arylalkoxy, arylalkenyloxy, arylalkynyloxy, thio, alkylthio, alkenylthio, alkynylthio, cycloalkylthio, cycloalkylalkylthio, cycloalkylalkenylthio, cycloalkylalkynylthio, cycloalkenylthio, arylthio, arylalkylthio, arylalkenylthio, arylalkynylthio, amino, unsubstituted or substituted mono- or dialkylamino, unsubstituted or substituted mono- or diarylamino, unsubstituted or substituted N-alkyl-N-arylamino, it being possible for alkyl and aryl to be identical or different, alkenylamino, alkynylamino, cycloalkylamino, cycloalkenylamino, sulfonyl, alkylsulfonyl, alkenylsulfonyl, alkynylsulfonyl, cycloalkylsulfonyl, cycloalkylalkylsulfonyl, cycloalkylalkenylsulfonyl, cycloalkylalkynylsulfonyl, arylsulfonyl, arylalkylsulfonyl, arylalkenylsulfonyl, arylalkynylsulfonyl, sulfoxyl, alkylsulfoxyl, alkenylsulfoxyl, alkynylsulfoxyl, cycloalkylsulfoxyl, cycloalkylalkylsulfoxyl, cycloalkylalkenylsulfoxyl, cycloalkylalkynylsulfoxyl, arylsulfoxyl, arylalkylsulfoxyl, arylalkenylsulfoxyl, arylalkynylsulfoxyl, unsubstituted or substituted mono- or dialkylaminosulfonyl, unsubstituted or substituted mono- or diarylaminosulfonyl, unsubstituted or substituted N-alkyl-N-arylaminosulfonyl, it being possible for alkyl and aryl to be identical or different, alkylcarbonyl, alkenylcarbonyl, alkynylcarbonyl, cycloalkylcarbonyl, cycloalkylalkylcarbonyl, cycloalkylalkenylcarbonyl, cycloalkylalkynylcarbonyl, arylcarbonyl, arylalkylcarbonyl, arylalkenylcarbonyl, arylalkynylcarbonyl, carboxyl, alkoxycarbonyl, alkenyloxycarbonyl, alkynyloxycarbonyl, cycloalkoxycarbonyl, cycloalkylalkoxycarbonyl, cycloalkylalkenyloxycarbonyl, cycloalkylalkynyloxycarbonyl, aryloxycarbonyl, arylalkoxycarbonyl, arylalkenyloxycarbonyl, arylalkynyloxycarbonyl, aminocarbonyl, unsubstituted or substituted mono- or dialkylaminocarbonyl, unsubstituted or substituted mono- or diarylaminocarbonyl, unsubstituted or substituted N-alkyl-N-arylaminocarbonyl, it being possible for alkyl and aryl to be identical or different, unsubstituted or substituted mono- or dialkylcarbonylamino, unsubstituted or substituted mono- or diarylcarbonylamino, unsubstituted or substituted N-alkyl-N-arylcarbonylamino, it being possible for alkyl and aryl to be identical or different, alkoxyaminocarbonyl, alkenyloxycarbonylamino, alkynyloxycarbonylamino, cycloalkoxycarbonylamino, cycloalkylalkoxycarbonylamino, cycloalkylalkenyloxycarbonylamino, cycloalkylalkynyloxycarbonylamino, aryloxycarbonylamino, arylalkoxycarbonylamino, arylalkenyloxycarbonylamino, arylalkynyloxycarbonylamino, halogen, haloalkyl, haloalkenyl, haloalkynyl, haloalkoxy, haloalkenyloxy, haloalkynyloxy haloalkylthio, haloalkenylthio, haloalkynylthio, haloalkylamino, haloalkenylamino, haloalkynylamino, haloalkylsulfonyl, haloalkenylsulfonyl, haloalkynylsulfonyl, haloalkylsulfoxyl, haloalkenylsulfoxyl, haloalkynylsulfoxyl, haloalkylcarbonyl, haloalkenylcarbonyl, haloalkynylcarbonyl, haloalkoxycarbonyl, haloalkenyloxycarbonyl, haloalkynyloxycarbonyl, haloalkylaminocarbonyl, haloalkenylaminocarbonyl, haloalkynylaminocarbonyl, haloalkoxycarbonylamino, haloalkenyloxycarbonylamino, haloalkynyloxycarbonylamino; cyano or nitro or one of the following groups:

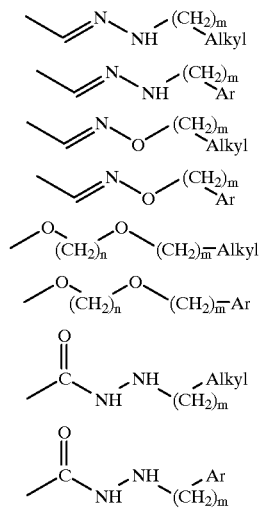

$n = 1, 2, 3; m = 0, 1, 2, 3$ with the exception of 4-(4'-chlorobenzoyl)-3-methylisothiazole, 4-benzoyl-3,5-dimethylisothiazole, 4-(4'-hydroxymethylcarbonylaminobenzoyl)isothiazole and 4-(3',5'-di-tertiary-butyl-4'-hydroxybenzoyl) isothiazole;

$R^4$, $R^5$ together can form a five- or six-membered, saturated or unsaturated, aromatic or non-aromatic, unsubstituted or substituted alkylene, alkenylene or alkdienylene chain;

$R^5$, $R^6$ together can form a five- or six-membered, saturated or unsaturated, aromatic or non-aromatic, unsubstituted or substituted alkylene, alkenylene or alkdienylene chain;

and to salts of the 4-benzoylisothiazoles of the general formula 1 which are conventionally used in agriculture.

In the definitions of the compounds I given at the outset, collective terms were used which generally represent the following groups:

halogen: fluorine, chlorine, bromine and iodine;

alkyl: straight-chain or branched alkyl groups having 1 to 6 or 10 carbon atoms, for example $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

alkylamino: an amino group which has attached to it a straight-chain or branched alkyl group having 1 to 6 carbon atoms as mentioned above;

dialkylamino: an amino group which has attached to it two mutually independent straight-chain or branched alkyl groups having in each case 1 to 6 carbon atoms as mentioned above;

alkylcarbonyl: straight-chain or branched alkyl groups having 1 to 10 carbon atoms which are bonded to the skeleton via a carbonyl group (—CO—);

alkylsulfonyl: straight-chain or branched alkyl groups having 1 to 6 or 10 carbon atoms which are bonded to the skeleton via a sulfonyl group (—SO$_2$—);

alkylsulfoxyl: straight-chain or branched alkyl groups having 1 to 6 carbon atoms which are bonded to the skeleton via a sulfoxyl group (—S(=O)—);

alkylaminocarbonyl: alkylamino groups having 1 to 6 carbon atoms as mentioned above which are bonded to the skeleton via a carbonyl group (—CO—);

dialkylaminocarbonyl: dialkylamino groups having in each case 1 to 6 carbon atoms per alkyl radical as mentioned above which are bonded to the skeleton via a carbonyl group (—CO—);

alkylaminothiocarbonyl: alkylamino groups having 1 to 6 carbon atoms as mentioned above which are bonded to the skeleton via a thiocarbonyl group (—CS—);

dialkylaminothiocarbonyl: dialkylamino groups having in each case 1 to 6 carbon atoms per alkyl radical as mentioned above which are bonded to the skeleton via a thiocarbonyl group (—CS—);

haloalkyl: straight-chain or branched alkyl groups having 1 to 6 carbon atoms, it being possible for some or all of the hydrogen atoms in these groups to be replaced by halogen atoms as mentioned above, eg. $C_1$–$C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkoxy: straight-chain or branched alkyl groups having 1 to 6 carbon atoms as mentioned above which are bonded to the skeleton via an oxygen atom (—O—), eg. $C_1$–$C_6$-alkoxy, such as methyloxy, ethyloxy, propyloxy, 1-methylethyloxy, butyloxy, 1-methyl-propyloxy, 2-methylpropyloxy, 1,1-dimethylethyloxy, pentyloxy, 1-methylbutyloxy, 2-methylbutyloxy, 3-methylbutyloxy, 2,2-dimethylpropyloxy, 1-ethylpropyloxy, hexyloxy, 1,1-dimethylpropyloxy, 1,2-dimethylpropyloxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropyloxy, 1,2,2-trimethylpropyloxy, 1-ethyl-1-methylpropyloxy and 1-ethyl-2-methylpropyloxy;

alkoxycarbonyl: straight-chain or branched alkyl groups having 1 to 6 carbon atoms which are bonded to the skeleton via an oxycarbonyl group (—OC(=O)—);

haloalkoxy: straight-chain or branched alkyl groups having 1 to 6 carbon atoms, it being possible for some or all of the hydrogen atoms in these groups to be replaced by halogen atoms as mentioned above, and these groups being bonded to the skeleton via an oxygen atom;

alkylthio: straight-chain or branched alkyl groups having 1 to 4 or 6 carbon atoms as mentioned above which are bonded to the skeleton via a sulfur atom (—S—), eg. $C_1$–$C_6$-alkylthio, such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

cycloalkyl: monocyclic alkyl groups having 3 to 6 carbon ring members, eg. cyclopropyl, cyclobutyl, cyclopentyl and cyclohexyl;

alkenyl: straight-chain or branched alkenyl groups having 2 to 6 or 10 carbon atoms and a double bond in any position, eg. $C_2$–$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

akenyloxy: straight-chain or branched alkenyl groups having 2 to 6 carbon atoms and a double bond in any position which are bonded to the skeleton via an oxygen atom (—O—);

alkenylthio and alkenylamino: straight-chain or branched alkenyl groups having 2 to 6 carbon atoms and a double bond in any position which are bonded to the skeleton via a sulfur atom (alkenylthio) or via a nitrogen atom (alkenylamino).

alkenylcarbonyl: straight-chain or branched alkenyl groups having 2 to 10 carbon atoms and a double bond in any position which are bonded to the skeleton via a carbonyl group (—CO—);

alkynyl: straight-chain or branched alkynyl groups having 2 to 10 carbon atoms and a triple bond in any position, eg. $C_2$–$C_6$-alkynyl, such as ethynyl, 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

alkynyloxy, alkynylthio and alkynylamino: straight-chain or branched alkynyl groups having 2 to 6 carbon atoms and a triple bond in any position which are bonded to the skeleton via an oxygen atom (alkynyloxy), via a sulfur atom (alkynylthio) or via a nitrogen atom (alkynylamino).

Alkynylcarbonyl: straight-chain or branched alkynyl groups having 3 to 10 carbon atoms and a triple bond in any position which are bonded to the skeleton via a carbonyl group (—CO—);

cycloalkenyl; cycloalkenyloxy, cycloalkenylthio and cycloalkenylamino: monocyclic alkenyl groups having 3 to 6 carbon ring members which are bonded to the skeleton directly; or via an oxygen atom (cycloalkenyloxy) or via a sulfur atom (cycloalkenylthio) or via a nitrogen atom (cycloalkenylamino), eg. cyclopropenyl, cyclobutenyl, cyclopentenyl or cyclohexenyl;

cycloalkoxy, cycloalkylthio and cycloalkylamino: monocyclic alkyl groups having 3 to 6 carbon ring members which are bonded to the skeleton via an oxygen atom (cycloalkyloxy), via a sulfur atom (cycloalkylthio) or via a nitrogen atom (cycloalkylamino), eg. cyclopropyl, cyclobutyl, cyclopentyl or cyclohexyl;

cycloalkylcarbonyl: cycloalkyl groups as defined above which are bonded to the skeleton via a carbonyl group (—CO—);

cycloalkoxycarbonyl: cycloalkoxy groups as defined above which are bonded to the skeleton via a carbonyl group (—CO—);

alkenyloxycarbonyl: alkenyloxy groups as defined above which are bonded to the skeleton via a carbonyl group (—CO—);

alkynyloxycarbonyl: alkynyloxy groups as defined above which are bonded to the skeleton via a carbonyl group (—CO—);

heterocyclyl: three- to six-membered saturated or partially unsaturated mono- or polycyclic heterocycles which contain one to three hetero atoms selected from a group consisting of oxygen, nitrogen and sulfur and which are bonded to the skeleton directly via carbon, eg. 2-tetrahydrofuranyl, oxiranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,3-dihydro-fur-4-yl, 2,3-dihydro-fur-5-yl, 2,5-dihydro-fur-2-yl, 2,5-dihydro-fur-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisothiazol-3-yl, 2,5-dihydroisothiazol-4-yl, 2,5-dihydroisothiazol-5-yl, 2,3-dihydroisopyrazol-3-yl, 2,3-dihydroisopyrazol-4-yl, 2,3-dihydroisopyrazol-5-yl, 4,5-dihydroisopyrazol-3-yl, 4,5-dihydroisopyrazol-4-yl, 4,5-dihydroisopyrazol-5-yl, 2,5-dihydroisopyrazol-3-yl, 2,5-dihydroisopyrazol-4-yl, 2,5-dihydroisopyrazol-5-yl, 2,3-dihydrooxazol-3-yl, 2,3-dihydrooxazol-4-yl, 2,3-dihydrooxazol-5-yl, 4,5-dihydrooxazol-3-yl, 4,5-dihydrooxazol-4-yl, 4,5-dihydrooxazol-5-yl, 2,5-dihydrooxazol-3-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2-morpholinyl, 3-morpholinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, 2-tetrahydropyranyl, 1,3-dioxolan-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl, 1,3-dithian-2-yl, aryl: aryloxy, arylthio, arylcarbonyl, aryloxycarbonyl, arylsulfonyl and arylsulfoxyl: aromatic mono- or polycyclic hydrocarbon radicals which are bonded to the skeleton directly; or (aryloxy) via an oxygen atom (—O—), or (arylthio) via a sulfur atom (—S—), or (arylcarbonyl) via a carbonyl group (—CO—), or (aryloxycarbonyl) via an oxycarbonyl group (—OCO—), or (arylsulfonyl) via a sulfonyl group (—$SO_2$—) or (arylsulfoxyl) via a sulfoxyl group (—SO—), eg. phenyl, naphthyl and phenanthrenyl; phenyloxy, naphthyloxy and phenanthrenyloxy and the corresponding carbonyl and sulfonyl radicals;

arylamino: aromatic mono- or polycyclic hydrocarbon radicals which are bonded to the skeleton via a nitrogen atom.

Hetaryl: aromatic mono- or polycyclic radicals which, besides carbon ring members, additionally contain one to four nitrogen atoms or one to three nitrogen atoms and an oxygen or a sulfur atom or an oxygen or a sulfur atom and which are bonded to the skeleton directly via carbon, eg.

5-membered hetaryl containing one to three nitrogen atoms: 5-membered hetaryl ring groups which, besides carbon atoms, can contain one to three nitrogen atoms as ring members, eg. 2-pyrrolyl, 3-pyrrolyl, 3-pyrazolyl, 4-pyrazolyl, 5-pyrazolyl, 2-imidazolyl, 4-imidazolyl, 1,2,4-triazol-3-yl and 1,3,4-triazol-2-yl;

5-membered hetaryl containing one to four nitrogen atoms or one to three nitrogen atoms and a sulfur or oxygen atom or an oxygen or a sulfur atom: 5-membered hetaryl ring groups which, besides carbon atoms, can contain one to four nitrogen atoms or one to three nitrogen atoms and a sulfur or oxygen atom or an oxygen or sulfur atom as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl;

carbocycle-fused 5-membered hetaryl containing one to three nitrogen atoms or a nitrogen atom and/or an oxygen or sulfur atom: 5-membered hetaryl ring groups which, besides carbon atoms, can contain one to four nitrogen atoms or one to three nitrogen atoms and a sulfur or oxygen atom or an oxygen or a sulfur atom as ring members and in which two adjacent carbon ring members or a nitrogen and an adjacent carbon ring member can be bridged by a buta-1,3-diene-1,4-diyl group;

6-membered hetaryl containing one to three, or one to four. nitrogen atoms: 6-membered hetaryl ring groups which, besides carbon atoms, can contain one to three, or one to four, nitrogen atoms as ring members, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzo-fused 6-membered hetaryl containing one to four nitrogen atoms: 6-membered hetaryl ring groups in which two adjacent carbon ring members can be bridged by a buta-1,3-diene-1,4-diyl group, eg. quinoline, isoquinoline, quinazoline and quinoxaline, and the corresponding oxy, thio, carbonyl or sulfonyl groups.

The term "partially or fully halogenated" expresses that in groups thus characterized some or all of the hydrogen atoms can be replaced by identical or different halogen atoms as mentioned above.

Unsubstituted or substituted means that the organic group in question can be substituted as desired, all substituents listed in the present application being suitable in principle.

Preferred substituents are hydrogen, alkyl, alkenyl, alkynyl, preferably cycloalkyl, cycloalkylalkyl, cycloalkylalkenyl, aryl, arylalkyl, arylalkenyl, hydroxyl, alkoxy, alkenyloxy, cycloalkoxy, cycloalkylalkoxy, aryloxy, arylalkoxy, thio, alkylthio, alkenylthio, cycloalkylthio, cycloalkylalkylthio, arylthio, arylalkylthio, amino, unsubstituted or substituted mono- or dialkylamino, unsubstituted or substituted mono- or diarylamino, unsubstituted or substituted N-alkyl-N-arylamino, it being possible for alkyl and aryl to be identical or different, alkenylamino, cycloalkylamino, cycloalkenylamino, sulfonyl, alkylsulfonyl, alkenylsulfonyl, cycloalkylsulfonyl, cycloalkylalkylsulfonyl, arylsulfonyl, arylalkylsulfonyl, sulfoxyl, alkylsulfoxyl, alkenylsulfoxyl, cycloalkylsulfoxyl, cycloalkylalkylsulfoxyl, arylsulfoxyl, arylalkylsulfoxyl, alkylcarbonyl, alkenylcarbonyl, cycloalkylcarbonyl, cycloalkylalkylcarbonyl, arylcarbonyl, arylalkylcarbonyl, carboxyl, alkoxycarbonyl, alkenyloxycarbonyl, cycloalkoxycarbonyl, cycloalkylalkoxycarbonyl, aryloxycarbonyl, arylalkoxycarbonyl, aminocarbonyl, unsubstituted or substituted mono- or dialkylaminocarbonyl, unsubstituted or substituted mono- or diarylaminocarbonyl, unsubstituted or substituted N-alkyl-N-arylaminocarbonyl, it being possible for alkyl and aryl to be identical or different, alkoxyaminocarbonyl, alkenyloxycarbonylamino, cycloalkoxycarbonylamino, aryloxycarbonylamino, arylalkoxycarbonylamino, halogen, haloalkyl, haloalkenyl, unsubstituted or substituted mono- or dialkylamino, haloalkoxy, haloalkenyloxy, haloalkylthio, haloalkenylthio, haloalkylamino, haloalkenylamino, haloalkylsulfonyl, haloalkenylsulfonyl, haloalkylsulfoxyl, haloalkenylsulfoxyl, haloalkylcarbonyl, haloalkenylcarbonyl, haloalkoxycarbonyl, haloalkenyloxycarbonyl, haloalkylaminocarbonyl, haloalkenylaminocarbonyl, haloalkoxycarbonylamino, haloalkenyloxycarbonylamino, cyano or nitro.

Especially preferred substituents are hydrogen, alkyl, alkenyl, cycloalkyl, cycloalkylalkyl, aryl, arylalkyl, hydroxyl, alkoxy, cycloalkoxy, aryloxy, thio, alkylthio, cycloalkylthio, arylthio, amino, unsubstituted or substituted mono- or dialkylamino, unsubstituted or substituted mono- or diarylamino, unsubstituted or substituted N-alkyl-N-arylamino, it being possible for alkyl and aryl to be identical or different, cycloalkylamino, sulfonyl, alkylsulfonyl, cycloalkylsulfonyl, arylsulfonyl, sulfoxyl, alkylsulfoxyl, arylsulfoxyl, alkylcarbonyl, arylcarbonyl, carboxyl, alkoxycarbonyl, aryloxycarbonyl, aminocarbonyl, unsubstituted or substituted mono- or dialkylaminocarbonyl, unsubstituted or substituted mono- or diarylaminocarbonyl, unsubstituted or substituted N-alkyl-N-arylaminocarbonyl, it being possible for alkyl and aryl to be identical or different, alkoxyaminocarbonyl, aryloxycarbonylamino, halogen, haloalkyl, haloalkoxy, haloalkylthio, haloalkylamino, haloalkylsulfonyl, haloalkylsulfoxyl, haloalkylcarbonyl, haloalkoxycarbonyl, haloalkoxycarbonylamino, cyano or nitro.

Preferred compounds of the general formula 1 with a view to their biological activity are those where X is oxygen.

Furthermore, preferred compounds of the general formula 1 are those where $R^1$ is hydrogen or unsubstituted or substituted alkoxycarbonyl.

Also preferred compounds of the general formula 1 are those where $R^1$ is hydrogen or alkoxycarbonyl having 1 to 6 carbon atoms which can be mono- or polysubstituted by fluorine, chlorine or bromine.

Especially preferred compounds of the formula 1 are those where $R^1$ is hydrogen, methoxycarbonyl or ethoxycarbonyl.

Furthermore, preferred compounds of the general formula 1 are those where $R^2$ is alkyl having 1 to 6 carbon atoms, especially preferably methyl, ethyl, isopropyl or tertiary butyl; or cycloalkyl having 3 to 6 carbon atoms, especially preferably cyclopropyl or 1-methylcyclopropyl; or aryl, it being possible for this radical to have attached to it one or more of the following groups:

alkyl, alkoxy, alkylthio, it being possible for these radicals to be partially or fully halogenated, or halogen, especially preferably 3-trifluoromethylaryl, 2,4-difluoroaryl; hetaryl or heterocyclyl, it being possible for these radicals to be partially or fully halogenated or to have attached to them one or more of the following groups: alkyl, alkoxy or aryl, especially preferably 1,3-benzodioxol, 2,2-difluoro-1,3-benzodioxol, 1,3-benzoxathiol, 3,3-dioxo-1,3-benzoxathiol, benzoxazole, pyrazolyl or thienyl.

Furthermore, preferred compounds of the general formula 1 are those where $R^3$ is a radical of the general formula 2

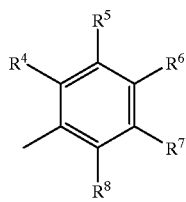

where the substituents have the following meanings:

$R^4$–$R^8$ can be identical or different and independently of one another are hydrogen, alkyl, cycloalkyl, aryl, hydroxyl, alkoxy, cycloalkoxy, aryloxy, thio, alkylthio, cycloalkylthio, arylthio, amino, in each case unsubstituted or substituted mono- or dialkylamino or mono- or diarylamino or N-alkyl-N-arylamino, it being possible for alkyl and aryl to be identical or different, cycloalkylamino, sulfonyl, alkylsulfonyl, cycloalkylsulfonyl, arylsulfonyl, sulfoxyl, alkylsulfoxyl, cycloalkylsulfoxyl, arylsulfoxyl, alkylcarbonyl, cycloalkylcarbonyl, arylcarbonyl, carboxyl, alkoxycarbonyl, cycloalkoxycarbonyl, aryloxycarbonyl, aminocarbonyl, in each case unsubstituted or substituted mono- or dialkylaminocarbonyl or mono- or diarylaminocarbonyl or N-alkyl-N-arylaminocarbonyl, it being possible for alkyl and aryl to be identical or different, alkoxyaminocarbonyl, cycloalkoxycarbonylamino, aryloxycarbonylamino, halogen, haloalkyl, haloalkoxy, haloalkylthio, haloalkylamino, haloalkylsulfonyl, haloalkylsulfoxyl, haloalkylcarbonyl, haloalkoxycarbonyl, haloalkylaminocarbonyl, haloalkoxycarbonylamino; cyano or nitro;

$R^4$, $R^5$ together can form a five- or six-membered, saturated or unsaturated, aromatic or non-aromatic, unsubstituted or substituted alkylene, alkenylene or alkdienylene chain;

$R^5$, $R^6$ together can form a five- or six-membered, saturated or unsaturated, aromatic or non-aromatic, unsubstituted or substituted alkylene, alkenylene or alkdienylene chain.

Other preferred compounds of the general formula 1 are those where $R^3$ is a radical of the general formula 2a–g

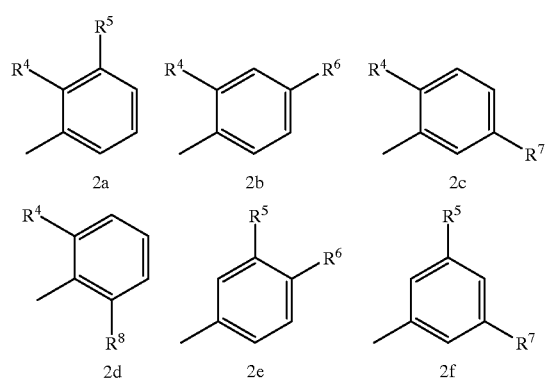

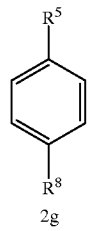

where the substituents have the following meanings:
$R^4$–$R^8$ can be identical or different and independently of one another are alkyl, alkenyl, alkynyl, cycloalkyl, cycloalkylalkyl, cycloalkylalkenyl, cycloalkylalkynyl, aryl, arylalkyl, arylalkenyl, arylalkynyl, hydroxyl, alkoxy, alkenyloxy, alkynyloxy, cycloalkoxy, cycloalkylalkoxy, cycloalkylalkenyloxy, cycloalkylalkynyloxy, aryloxy, arylalkoxy, arylalkenyloxy, arylalkynyloxy, thio, alkylthio, alkenylthio, alkynylthio, cycloalkylthio, cycloalkylalkylthio, cycloalkylalkenylthio, cycloalkylalkynylthio, arylthio, arylalkylthio, arylalkenylthio, arylalkynylthio, amino, unsubstituted or substituted mono- or dialkylamino, unsubstituted or substituted mono- or diarylamino, unsubstituted or substituted N-alkyl-N-arylamino, it being possible for alkyl and aryl to be identical or different, sulfonyl, alkylsulfonyl, cycloalkylsulfonyl, cycloalkylalkylsulfonyl, cycloalkylalkenylsulfonyl, cycloalkylalkynylsulfonyl, arylsulfonyl, arylalkylsulfonyl, arylalkenylsulfonyl, arylalkynylsulfonyl, sulfoxyl, alkylsulfoxyl, alkenylsulfoxyl, alkynylsulfoxyl, cycloalkylsulfoxyl, cycloalkylalkylsulfoxyl, cycloalkylalkenylsulfoxyl, cycloalkylalkynylsulfoxyl, arylsulfoxyl, arylalkylsulfoxyl, arylalkenylsulfoxyl, arylalkynylsulfoxyl, aminosulfonyl, unsubstituted or substituted mono- or dialkylaminosulfonyl, unsubstituted or substituted mono- or diarylaminosulfonyl, unsubstituted or substituted N-alkyl-N-arylaminosulfonyl, it being possible for alkyl and aryl to be identical or different, alkylcarbonyl, alkenylcarbonyl, alkynylcarbonyl, cycloalkylcarbonyl, cycloalkylalkylcarbonyl, cycloalkylalkenylcarbonyl, cycloalkylalkynylcarbonyl, arylcarbonyl, arylalkylcarbonyl, arylalkenylcarbonyl, arylalkynylcarbonyl, carboxyl, alkoxycarbonyl, alkenyloxycarbonyl, alkynyloxycarbonyl, cycloalkoxycarbonyl, cycloalkylalkoxycarbonyl, cycloalkylalkenyloxycarbonyl, cycloalkylalkynyloxycarbonyl, arylcarbonyl, arylalkoxycarbonyl, arylalkenyloxycarbonyl, arylalkynyloxycarbonyl, aminocarbonyl, unsubstituted or substituted mono- or dialkylaminocarbonyl, unsubstituted or substituted mono- or diarylaminocarbonyl, unsubstituted or substituted N-alkyl-N-arylaminocarbonyl, it being possible for alkyl and aryl to be identical or different, unsubstituted or substituted mono- or dialkylcarbonylamino, unsubstituted or substituted mono- or diarylcarbonylamino, unsubstituted or substituted N-alkyl-N-arylcarbonylamino, it being possible for alkyl and aryl to be identical or different, alkoxyaminocarbonyl, alkenyloxycarbonylamino, alkynyloxycarbonylamino, cycloalkoxycarbonylamino, cycloalkylalkoxycarbonylamino, cycloalkylalkenyloxycarbonylamino, cycloalkylalkynyloxycarbonylamino, aryloxycarbonylamino, arylalkoxycarbonylamino, arylalkenyloxycarbonylamino, arylalkynyloxycarbonylamino, halogen, haloalkyl, haloalkenyl, haloalkynyl, haloalkoxy, haloalkenyloxy, haloalkynyloxy, haloalkylthio, haloalkenylthio, haloalkynylthio, haloalkylamino, haloalkenylamino, haloalkynylamino, haloalkylsulfonyl, haloalkenylsulfonyl, haloalkynylsulfonyl, haloalkylcarbonyl, haloalkenylcarbonyl, haloalkynylcarbonyl, haloalkoxycarbonyl, haloalkenyloxycarbonyl, haloalkynyloxycarbonyl, haloalkylaminocarbonyl, haloalkenylaminocarbonyl, haloalkynylaminocarbonyl, haloalkoxycarbonylamino, haloalkenyloxycarbonylamino, haloalkynyloxycarbonylamino; cyano or nitro.

Furthermore, preferred compounds of the general formula 1 are those where $R^3$ is a radical of the general formula 2h–l

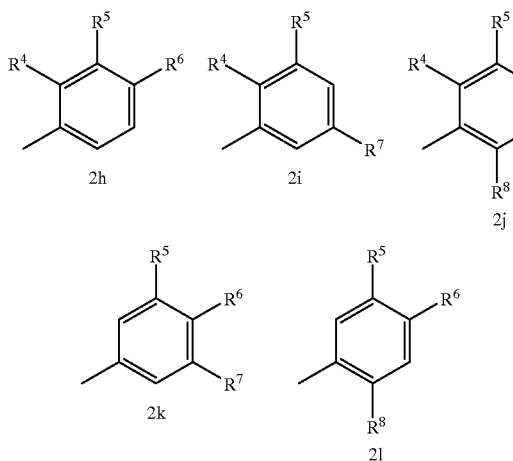

where the substituents have the following meanings:

$R^4$–$R^8$ can be identical or different and independently of one another are a low-molecular radical selected from the group consisting of alkyl, alkenyl, alkynyl, cycloalkyl, cycloalkylalkyl, cycloalkylalkenyl, cycloalkylalkynyl, aryl, arylalkyl, arylalkenyl, arylalkynyl, hydroxyl, alkoxy, alkenyloxy, alkynyloxy, cycloalkoxy, cycloalkylalkoxy, cycloalkylalkenyloxy, cycloalkylalkynyloxy, aryloxy, arylalkoxy, arylalkenyloxy, arylalkynyloxy, thio, alkylthio, alkenylthio, alkynylthio, cycloalkylthio, cycloalkylalkylthio, cycloalkylalkenylthio, cycloalkylalkynylthio, arylthio, arylalkylthio, arylalkenylthio, arylalkynylthio, amino, unsubstituted or substituted mono- or dialkylamino, unsubstituted or substituted mono- or diarylamino, unsubstituted or substituted N-alkyl-N-arylamino, it being possible for alkyl and aryl to be identical or different, sulfonyl, alkylsulfonyl, cycloalkylsulfonyl, cycloalkylalkylsulfonyl, cycloalkylalkenylsulfonyl, cycloalkylalkynylsulfonyl, arylsulfonyl, arylalkylsulfonyl, arylalkenylsulfonyl, arylalkynylsulfonyl, sulfoxyl, alkylsulfoxyl, alkenylsulfoxyl, alkynylsulfoxyl, cycloalkylsulfoxyl, cycloalkylalkylsulfoxyl, cycloalkylalkenylsulfoxyl, cycloalkylalkynylsulfoxyl, arylsulfoxyl, arylalkylsulfoxyl, arylalkenylsulfoxyl, arylalkynylsulfoxyl, aminosulfonyl, unsubstituted or substituted mono- or dialkylaminosulfonyl, unsubstituted or substituted mono- or diarylaminosulfonyl, unsubstituted or substituted N-alkyl-N-arylaminosulfonyl, it being possible for alkyl and aryl to be identical or different, alkylcarbonyl, alkenylcarbonyl, alkynylcarbonyl, cycloalkylcarbonyl, cycloalkylalkylcarbonyl, cycloalkylalkenylcarbonyl, cycloalkylalkynylcarbonyl, arylcarbonyl, arylalkylcarbonyl, arylalkenylcarbonyl, arylalkynylcarbonyl, carboxyl, alkoxycarbonyl, alkenyloxycarbonyl, alkynyloxycarbonyl, cycloalkoxycarbonyl, cycloalkylalkoxycarbonyl, cycloalkylalkenyloxycarbonyl, cycloalkylalkynyloxycarbonyl, arylcarbonyl, arylalkoxycarbonyl, arylalkenyloxycarbonyl, arylalkynyloxycarbonyl, aminocarbonyl, unsubstituted or substituted mono- or dialkylaminocarbonyl, unsubstituted or substituted mono- or diarylaminocarbonyl, unsubstituted or substituted N-alkyl-N-arylaminocarbonyl, it being possible for alkyl and aryl to be identical or different, unsubstituted or substituted mono- or dialkylcarbonylamino, unsubstituted or substituted mono- or diarylcarbonylamino, unsubstituted or substituted N-alkyl-N-arylcarbonylamino, it being possible for alkyl and aryl to be identical or different, alkoxyaminocarbonyl, alkenyloxycarbonylamino, alkynyloxycarbonylamino, cycloalkoxycarbonylamino, cycloalkylalkoxycarbonylamino, cycloalkylalkenyloxycarbonylamino, cycloalkylalkynyloxycarbonylamino, aryloxycarbonylamino, arylalkoxycarbonylamino, arylalkenyloxycarbonylamino, arylalkynyloxycarbonylamino, halogen, haloalkyl, haloalkenyl, haloalkynyl, haloalkoxy, haloalkenyloxy, haloalkynyloxy, haloalkylthio, haloalkenylthio, haloalkynylthio, haloalkylamino, haloalkenylamino, haloalkynylamino, haloalkylsulfonyl, haloalkenylsulfonyl, haloalkynylsulfonyl, haloalkylcarbonyl, haloalkenylcarbonyl, haloalkynylcarbonyl, haloalkoxycarbonyl, haloalkenyloxycarbonyl, haloalkynyloxycarbonyl, haloalkylaminocarbonyl, haloalkenylaminocarbonyl, haloalkynylaminocarbonyl, haloalkoxycarbonylamino, haloalkenyloxycarbonylamino, haloalkynyloxycarbonylamino; hydroxy, cyano or nitro, $R^4$, $R^5$ together can form a five- or six-membered, saturated or unsaturated, aromatic or non-aromatic, unsubstituted or mono- or polysubstituted alkylene, alkenylene or alkdienylene chain;

$R^5$, $R^6$ together can form a five- or six-membered, saturated or unsaturated, aromatic or non-aromatic, unsubstituted or mono- or polysubstituted alkylene, alkenylene or alkdienylene chain.

Moreover, preferred compounds of the general formula 1 are those where $R^3$ is a radical of the general formula 2,

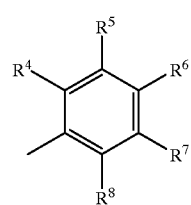

or a radical of the general formula 2a–g

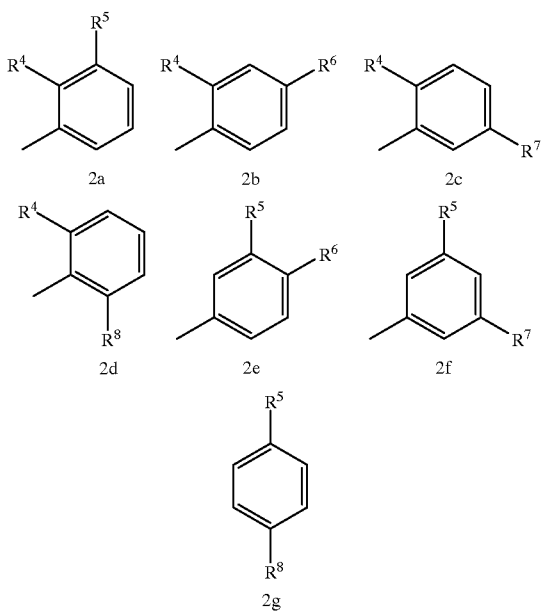

or 2h–l

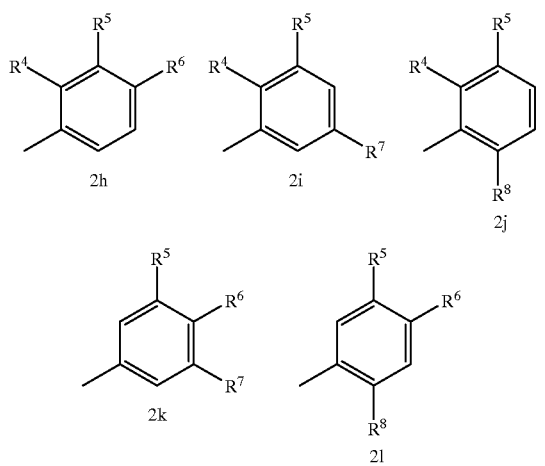

where the substituents have the following meanings:
R$^4$–R$^8$ can be identical or different and independently of one another are hydrogen, C$_1$–C$_6$-alkyl, preferably methyl, ethyl, propyl, 1-methylethyl, butyl, 2-methylpropyl, pentyl or hexyl; C$_2$–C$_6$-alkenyl, preferably ethenyl, 2-propenyl, 2-butenyl or 3-butenyl; C$_2$–C$_6$-alkynyl, preferably ethynyl, 2-propynyl, 2-butynyl or 3-butynyl; C$_3$–C$_6$-cycloalkyl, preferably cyclopropyl, cyclobutyl, cyclopentyl or cyclohexyl, C$_3$–C$_6$-cycloalkyl-C$_1$–C$_6$-alkyl, C$_3$–C$_6$-cycloalkyl-C$_2$–C$_6$-alkenyl, C$_3$–C$_6$-cycloalkyl-C$_2$–C$_6$-alkynyl, aryl, preferably phenyl or naphthyl, aryl-C$_1$–C$_6$-alkyl, aryl-C$_2$–C$_6$-alkenyl, aryl-C$_2$–C$_6$-alkynyl; hydroxyl, C$_1$–C$_6$-alkoxy, preferably methyloxy, ethyloxy, propyloxy, 1-methylethyloxy, butyloxy, pentyloxy or hexyloxy, C$_2$–C$_6$-alkenyloxy, preferably ethenyloxy, 2-propenyloxy, 2-butenyloxy or 3-butenyloxy; C$_2$–C$_6$-alkynyloxy, preferably ethynyloxy, 2-propynyloxy, 2-butynyloxy or 3-butynyloxy; C$_3$–C$_6$-cycloalkoxy, preferably cyclopropyloxy, cyclobutyloxy, cyclopentyloxy or cyclohexyloxy, C$_3$–C$_6$-cycloalkyl-C$_1$–C$_6$-alkoxy, C$_3$–C$_6$-cycloalkyl-C$_2$–C$_6$-alkynyloxy; aryloxy, preferably phenoxy or naphthyloxy, aryl-C$_1$–C$_6$-alkoxy, aryl-C$_2$–C$_6$-alkenyloxy, aryl-C$_2$–C$_6$-alkynyloxy; thio; C$_1$–C$_6$-alkylthio, preferably methylthio, ethylthio, propylthio, 1-methylethylthio, butylthio, pentylthio or hexylthio; C$_2$–C$_6$-alkenylthio, preferably ethenylthio, 2-propenylthio, 2-butenylthio or 3-butenylthio; C$_2$–C$_6$-alkynylthio, preferably ethynylthio, 2-propynylthio, 2-butynylthio or 3-butynylthio; C$_3$–C$_6$-cycloalkylthio, preferably cyclopropylthio, cyclobutylthio, cyclopentylthio or cyclohexylthio, C$_3$–C$_6$-cycloalkyl-C$_1$–C$_6$-alkylthio, C$_3$–C$_6$-cycloalkyl-C$_2$–C$_6$-alkenylthio, C$_3$–C$_6$-cycloalkyl-C$_2$–C$_6$-alkynylthio; arylthio, preferably phenylthio or naphthylthio, aryl-C$_1$–C$_6$-alkylthio, aryl-C$_2$–C$_6$-alkenylthio, aryl-C$_2$–C$_6$-alkynylthio; amino, unsubstituted or substituted mono- or di-C$_1$–C$_6$-alkylamino, unsubstituted or substituted mono- or diarylamino, unsubstituted or substituted N-C$_1$–C$_6$-alkyl-N-arylamino, it being possible for alkyl and aryl to be identical or different; sulfonyl; C$_1$–C$_6$-alkylsulfonyl, preferably methylsulfonyl, ethylsulfonyl, propylsulfonyl, 1-methylethylsulfonyl, butylsulfonyl, 2-methylpropylsulfonyl, pentylsulfonyl or hexylsulfonyl; C$_3$–C$_6$-cycloalkylsulfonyl, preferably cyclopropylsulfonyl, cyclobutylsulfonyl, cyclopentylsulfonyl or cyclohexylsulfonyl, C$_3$–C$_6$-cycloalkyl-C$_1$–C$_6$-alkylsulfonyl, C$_3$–C$_6$-cycloalkyl-C$_2$–C$_6$-alkenylsulfonyl, C$_3$–C$_6$-cycloalkyl-C$_2$–C$_6$-alkynylsulfonyl; arylsulfonyl, preferably phenylsulfonyl or naphthylsulfonyl, aryl-C$_1$–C$_6$-alkylsulfonyl, aryl-C$_2$–C$_6$-alkenylsulfonyl, aryl-C$_2$–C$_6$-alkynylsulfonyl; sulfoxyl, C$_1$–C$_6$-alkylsulfoxyl, C$_2$–C$_6$-alkenylsulfoxyl, C$_2$–C$_6$-alkynylsulfoxyl, C$_3$–C$_8$-cycloalkylsulfoxyl, C$_3$–C$_8$-cycloalkyl-C$_1$–C$_6$-alkylsulfoxyl, C$_3$–C$_8$-cycloalkyl-C$_2$–C$_6$-alkenylsulfoxyl, C$_3$–C$_8$-cycloalkyl-C$_2$–C$_6$-alkynylsulfoxyl, arylsulfoxyl, aryl-C$_1$–C$_6$-alkylsulfoxyl, aryl-C$_2$–C$_6$-alkenylsulfoxyl, aryl-C$_2$–C$_6$-alkynylsulfoxyl, aminosulfonyl, unsubstituted or substituted mono- or di-C$_1$–C$_6$-alkylaminosulfonyl, unsubstituted or substituted mono- or diarylaminosulfonyl, unsubstituted or substituted N-C$_1$–C$_6$-alkyl-N-arylaminosulfonyl, it being possible for alkyl and aryl to be identical or different, C$_1$–C$_6$-alkylcarbonyl, preferably methylcarbonyl, ethylcarbonyl, propylcarbonyl, 1-methylethylcarbonyl, butylcarbonyl, 2-methylpropylcarbonyl, pentylcarbonyl or hexylcarbonyl; C$_2$–C$_6$-alkenylcarbonyl, preferably ethenylcarbonyl, 2-propenylcarbonyl, 2-butenylcarbonyl or 3-butenylcarbonyl; C$_2$–C$_6$-alkynylcarbonyl, preferably ethynylcarbonyl, 2-propynylcarbonyl, 2-butynylcarbonyl or 3-butynylcarbonyl; C$_3$–C$_6$-cycloalkylcarbonyl, preferably cyclopropylcarbonyl, cyclobutylcarbonyl, cyclopentylcarbonyl or cyclohexylcarbonyl, C$_3$–C$_6$-cycloalkyl-C$_1$–C$_6$-alkylcarbonyl, C$_3$–C$_6$-cycloalkyl-C$_2$–C$_6$-alkenylcarbonyl, C$_3$–C$_6$-cycloalkyl-C$_2$–C$_6$-alkynylcarbonyl; arylcarbonyl, preferably phenylcarbonyl or naphthylcarbonyl, aryl-C$_1$–C$_6$-alkylcarbonyl, aryl-C$_2$–C$_6$-alkenylcarbonyl, aryl-C$_2$–C$_6$-alkynylcarbonyl; carboxyl; C$_1$–C$_6$-alkoxycarbonyl, methyloxycarbonyl, ethyloxycarbonyl, propyloxycarbonyl, 1-methylethyloxycarbonyl, butyloxycarbonyl, pentyloxycarbonyl or hexyloxycarbonyl, C$_2$–C$_6$-Alkenyloxycarbonyl, C$_2$–C$_6$-alkynyloxycarbonyl, C$_3$–C$_6$-cycloalkoxycarbonyl, cyclopropyloxycarbonyl, cyclobutyloxycarbonyl, cyclopentyloxycarbonyl or cyclohexyloxycarbonyl, C$_3$–C$_6$-cycloalkyl-C$_1$–C$_6$-alkoxycarbonyl, C$_3$–C$_6$-cycloalkyl-C$_2$–C$_6$-alkenyloxycarbonyl, C$_3$–C$_6$-cycloalkyl-C$_2$–C$_6$- alkynyloxycarbonyl; aryloxycarbonyl, preferably phenyloxycarbonyl or naphthyloxycarbonyl, aryl-$C_1$–$C_6$-alkoxycarbonyl, aryl-$C_2$–$C_6$-alkenyloxycarbonyl, aryl-$C_2$–$C_6$-alkynyloxycarbonyl; aminocarbonyl; unsubstituted or substituted mono- or di-$C_1$-$C_6$-alkylaminocarbonyl, unsubstituted or substituted mono- or diarylaminocarbonyl, unsubstituted or substituted N-$C_1$–$C_6$-alkyl-N-arylaminocarbonyl, it being possible for alkyl and aryl to be identical or different, unsubstituted or substituted mono- or di-$C_1$–$C_6$-alkylcarbonylamino, unsubstituted or substituted mono- or diarylcarbonylamino, unsubstituted or substituted N-$C_1$-$C_6$-alkyl-N-arylcarbonylamino, it being possible for alkyl and aryl to be identical or different, $C_1$–$C_6$-alkoxyaminocarbonyl, preferably methyloxyaminocarbonyl, ethyloxyaminocarbonyl, propyloxyaminocarbonyl, 1-methylethyloxyaminocarbonyl, butyloxyaminocarbonyl, 2-methylpropyloxyaminocarbonyl, pentyloxyaminocarbonyl or hexyloxyaminocarbonyl; $C_2$–$C_6$-alkenyloxycarbonylamino, preferably ethyleneoxyaminocarbonyl, 2-propenyloxyaminocarbonyl, 2-butenyloxyaminocarbonyl or 3-butenyloxyaminocarbonyl; $C_2$–$C_6$-alkynyloxycarbonylamino, preferably ethynyloxyaminocarbonyl, 2-propynyloxyaminocarbonyl, 2-butynyloxyaminocarbonyl or 3-butynyloxyaminocarbonyl; $C_3$–$C_6$-cycloalkoxyaminocarbonyl, preferably cyclopropyloxyaminocarbonyl, cyclobutyloxyaminocarbonyl, cyclopentyloxyaminocarbonyl or cyclohexyloxyaminocarbonyl, $C_3$–$C_6$-cycloalkyl-$C_1$–$C_6$-alkoxyaminocarbonyl, $C_3$–$C_6$-cycloalkyl-$C_2$–$C_6$-alkenyloxyaminocarbonyl, $C_3$–$C_6$-cycloalkyl-$C_1$–$C_6$-alkynyloxyaminocarbonyl; aryloxyaminocarbonyl, preferably phenyloxyaminocarbonyl or naphthyloxyaminocarbonyl, aryl-$C_1$–$C_6$-alkoxyaminocarbonylamino, aryl-$C_2$–$C_6$-alkenyloxyaminocarbonyl, aryl-$C_2$–$C_6$-alkynyloxyaminocarbonyl; halogen, preferably fluorine, chlorine, bromine or iodine; $C_1$–$C_6$-haloalkyl, preferably chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, $C_2$–$C_6$-haloalkenyl, $C_2$–$C_6$-haloalkynyl; $C_1$–$C_6$-haloalkoxy, preferably chloromethyl, dichloromethyl, trichloromethyl, fluoromethyloxy, difluoromethyloxy, trifluoromethyloxy, chlorofluoromethyloxy, dichlorofluoromethyloxy, chlorodifluoromethyloxy, 1-fluoroethyloxy, 2-fluoroethyloxy, 2,2-difluoroe-hyloxy, 2,2,2-trifluoroethyloxy, 2-chloro-2-fluoroethyloxy, 2-chloro-2,2-difluoroethyloxy, 2,2-dichloro-2-fluoroethyloxy, 2,2,2-trichloroethyloxy or pentafluoroethyloxy, $C_2$–$C_6$-haloalkenyloxy, $C_2$–$C_6$-haloalkynyloxy; $C_1$–$C_6$-haloalkylthio, preferably chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, $C_2$–$C_6$-haloalkenylthio, $C_2$–$C_6$-haloalkynylthio; $C_1$–$C_6$-haloalkylamino, preferably chloromethylamino, dichloromethylamino, trichloromethylamino, fluoromethylamino, difluoromethylamino, trifluoromethylamino, chlorofluoromethylamino, dichlorofluoromethylamino, chlorodifluoromethylamino, 1-fluoroethylamino, 2-fluoroethylamino, 2,2-difluoroethylamino, 2,2,2-trifluoroethylamino, 2-chloro-2-fluoroethyl-amino, 2-chloro-2,2-difluoroethylamino, 2,2-dichloro-2-fluoroethylamino, 2,2,2-trichloroethylamino or pentafluoroethylamino, $C_2$–$C_6$-haloalkenylamino, $C_2$–$C_6$-haloalkynylamino, $C_1$–$C_6$-haloalkylsulfonyl, preferably chloromethylsulfonyl, dichloromethylsulfonyl, trichloromethylsulfonyl, fluoromethylsulfonyl, difluoromethylsulfonyl, trifluoromethylsulfonyl, chlorofluoromethylsulfonyl, dichlorofluoromethylsulfonyl, chlorodifluoromethylsulfonyl, 1-fluoroethylsulfonyl, 2-fluoroethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl or pentafluoroethylsulfonyl, $C_2$–$C_6$-haloalkenylsulfonyl, $C_2$–$C_6$-haloalkynylsulfonyl; $C_1$–$C_6$-haloalkylcarbonyl, preferably chloromethylcarbonyl, dichloromethylcarbonyl, trichloromethylcarbonyl, fluoromethylcarbonyl, difluoromethylcarbonyl, trifluoromethylcarbonyl, chlorofluoromethylcarbonyl, dichlorofluoromethylcarbonyl, chlorodifluoromethylcarbonyl, 1-fluoroethylcarbonyl, 2-fluoroethylcarbonyl, 2,2-difluoroethylcarbonyl, 2,2,2-trifluoroethylcarbonyl, 2-chloro-2-fluoro-ethylcarbonyl, 2-chloro-2,2-difluoroethylcarbonyl, 2,2-dichloro-2-fluoro-ethylcarbonyl, 2-2-2-trichloroethylcarbonyl or pentafluoroethylcarbonyl, $C_2$–$C_6$-haloalkenylcarbonyl, $C_2$–$C_6$-haloalkynylcarbonyl; $C_1$–$C_6$-haloalkoxycarbonyl, preferably chloromethyloxycarbonyl, dichloromethyloxycarbonyl, trichloromethyloxycarbonyl, fluoromethyloxycarbonyl, difluoromethyloxycarbonyl, trifluoromethyloxycarbonyl, chlorofluoromethyloxycarbonyl, dichlorofluoromethyloxycarbonyl, chlorodifluoromethyloxycarbonyl, 1-fluoroethyloxycarbonyl, 2-fluoroethyloxycarbonyl, 2,2-difluoroethyloxycarbonyl, 2,2,2-trifluoroethyloxycarbonyl, 2-chloro-2-fluoroethyloxycarbonyl, 2-chloro-2,2-difluoroethyloxycarbonyl, 2,2-dichloro-2-fluoroethyloxycarbonyl, 2,2,2-trichloroethyloxycarbonyl or pentafluoroethyloxycarbonyl, $C_2$–$C_6$-haloalkenyloxycarbonyl, $C_2$–$C_6$-haloalkynyloxycarbonyl; $C_1$-$C_6$-haloalkylaminocarbonyl, preferably chloromethylaminocarbonyl, dichloromethylaminocarbonyl, trichloromethylaminocarbonyl, fluoromethylaminocarbonyl, difluoromethylaminocarbonyl, trifluoromethylaminocarbonyl, chlorofluoromethylaminocarbonyl, dichlorofluoromethylaminocarbonyl, chlorodlfluoromethylaminocarbonyl, 1-fluoroethylaminocarbonyl, 2-fluoroethylaminocarbonyl, 2,2-difluoroethylaminocarbonyl, 2,2,2- trifluoroethylaminocarbonyl, 2-chloro-2-fluoroethylaminocarbonyl, 2-chloro-2,2-difluoroethylaminocarbonyl, 2,2-dichloro-2-fluoroethylaminocarbonyl, 2,2,2-trichloroethylaminocarbonyl or pentafluoroethylaminocarbonyl, $C_2$-$C_6$-haloalkenylaminocarbonyl, $C_2$-$C_6$-haloalkynylaminocarbonyl; $C_1$-$C_6$-haloalkoxycarbonylamino, chloromethyloxyaminocarbonyl, dichloromethyloxycarbonyl, trichloromethyloxyaminocarbonyl, fluoromethyloxyaminocarbonyl, difluoromethyloxyaminocarbonyl, trifluoromethyloxyaminocarbonyl, chlorofluoromethyloxyaminocarbonyl, dichlorofluoromethyloxyaminocarbonyl, chlorodifluoromethyloxyaminocarbonyl, 1-fluoroethyloxyaminocarbonyl, 2-fluoroethyloxyaminocarbonyl, 2,2-difluoroethyloxyaminocarbonyl, 2,2,2-trifluoroethyloxyaminocarbonyl, 2-chloro-2-fluoroethyloxyaminocarbonyl, 2-chloro-2,2-difluoroethyloxyaminocarbonyl, 2,2-dichloro-2-fluoroethyloxyaminocarbonyl, 2,2,2-trichloroethyloxyaminocarbonyl or pentafluoroethyloxyaminocarbonyl, $C_2$-$C_6$-haloalkenyloxycarbonylamino, $C_2$-$C_6$-haloalkynyloxycarbonylamino; cyano or nitro.

Moreover, especially preferred compounds of the general formula 1 are those where $R^3$ is a radical of the general formula 2b

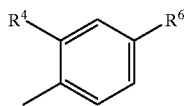

2b where $R^4$ and $R^6$ are identical or different and independently of one another are alkyl, preferably methyl or ethyl, alkylsulfonyl, preferably methylsulfonyl or ethylsulfonyl; halogen, preferably fluorine, chlorine or bromine, or haloalkyl, preferably difluoromethyl, trifluoromethyl, tetrafluoroethyl or trichloromethyl.

Also preferred compounds of the general formula 1 are those where $R^3$ is a radical of the general formula 2h

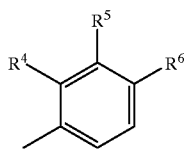

2h where $R^4$, $R^5$ and $R^6$ are identical or different and independently of one another are alkyl, preferably methyl or ethyl, alkoxy, preferably methoxy, ethoxy or aryloxy; alkylsulfonyl, preferably methylsulfonyl or ethylsulfonyl; halogen, preferably fluorine, chlorine, bromine or iodine; haloalkyl, preferably difluoromethyl, trifluoromethyl, tetrafluoroethyl or trichloromethyl.

Also preferred compounds of the general formula 1 are those where $R^3$ is 2-chloro-4-sulfonylmethylphenyl.

Furthermore, also preferred compounds of the general formula 1 are those where $R^3$ is 2-sulfonylmethyl-4-trifluoromethylphenyl.

Also preferred compounds of the general formula 1 are those where $R^3$ is 2-chloro-3-methoxy-4-sulfonylmethylphenyl or 2-chloro-3-ethoxy-4-sulfonylethylphenyl.

Also preferred compounds of the general formula 1 are those where the substituents are selected from a combination of the abovementioned preferred substituents.

4-Benzoylisothiazoles of the general formula 1 are obtainable a) by reacting the haloisothiazole compounds 3

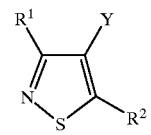

3 where $R^1$ and $R^2$ have the above-described meanings and Y is halogen, preferably chlorine, bromine or iodine, with elemental magnesium or an organomagnesium or organolithium compound and a carboxylic acid derivative of the general formula 4

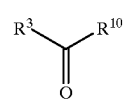

4 where $R^3$ has the above-described meanings and $R^{10}$ is halogen, preferably chlorine, bromine or iodine, or N-alkoxy-N-alkylamino, preferably N-methoxy-N-methylamino or cyano, at from −78° C. to 111° C., preferably at from −20° C. to 111° C., in the presence of an inert solvent (A. Alberola, F. Alonso, P. Cuadrado, M. C. Sanudo, Synth. Commun. 17 (1987)1207), or b. by reacting a halobenzene of the general formula 5

5 where $R^3$ has the above-described meanings and Y is halogen, preferably chlorine, bromine or iodine, with elemental magnesium or an organomagnesium or organolithium compound and an isothiazolecarboxylic acid derivative of the general formula 6a or 6b,

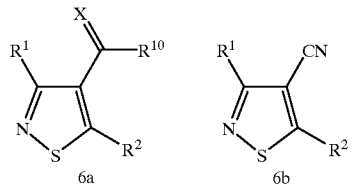

where X, $R^1$ and $R^2$ have the above-described meanings and $R^{10}$ is halogen, preferably chlorine, bromine or iodine, and N-alkoxy-N-alkylamino, preferably N-methoxy-N-methylamino, at from −78° C. to 111° C., preferably at from −20° C. to 111° C., in the presence of an inert solvent (A. Alberola, F. Alonso, P Cuadrado, M. C. Sanudo, J. Heterocyclic Chem. 25 (1988) 235).

The haloisothiazole compounds 3 are synthesized by halogenating isothiazole compounds of the general formula 7

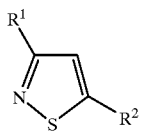

where $R^1$ and $R^2$ have the above-described meanings by processes known from the literature (of which may be mentioned as representatives: a. A. Alberola, F. Alonso, P. Cuadrado, M. C. Sanudo, Synth. Commun. 17 (1987)1207; b. Vasilevskii, Izv. Akad. Nauk. SSSR Ser. Khim. (1975) 616).

Isothiazole compounds of the general formula 7 are known and are synthesized following methods known from the literature (of which may be mentioned as representatives: a. D. N NcGregor. U. Corbin, J. E. Swigor, I. C. Cheney, Tetrahedron 25 (1968) 389; b. F. Lucchesini, N. Picci. M. Pocci. Heterocycles 29 (1989) 97).

The isothiazolecarboxylic acid derivatives of the general formula 6b are synthesized by reacting haloisothiazole compounds 3 with organic cyanides, for example copper(I) cyanide, by processes known from the literature (of which may be mentioned as representatives: A. Alberola, F. Alonso, P Cuadrado, M. C. Sanudo, J. Heterocyclic Chem. 25 (1988) 235). The corresponding isothiazolecarboxylic acid derivatives of the general formula 6a can be obtained by processes known from the literature starting from isothiazolecarboxylic acid derivatives of the general formula 6b.

Preferred organomagnesium compounds are alkylmagnesium halides, for example methyl- or ethylmagnesium bromide or methyl- or ethylmagnesium chloride. Preferred organolithium compounds which are suitable are aliphatic lithium compounds such as lithium diisopropylamide, n-butyllithium or secondary-butyllithium.

The choice of organic solvent depends on the starting materials employed. In general, all inert solvents are suitable. Preferred inert solvents are aliphatic, cyclic or acyclic ethers, eg. diethyl ether, tetrahydrofuran, dioxane or 1,2-dimethoxyethane. In addition, inert aromatic solvents such as benzene or toluene are also used.

The starting materials are normally reacted with each other in stoichiometric amounts. However, it may be advantageous to employ one of the starting materials in an excess of 0.1 to 10 mol equivalents, for example to improve the yield.

Examples of especially preferred compounds of the general formula 1 are compiled in the tables which follow. The definitions of the radicals are not only especially preferred in the specific combination of radicals, but also in each case by themselves.

TABLE 1

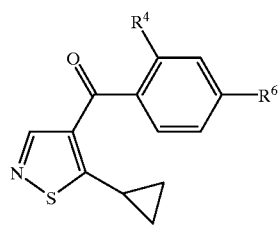

| No. | $R^4$ | $R^6$ |
|---|---|---|
| 7.1 | F | F |
| 7.2 | F | Cl |
| 7.3 | F | Br |
| 7.4 | F | $CH_3$ |
| 7.5 | F | $C_2H_5$ |
| 7.6 | F | $nC_3H_7$ |
| 7.7 | F | $iC_3H_7$ |
| 7.8 | F | $nC_4H_9$ |
| 7.9 | F | $tC_4H_9$ |
| 7.10 | F | Ph |
| 7.11 | F | OH |
| 7.12 | F | $OCH_3$ |
| 7.13 | F | $OC_2H_5$ |
| 7.14 | F | $O(nC_3H_7)$ |
| 7.15 | F | $O(iC_3H_7)$ |
| 7.16 | F | $O(nC_4H_9)$ |
| 7.17 | F | $O(tC_4H_9)$ |
| 7.18 | F | OPh |
| 7.19 | F | SH |
| 7.20 | F | $SCH_3$ |
| 7.21 | F | $SC_2H_5$ |
| 7.22 | F | $S(nC_3H_7)$ |
| 7.23 | F | $S(iC_3H_7)$ |
| 7.24 | F | $S(nC_4H_9)$ |
| 7.25 | F | $S(tC_4H_9)$ |
| 7.26 | F | SPh |
| 7.27 | F | $CCl_3$ |
| 7.28 | F | $CH_2F$ |
| 7.29 | F | $CHF_2$ |
| 7.30 | F | $CF_3$ |
| 7.31 | F | $CF_2CHF_2$ |
| 7.32 | F | $SO_3H$ |
| 7.33 | F | $SO_2CH_3$ |
| 7.34 | F | $SO_2C_2H_5$ |
| 7.35 | F | $SO_2(nC_3H_7)$ |
| 7.36 | F | $SO_2(iC_3H_7)$ |
| 7.37 | F | $SO_2(nC_4H_9)$ |
| 7.38 | F | $SO_2(tC_4H_9)$ |
| 7.39 | F | $SO_2Ph$ |
| 7.40 | F | $NH_2$ |
| 7.41 | F | $NHCH_3$ |
| 7.42 | F | $NCH_3Ph$ |
| 7.43 | F | $N(CH_3)2$ |
| 7.44 | F | $NPh_2$ |
| 7.45 | F | CN |
| 7.46 | F | $NO_2$ |
| 7.47 | Cl | F |
| 7.48 | Cl | Cl |
| 7.49 | Cl | Br |
| 7.50 | Cl | $CH_3$ |
| 7.51 | Cl | $C_2H_5$ |
| 7.53 | Cl | $nC_3H_7$ |
| 7.54 | Cl | $iC_3H_7$ |
| 7.55 | Cl | $nC_4H_9$ |
| 7.56 | Cl | $tC_4H_9$ |
| 7.57 | Cl | Ph |
| 7.58 | Cl | OH |
| 7.59 | Cl | $OCH_3$ |
| 7.60 | Cl | $OC_2H_5$ |
| 7.61 | Cl | $O(nC_3H_7)$ |
| 7.62 | Cl | $O(iC_3H_7)$ |
| 7.63 | Cl | $O(nC_4H_9)$ |
| 7.64 | Cl | $O(tC_4H_9)$ |
| 7.65 | Cl | OPh |

TABLE 1-continued

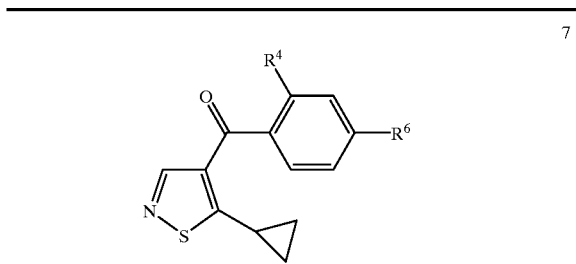

| No. | R⁴ | R⁶ |
|---|---|---|
| 7.66 | Cl | SH |
| 7.67 | Cl | SCH₃ |
| 7.68 | Cl | SC₂H₅ |
| 7.69 | Cl | S(nC₃H₇) |
| 7.70 | Cl | S(iC₃H₇) |
| 7.71 | Cl | S(nC₄H₉) |
| 7.72 | Cl | S(tC₄H₉) |
| 7.73 | Cl | SPh |
| 7.74 | Cl | CCl₃ |
| 7.75 | Cl | CH₂F |
| 7.76 | Cl | CHF₂ |
| 7.77 | Cl | CF₃ |
| 7.78 | Cl | CF₂CHF₂ |
| 7.79 | Cl | SO₃H |
| 7.80 | Cl | SO₂CH₃ |
| 7.81 | Cl | SO₂C₂H₅ |
| 7.82 | Cl | SO₂(nC₃H₇) |
| 7.83 | Cl | SO₂(iC₃H₇) |
| 7.84 | Cl | SO₂(nC₄H₉) |
| 7.85 | Cl | SO₂(tC₄H₉) |
| 7.86 | Cl | SO₂Ph |
| 7.87 | Cl | NH₂ |
| 7.88 | Cl | NHCH₃ |
| 7.89 | Cl | NCH₃Ph |
| 7.90 | Cl | N(CH₃)₂ |
| 7.91 | Cl | NPh₂ |
| 7.92 | Cl | CN |
| 7.93 | Cl | NO₂ |
| 7.94 | CH₃ | F |
| 7.95 | CH₃ | Cl |
| 7.98 | CH₃ | Br |
| 7.97 | CH₃ | CH₃ |
| 7.98 | CH₃ | C₂H₅ |
| 7.99 | CH₃ | nC₃H₇ |
| 7.100 | CH₃ | iC₃H₇ |
| 7.101 | CH₃ | nC₄H₉ |
| 7.102 | CH₃ | tC₄H₉ |
| 7.102 | CH₃ | Ph |
| 7.103 | CH₃ | OH |
| 7.104 | CH₃ | OCH₃ |
| 7.105 | CH₃ | OC₂H₅ |
| 7.106 | CH₃ | O(nC₃H₇) |
| 7.107 | CH₃ | O(iC₃H₇) |
| 7.108 | CH₃ | O(nC₄H₉) |
| 7.109 | CH₃ | O(tC₄H₉) |
| 7.110 | CH₃ | OPh |
| 7.111 | CH₃ | SH |
| 7.112 | CH₃ | SCH₃ |
| 7.113 | CH₃ | SC₂H₅ |
| 7.114 | CH₃ | S(nC₃H₇) |
| 7.115 | CH₃ | S(iC₃H₇) |
| 7.116 | CH₃ | S(nC₄H₉) |
| 7.117 | CH₃ | S(tC₄H₉) |
| 7.118 | CH₃ | SPh |
| 7.119 | CH₃ | CCl₃ |
| 7.120 | CH₃ | CH₂F |
| 7.121 | CH₃ | CHF₂ |
| 7.122 | CH₃ | CF₃ |
| 7.123 | CH₃ | CF₂CHF₂ |
| 7.124 | CH₃ | SO₃H |
| 7.125 | CH₃ | SO₂CH₃ |
| 7.126 | CH₃ | SO₂C₂H₅ |
| 7.127 | CH₃ | SO₂(nC₃H₇) |
| 7.128 | CH₃ | SO₂(iC₃H₇) |

TABLE 1-continued

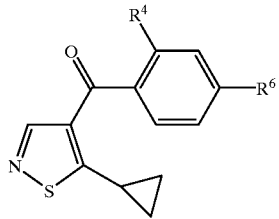

| No. | R⁴ | R⁶ |
|---|---|---|
| 7.129 | CH₃ | SO₂(nC₄H₉) |
| 7.130 | CH₃ | SO₂(tC₄H₉) |
| 7.131 | CH₃ | SO₂Ph |
| 7.132 | CH₃ | NH₂ |
| 7.133 | CH₃ | NHCH₃ |
| 7.134 | CH₃ | NCH₃Ph |
| 7.135 | CH₃ | N(CH₃)2 |
| 7.136 | CH₃ | NPh₂ |
| 7.137 | CH₃ | CN |
| 7.138 | CH₃ | NO₂ |
| 7.139 | CF₃ | F |
| 7.140 | CF₃ | Cl |
| 7.141 | CF₃ | Br |
| 7.142 | CF₃ | CH₃ |
| 7.143 | CF₃ | C₂H₅ |
| 7.144 | CF₃ | nC₃H₇ |
| 7.145 | CF₃ | iC₃H₇ |
| 7.146 | CF₃ | nC₄H₉ |
| 7.147 | CF₃ | tC₄H₉ |
| 7.148 | CF₃ | Ph |
| 7.149 | CF₃ | OH |
| 7.150 | CF₃ | OCH₃ |
| 7.151 | CF₃ | OC₂H₅ |
| 7.152 | CF₃ | O(nC₃H₇) |
| 7.153 | CF₃ | O(iC₃H₇) |
| 7.154 | CF₃ | O(nC₄H₉) |
| 7.155 | CF₃ | O(tC₄H₉) |
| 7.156 | CF₃ | OPh |
| 7.157 | CF₃ | SH |
| 7.158 | CF₃ | SCH₃ |
| 7.159 | CF₃ | SC₂H₅ |
| 7.160 | CF₃ | S(nC₃H₇) |
| 7.161 | CF₃ | S(iC₃H₇) |
| 7.162 | CF₃ | S(nC₄H₉) |
| 7.163 | CF₃ | S(tC₄H₉) |
| 7.164 | CF₃ | SPh |
| 7.165 | CF₃ | CCl₃ |
| 7.166 | CF₃ | CH₂F |
| 7.167 | CF₃ | CHF₂ |
| 7.168 | CF₃ | CF₃ |
| 7.169 | CF₃ | CF₂CHF₂ |
| 7.170 | CF₃ | SO₃H |
| 7.171 | CF₃ | SO₂CH₃ |
| 7.172 | CF₃ | SO₂C₂H₅ |
| 7.173 | CF₃ | SO₂(nC₃H₇) |
| 7.174 | CF₃ | SO₂(iC₃H₇) |
| 7.175 | CF₃ | SO₂(nC₄H₉) |
| 7.176 | CF₃ | SO₂(tC₄H₉) |
| 7.177 | CF₃ | SO₂Ph |
| 7.178 | CF₃ | NH₂ |
| 7.179 | CF₃ | NHCH₃ |
| 7.180 | CF₃ | NCH₃Ph |
| 7.181 | CF₃ | N(CH₃)₂ |
| 7.182 | CF₃ | NPh₂ |
| 7.183 | CF₃ | CN |
| 7.184 | CF₃ | NO₂ |
| 7.185 | SO₂CH₃ | F |
| 7.186 | SO₂CH₃ | Cl |
| 7.187 | SO₂CH₃ | Br |
| 7.188 | SO₂CH₃ | CH3 |
| 7.189 | SO₂CH₃ | C₂H₅ |
| 7.190 | SO₂CH₃ | nC₃H₇ |
| 7.191 | SO₂CH₃ | iC₃H₇ |
| 7.192 | SO₂CH₃ | nC₄H₉ |

TABLE 1-continued

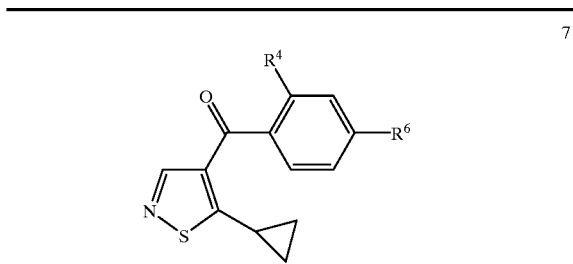

| No. | $R^4$ | $R^6$ |
|---|---|---|
| 7.193 | $SO_2CH_3$ | $tC_4H_9$ |
| 7.194 | $SO_2CH_3$ | Ph |
| 7.195 | $SO_2CH_3$ | OH |
| 7.196 | $SO_2CH_3$ | $OCH_3$ |
| 7.197 | $SO_2CH_3$ | $OC_2H_5$ |
| 7.198 | $SO_2CH_3$ | $O(nC_3H_7)$ |
| 7.199 | $SO_2CH_3$ | $O(iC_3H_7)$ |
| 7.200 | $SO_2CH_3$ | $O(nC_4H_9)$ |
| 7.201 | $SO_2CH_3$ | $O(tC_4H_9)$ |
| 7.202 | $SO_2CH_3$ | OPh |
| 7.203 | $SO_2CH_3$ | SH |
| 7.204 | $SO_2CH_3$ | $SCH_3$ |
| 7.205 | $SO_2CH_3$ | $SC_2H_5$ |
| 7.206 | $SO_2CH_3$ | $S(nC_3H_7)$ |
| 7.207 | $SO_2CH_3$ | $S(iC_3H_7)$ |
| 7.208 | $SO_2CH_3$ | $S(nC_4H_9)$ |
| 7.209 | $SO_2CH_3$ | $S(tC_4H_9)$ |
| 7.210 | $SO_2CH_3$ | SPh |
| 7.211 | $SO_2CH_3$ | $CCl_3$ |
| 7.212 | $SO_2CH_3$ | $CH_2F$ |
| 7.213 | $SO_2CH_3$ | $CHF_2$ |
| 7.214 | $SO_2CH_3$ | $CF_3$ |
| 7.215 | $SO_2CH_3$ | $CF_2CHF_2$ |
| 7.216 | $SO_2CH_3$ | $SO_3H$ |
| 7.217 | $SO_2CH_3$ | $SO_2CH_3$ |
| 7.218 | $SO_2CH_3$ | $SO_2C_2H_5$ |
| 7.219 | $SO_2CH_3$ | $SO_2(nC_3H_7)$ |
| 7.220 | $SO_2CH_3$ | $SO_2(iC_3H_7)$ |
| 7.221 | $SO_2CH_3$ | $SO_2(nC_4H_9)$ |
| 7.222 | $SO_2CH_3$ | $SO_2(tC_4H_9)$ |
| 7.223 | $SO_2CH_3$ | $SO_2Ph$ |
| 7.224 | $SO_2CH_3$ | $NH_2$ |
| 7.225 | $SO_2CH_3$ | $NHCH_3$ |
| 7.226 | $SO_2CH_3$ | $NCH_3Ph$ |
| 7.227 | $SO_2CH_3$ | $N(CH_3)_2$ |
| 7.228 | $SO_2CH_3$ | $NPh_2$ |
| 7.229 | $SO_2CH_3$ | CN |
| 7.230 | $SO_2CH_3$ | $NO_2$ |
| 7.231 | CN | F |
| 7.232 | CN | Cl |
| 7.233 | CN | Br |
| 7.234 | CN | $CH_3$ |
| 7.235 | CN | $C_2H_5$ |
| 7.236 | CN | $nC_3H_7$ |
| 7.237 | CN | $iC_3H_7$ |
| 7.238 | CN | $nC_4H_9$ |
| 7.239 | CN | $tC_4H_9$ |
| 7.240 | CN | Ph |
| 7.241 | CN | OH |
| 7.242 | CN | $OCH_3$ |
| 7.243 | CN | $OC_2H_5$ |
| 7.244 | CN | $O(nC_3H_7)$ |
| 7.245 | CN | $O(iC_3H_7)$ |
| 7.246 | CN | $O(nC_4H_9)$ |
| 7.247 | CN | $O(tC_4H_9)$ |
| 7.248 | CN | OPh |
| 7.249 | CN | SH |
| 7.250 | CN | $SCH_3$ |
| 7.251 | CN | $SC_2H_5$ |
| 7.252 | CN | $S(nC_3H_7)$ |
| 7.253 | CN | $S(iC_3H_7)$ |
| 7.254 | CN | $S(nC_4H_9)$ |
| 7.255 | CN | $S(tC_4H_9)$ |
| 7.256 | CN | SPh |

TABLE 1-continued

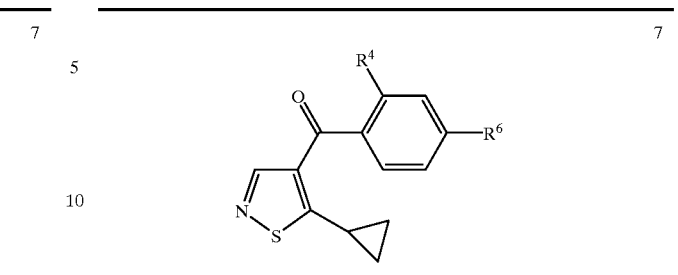

| No. | $R^4$ | $R^6$ |
|---|---|---|
| 7.257 | CN | $CCl_3$ |
| 7.258 | CN | $CH_2F$ |
| 7.259 | CN | $CHF_2$ |
| 7.260 | CN | $CF_3$ |
| 7.261 | CN | $CF_2CHF_2$ |
| 7.262 | CN | $SO_3H$ |
| 7.263 | CN | $SO_2CH_3$ |
| 7.264 | CN | $SO_2C_2H_5$ |
| 7.265 | CN | $SO_2(nC_3H_7)$ |
| 7.266 | CN | $SO_2(iC_3H_7)$ |
| 7.267 | CN | $SO_2(nC_4H_9)$ |
| 7.268 | CN | $SO_2(tC_4H_9)$ |
| 7.269 | CN | $SO_2Ph$ |
| 7.270 | CN | $NH_2$ |
| 7.271 | CN | $NHCH_3$ |
| 7.272 | CN | $NCH_3Ph$ |
| 7.273 | CN | $N(CH_3)_2$ |
| 7.274 | CN | $NPh_2$ |
| 7.275 | CN | CN |
| 7.276 | CN | $NO_2$ |

TABLE 2

| No. | $R^4$ | $R^5$ | $R^6$ |
|---|---|---|---|
| 8.1 | F | $OCH_3$ | F |
| 8.2 | F | $OCH_3$ | Cl |
| 8.3 | F | $OCH_3$ | Br |
| 8.4 | F | $OCH_3$ | $CH_3$ |
| 8.5 | F | $OCH_3$ | $C_2H_5$ |
| 8.6 | F | $OCH_3$ | $nC_3H_7$ |
| 8.7 | F | $OCH_3$ | $iC_3H_7$ |
| 8.8 | F | $OCH_3$ | $nC_4H_9$ |
| 8.9 | F | $OCH_3$ | $tC_4H_9$ |
| 8.10 | F | $OCH_3$ | Ph |
| 8.11 | F | $OCH_3$ | OH |
| 8.12 | F | $OCH_3$ | $OCH_3$ |
| 8.13 | F | $OCH_3$ | $OC_2H_5$ |
| 8.14 | F | $OCH_3$ | $O(nC_3H_7)$ |
| 8.15 | F | $OCH_3$ | $O(iC_3H_7)$ |
| 8.16 | F | $OCH_3$ | $O(nC_4H_9)$ |
| 8.17 | F | $OCH_3$ | $O(tC_4H_9)$ |
| 8.18 | F | $OCH_3$ | OPh |
| 8.19 | F | $OCH_3$ | SH |
| 8.20 | F | $OCH_3$ | $SCH_3$ |
| 8.21 | F | $OCH_3$ | $SC_2H_5$ |
| 8.22 | F | $OCH_3$ | $S(nC_3H_7)$ |
| 8.23 | F | $OCH_3$ | $S(iC_3H_7)$ |

TABLE 2-continued

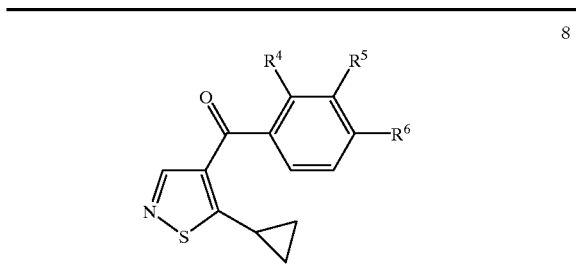

| No. | R⁴ | R⁵ | R⁶ |
|---|---|---|---|
| 8.24 | F | OCH₃ | S(nC₄H₉) |
| 8.25 | F | OCH₃ | S(tC₄H₉) |
| 8.26 | F | OCH₃ | SPh |
| 8.27 | F | OCH₃ | CCl₃ |
| 8.28 | F | OCH₃ | CH₂F |
| 8.29 | F | OCH₃ | CHF₂ |
| 8.30 | F | OCH₃ | CF₃ |
| 8.31 | F | OCH₃ | CF₂CHF₂ |
| 8.32 | F | OCH₃ | SO₃H |
| 8.33 | F | OCH₃ | SO₂CH₃ |
| 8.34 | F | OCH₃ | SO₂C₂H₅ |
| 8.35 | F | OCH₃ | SO₂(nC₃H₇) |
| 8.36 | F | OCH₃ | SO₂(iC₃H₇) |
| 8.37 | F | OCH₃ | SO₂(nC₄H₉) |
| 8.38 | F | OCH₃ | SO₂(tC₄H₉) |
| 8.39 | F | OCH₃ | SO₂Ph |
| 8.40 | F | OCH₃ | NH₂ |
| 8.41 | F | OCH₃ | NHCH₃ |
| 8.42 | F | OCH₃ | NCH₃Ph |
| 8.43 | F | OCH₃ | N(CH₃)₂ |
| 8.44 | F | OCH₃ | NPh₂ |
| 8.45 | F | OCH₃ | CN |
| 8.46 | F | OCH₃ | NO₂ |
| 8.47 | Cl | OCH₃ | F |
| 8.48 | Cl | OCH₃ | Cl |
| 8.49 | Cl | OCH₃ | Br |
| 8.50 | Cl | OCH₃ | CH₃ |
| 8.51 | Cl | OCH₃ | C₂H₅ |
| 8.53 | Cl | OCH₃ | nC₃H₇ |
| 8.54 | Cl | OCH₃ | iC₃H₇ |
| 8.55 | Cl | OCH₃ | nC₄H₉ |
| 8.56 | Cl | OCH₃ | tC₄H₉ |
| 8.57 | Cl | OCH₃ | Ph |
| 8.58 | Cl | OCH₃ | OH |
| 8.59 | Cl | OCH₃ | OCH₃ |
| 8.60 | Cl | OCH₃ | OC₂H₅ |
| 8.61 | Cl | OCH₃ | O(nC₃H₇) |
| 8.62 | Cl | OCH₃ | O(iC₃H₇) |
| 8.63 | Cl | OCH₃ | O(nC₄H₉) |
| 8.64 | Cl | OCH₃ | O(tC₄H₉) |
| 8.65 | Cl | OCH₃ | OPh |
| 8.66 | Cl | OCH₃ | SH |
| 8.67 | Cl | OCH₃ | SCH₃ |
| 8.68 | Cl | OCH₃ | SC₂H₅ |
| 8.69 | Cl | OCH₃ | S(nC₃H₇) |
| 8.70 | Cl | OCH₃ | S(iC₃H₇) |
| 8.71 | Cl | OCH₃ | S(nC₄H₉) |
| 8.72 | Cl | OCH₃ | S(tC₄H₉) |
| 8.73 | Cl | OCH₃ | SPh |
| 8.74 | Cl | OCH₃ | CCl₃ |
| 875 | Cl | OCH₃ | CH₂F |
| 8.76 | Cl | OCH₃ | CHF₂ |
| 8.77 | Cl | OCH₃ | CF₃ |
| 8.78 | Cl | OCH₃ | CF₂CHF₂ |
| 8.79 | Cl | OCH₃ | SO₃H |
| 8.80 | Cl | OCH₃ | SO₂CH₃ |
| 8.81 | Cl | OCH₃ | SO₂C₂H₅ |
| 8.82 | Cl | OCH₃ | SO₂(nC₃H₇) |
| 8.83 | Cl | OCH₃ | SO₂(iC₃H₇) |
| 8.84 | Cl | OCH₃ | SO₂(nC₄H₉) |
| 8.85 | Cl | OCH₃ | SO₂(tC₄H₉) |
| 8.86 | Cl | OCH₃ | SO₂Ph |
| 8.87 | Cl | OCH₃ | NH₂ |
| 8.88 | Cl | OCH₃ | NHCH₃ |

TABLE 2-continued

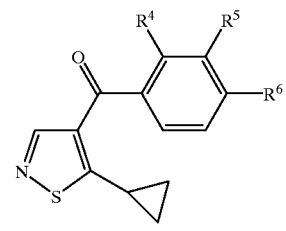

| No. | R⁴ | R⁵ | R⁶ |
|---|---|---|---|
| 8.89 | Cl | OCH₃ | NCH₃Ph |
| 8.90 | Cl | OCH₃ | N(CH₃)₂ |
| 8.91 | Cl | OCH₃ | NPh₂ |
| 8.92 | Cl | OCH₃ | CN |
| 8.93 | Cl | OCH₃ | NO₂ |
| 8.94 | CH₃ | OCH₃ | F |
| 8.95 | CH₃ | OCH₃ | Cl |
| 8.96 | CH₃ | OCH₃ | Br |
| 8.97 | CH₃ | OCH₃ | CH₃ |
| 8.98 | CH₃ | OCH₃ | C₂H₅ |
| 8.99 | CH₃ | OCH₃ | nC₃H₇ |
| 8.100 | CH₃ | OCH₃ | iC₃H₇ |
| 8.101 | CH₃ | OCH₃ | nC₄H₉ |
| 8.102 | CH₃ | OCH₃ | tC₄H₉ |
| 8.102 | CH₃ | OCH₃ | Ph |
| 8.103 | CH₃ | OCH₃ | OH |
| 8.104 | CH₃ | OCH₃ | OCH₃ |
| 8.105 | CH₃ | OCH₃ | OC₂H₅ |
| 8.106 | CH₃ | OCH₃ | O(nC₃H₇) |
| 8.107 | CH₃ | OCH₃ | O(iC₃H₇) |
| 8.108 | CH₃ | OCH₃ | O(nC₄H₉) |
| 8.109 | CH₃ | OCH₃ | O(tC₄H₉) |
| 8.110 | CH₃ | OCH₃ | OPh |
| 8.111 | CH₃ | OCH₃ | SH |
| 8.112 | CH₃ | OCH₃ | SCH₃ |
| 8.113 | CH₃ | OCH₃ | SC₂H₅ |
| 8.114 | CH₃ | OCH₃ | S(nC₃H₇) |
| 8.115 | CH₃ | OCH₃ | S(iC₃H₇) |
| 8.116 | CH₃ | OCH₃ | S(nC₄H₉) |
| 8.117 | CH₃ | OCH₃ | S(tC₄H₉) |
| 8.118 | CH₃ | OCH₃ | SPh |
| 8.119 | CH₃ | OCH₃ | CCl₃ |
| 8.120 | CH₃ | OCH₃ | CH₂F |
| 8.121 | CH₃ | OCH₃ | CHF₂ |
| 8.122 | CH₃ | OCH₃ | CF₃ |
| 8.123 | CH₃ | OCH₃ | CF₂CHF₂ |
| 8.124 | CH₃ | OCH₃ | SO₃H |
| 8.125 | CH₃ | OCH₃ | SO₂CH₃ |
| 8.126 | CH₃ | OCH₃ | SO₂C₂H₅ |
| 8.127 | CH₃ | OCH₃ | SO₂(nC₃H₇) |
| 8.128 | CH₃ | OCH₃ | SO₂(iC₃H₇) |
| 8.129 | CH₃ | OCH₃ | SO₂(nC₄H₉) |
| 8.130 | CH₃ | OCH₃ | SO₂(tC₄H₉) |
| 8.131 | CH₃ | OCH₃ | SO₂Ph |
| 8.132 | CH₃ | OCH₃ | NH₂ |
| 8.133 | CH₃ | OCH₃ | NHCH₃ |
| 8.134 | CH₃ | OCH₃ | NCH₃Ph |
| 8.135 | CH₃ | OCH₃ | N(CH₃)₂ |
| 8.136 | CH₃ | OCH₃ | NPh₂ |
| 8.137 | CH₃ | OCH₃ | CN |
| 8.138 | CH₃ | OCH₃ | NO₂ |
| 8.139 | CF₃ | OCH₃ | F |
| 8.140 | CF₃ | OCH₃ | Cl |
| 8.141 | CF₃ | OCH₃ | Br |
| 8.142 | CF₃ | OCH₃ | CH₃ |
| 8.143 | CF₃ | OCH₃ | C₂H₅ |
| 8.144 | CF₃ | OCH₃ | nC₃H₇ |
| 8.145 | CF₃ | OCH₃ | iC₃H₇ |
| 8.146 | CF₃ | OCH₃ | nC₄H₉ |
| 8.147 | CF₃ | OCH₃ | tC₄H₉ |
| 8.148 | CF₃ | OCH₃ | Ph |
| 8.149 | CF₃ | OCH₃ | OH |
| 8.150 | CF₃ | OCH₃ | OCH₃ |
| 8.151 | CF₃ | OCH₃ | OC₂H₅ |

TABLE 2-continued

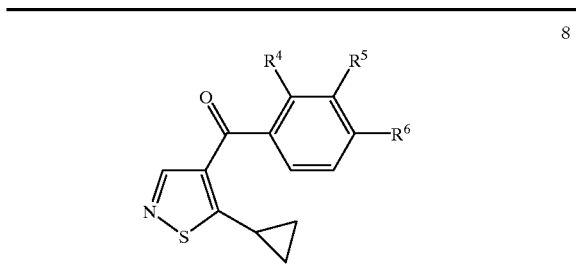

| No. | R4 | R5 | R6 |
|---|---|---|---|
| 8.152 | $CF_3$ | $OCH_3$ | $O(nC_3H_7)$ |
| 8.153 | $CF_3$ | $OCH_3$ | $O(iC_3H_7)$ |
| 8.154 | $CF_3$ | $OCH_3$ | $O(nC_4H_9)$ |
| 8.155 | $CF_3$ | $OCH_3$ | $O(tC_4H_9)$ |
| 8.156 | $CF_3$ | $OCH_3$ | OPh |
| 8.157 | $CF_3$ | $OCH_3$ | SH |
| 8.158 | $CF_3$ | $OCH_3$ | $SCH_3$ |
| 8.159 | $CF_3$ | $OCH_3$ | $SC_2H_5$ |
| 8.160 | $CF_3$ | $OCH_3$ | $S(nC_3H_7)$ |
| 8.161 | $CF_3$ | $OCH_3$ | $S(iC_3H_7)$ |
| 8.162 | $CF_3$ | $OCH_3$ | $S(nC_4H_9)$ |
| 8.163 | $CF_3$ | $OCH_3$ | $S(tC_4H_9)$ |
| 8.164 | $CF_3$ | $OCH_3$ | SPh |
| 8.165 | $CF_3$ | $OCH_3$ | $CCl_3$ |
| 8.166 | $CF_3$ | $OCH_3$ | $CH_2F$ |
| 8.167 | $CF_3$ | $OCH_3$ | $CHF_2$ |
| 8.168 | $CF_3$ | $OCH_3$ | $CF_3$ |
| 8.169 | $CF_3$ | $OCH_3$ | $CF_2CHF_2$ |
| 8.170 | $CF_3$ | $OCH_3$ | $SO_3H$ |
| 8.171 | $CF_3$ | $OCH_3$ | $SO_2CH_3$ |
| 8.172 | $CF_3$ | $OCH_3$ | $SO_2C_2H_5$ |
| 8.173 | $CF_3$ | $OCH_3$ | $SO_2(nC_3H_7)$ |
| 8.174 | $CF_3$ | $OCH_3$ | $SO_2(iC_3H_7)$ |
| 7.175 | $CF_3$ | $OCH_3$ | $SO_2(nC_4H_9)$ |
| 8.176 | $CF_3$ | $OCH_3$ | $SO_2(tC_4H_9)$ |
| 8.177 | $CF_3$ | $OCH_3$ | $SO_2Ph$ |
| 8.178 | $CF_3$ | $OCH_3$ | $NH_2$ |
| 8.179 | $CF_3$ | $OCH_3$ | $NHCH_3$ |
| 8.180 | $CF_3$ | $OCH_3$ | $NCH_3Ph$ |
| 8.181 | $CF_3$ | $OCH_3$ | $N(CH_3)_2$ |
| 8.182 | $CF_3$ | $OCH_3$ | $NPh_2$ |
| 8.183 | $CF_3$ | $OCH_3$ | CN |
| 8.184 | $CF_3$ | $OCH_3$ | $NO_2$ |
| 8.185 | $SO_2CH_3$ | $OCH_3$ | F |
| 8.186 | $SO_2CH_3$ | $OCH_3$ | Cl |
| 8.187 | $SO_2CH_3$ | $OCH_3$ | Br |
| 8.188 | $SO_2CH_3$ | $OCH_3$ | $CH_3$ |
| 8.189 | $SO_2CH_3$ | $OCH_3$ | $C_2H_5$ |
| 8.190 | $SO_2CH_3$ | $OCH_3$ | $nC_3H_7$ |
| 8.191 | $SO_2CH_3$ | $OCH_3$ | $iC_3H_7$ |
| 8.192 | $SO_2CH_3$ | $OCH_3$ | $nC_4H_9$ |
| 8.193 | $SO_2CH_3$ | $OCH_3$ | $tC_4H_9$ |
| 8.194 | $SO_2CH_3$ | $OCH_3$ | Ph |
| 8.195 | $SO_2CH_3$ | $OCH_3$ | OH |
| 8.196 | $SO_2CH_3$ | $OCH_3$ | $OCH_3$ |
| 8.197 | $SO_2CH_3$ | $OCH_3$ | $OC_2H_5$ |
| 8.198 | $SO_2CH_3$ | $OCH_3$ | $O(nC_3H_7)$ |
| 8.199 | $SO_2CH_3$ | $OCH_3$ | $O(iC_3H_7)$ |
| 8.200 | $SO_2CH_3$ | $OCH_3$ | $O(nC_4H_9)$ |
| 8.201 | $SO_2CH_3$ | $OCH_3$ | $O(tC_4H_9)$ |
| 8.202 | $SO_2CH_3$ | $OCH_3$ | OPh |
| 8.203 | $SO_2CH_3$ | $OCH_3$ | SH |
| 8.204 | $SO_2CH_3$ | $OCH_3$ | $SCH_3$ |
| 8.205 | $SO_2CH_3$ | $OCH_3$ | $SC_2H_5$ |
| 8.206 | $SO_2CH_3$ | $OCH_3$ | $S(nC_3H_7)$ |
| 8.207 | $SO_2CH_3$ | $OCH_3$ | $S(iC_3H_7)$ |
| 7.208 | $SO_2CH_3$ | $OCH_3$ | $S(nC_4H_9)$ |
| 8.209 | $SO_2CH_3$ | $OCH_3$ | $S(tC_4H_9)$ |
| 8.210 | $SO_2CH_3$ | $OCH_3$ | SPh |
| 8.211 | $SO_2CH_3$ | $OCH_3$ | $CCl_3$ |
| 8.212 | $SO_2CH_3$ | $OCH_3$ | $CH_2F$ |
| 8.213 | $SO_2CH_3$ | $OCH_3$ | $CHF_2$ |
| 8.214 | $SO_2CH_3$ | $OCH_3$ | $CF_3$ |
| 8.215 | $SO_2CH_3$ | $OCH_3$ | $CF_2CHF_2$ |

TABLE 2-continued

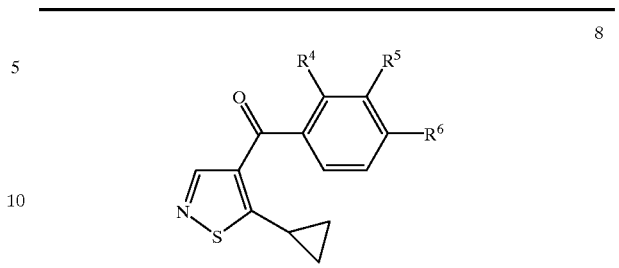

| No. | R4 | R5 | R6 |
|---|---|---|---|
| 8.216 | $SO_2CH_3$ | $OCH_3$ | $SO_3H$ |
| 8.217 | $SO_2CH_3$ | $OCH_3$ | $SO_2CH_3$ |
| 8.218 | $SO_2CH_3$ | $OCH_3$ | $SO_2C_2H_5$ |
| 8.219 | $SO_2CH_3$ | $OCH_3$ | $SO_2(nC_3H_7)$ |
| 8.220 | $SO_2CH_3$ | $OCH_3$ | $SO_2(iC_3H_7)$ |
| 8.221 | $SO_2CH_3$ | $OCH_3$ | $SO_2(nC_4H_9)$ |
| 8.222 | $SO_2CH_3$ | $OCH_3$ | $SO_2(tC_4H_9)$ |
| 8.223 | $SO_2CH_3$ | $OCH_3$ | $SO_2Ph$ |
| 8.224 | $SO_2CH_3$ | $OCH_3$ | $NH_2$ |
| 8.225 | $SO_2CH_3$ | $OCH_3$ | $NHCH_3$ |
| 8.226 | $SO_2CH_3$ | $OCH_3$ | $NCH_3Ph$ |
| 8.227 | $SO_2CH_3$ | $OCH_3$ | $N(CH_3)_2$ |
| 8.228 | $SO_2CH_3$ | $OCH_3$ | $NPh_2$ |
| 8.229 | $SO_2CH_3$ | $OCH_3$ | CN |
| 8.230 | $SO_2CH_3$ | $OCH_3$ | $NO_2$ |
| 8.231 | CN | $OCH_3$ | F |
| 8.232 | CN | $OCH_3$ | Cl |
| 8.233 | CN | $OCH_3$ | Br |
| 8.234 | CN | $OCH_3$ | $CH_3$ |
| 8.235 | CN | $OCH_3$ | $C_2H_5$ |
| 8.236 | CN | $OCH_3$ | $nC_3H_7$ |
| 8.237 | CN | $OCH_3$ | $iC_3H_7$ |
| 8.238 | CN | $OCH_3$ | $nC_4H_9$ |
| 8.239 | CN | $OCH_3$ | $tC_4H_9$ |
| 8.240 | CN | $OCH_3$ | Ph |
| 8.241 | CN | $OCH_3$ | OH |
| 8.242 | CN | $OCH_3$ | $OCH_3$ |
| 8.243 | CN | $OCH_3$ | $OC_2H_5$ |
| 8.244 | CN | $OCH_3$ | $O(nC_3H_7)$ |
| 8.245 | CN | $OCH_3$ | $O(iC_3H_7)$ |
| 8.246 | CN | $OCH_3$ | $O(nC_4H_9)$ |
| 8.247 | CN | $OCH_3$ | $O(tC_4H_9)$ |
| 8.248 | CN | $OCH_3$ | OPh |
| 8.249 | CN | $OCH_3$ | SH |
| 8.250 | CN | $OCH_3$ | $SCH_3$ |
| 8.251 | CN | $OCH_3$ | $SC_2H_5$ |
| 8.252 | CN | $OCH_3$ | $S(nC_3H_7)$ |
| 8.253 | CN | $OCH_3$ | $S(iC_3H_7)$ |
| 8.254 | CN | $OCH_3$ | $S(nC_4H_9)$ |
| 8.255 | CN | $OCH_3$ | $S(tC_4H_9)$ |
| 8.258 | CN | $OCH_3$ | SPh |
| 8.257 | CN | $OCH_3$ | $CCl_3$ |
| 8.258 | CN | $OCH_3$ | $CH_2F$ |
| 8.259 | CN | $OCH_3$ | $CHF_2$ |
| 8.260 | CN | $OCH_3$ | $CF_3$ |
| 8.261 | CN | $OCH_3$ | $CF_2CHF_2$ |
| 8.262 | CN | $OCH_3$ | $SO_3H$ |
| 8.263 | CN | $OCH_3$ | $SO_2CH_3$ |
| 8.264 | CN | $OCH_3$ | $SO_2C_2H_5$ |
| 8.265 | CN | $OCH_3$ | $SO_2(nC_3H_7)$ |
| 8.266 | CN | $OCH_3$ | $SO_2(iC_3H_7)$ |
| 8.267 | CN | $OCH_3$ | $SO_2(nC_4H_9)$ |
| 8.268 | CN | $OCH_3$ | $SO_2(tC_4H_9)$ |
| 8.269 | CN | $OCH_3$ | $SO_2Ph$ |
| 8.270 | CN | $OCH_3$ | $NH_2$ |
| 8.271 | CN | $OCH_3$ | $NHCH_3$ |
| 8.272 | CN | $OCH_3$ | $NCH_3Ph$ |
| 8.273 | CN | $OCH_3$ | $N(CH_3)_2$ |
| 8.274 | CN | $OCH_3$ | $NPh_2$ |
| 8.275 | CN | $OCH_3$ | CN |
| 8.276 | CN | $OCH_3$ | $NO_2$ |

TABLE 3

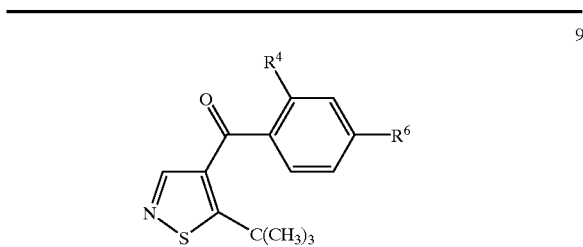

| No. | R⁴ | R⁶ |
|---|---|---|
| 9.1 | F | F |
| 9.2 | F | Cl |
| 9.3 | F | Br |
| 9.4 | F | CH₃ |
| 9.5 | F | C₂H₅ |
| 9.6 | F | nC₃H₉ |
| 9.7 | F | iC₃H₉ |
| 9.8 | F | nC₄H₉ |
| 9.9 | F | tC₄H₉ |
| 9.10 | F | Ph |
| 9.11 | F | OH |
| 9.12 | F | OCH₃ |
| 9.13 | F | OC₂H₅ |
| 9.14 | F | O(nC₃H₉) |
| 9.15 | F | O(iC₃H₉) |
| 9.16 | F | O(nC₄H₉) |
| 9.17 | F | O(tC₄H₉) |
| 9.18 | F | OPh |
| 9.19 | F | SH |
| 9.20 | F | SCH₃ |
| 9.21 | F | SC₂H₅ |
| 9.22 | F | S(nC₃H₉) |
| 9.23 | F | S(iC₃H₉) |
| 9.24 | F | S(nC₄H₉) |
| 9.25 | F | S(tC₄H₉) |
| 9.26 | F | SPh |
| 9.27 | F | CCl₃ |
| 9.28 | F | CH₂F |
| 9.29 | F | CHF₂ |
| 9.30 | F | CF₃ |
| 9.31 | F | CF₂CHF₂ |
| 9.32 | F | SO₃H |
| 9.33 | F | SO₂CH₃ |
| 9.34 | F | SO₂C₂H₅ |
| 9.35 | F | SO₂(nC₃H₉) |
| 9.36 | F | SO₂(iC₃H₉) |
| 9.37 | F | SO₂(nC₄H₉) |
| 9.38 | F | SO₂(tC₄H₉) |
| 9.39 | F | SO₂Ph |
| 9.40 | F | NH₂ |
| 9.41 | F | NHCH₃ |
| 9.42 | F | NCH₃Ph |
| 9.43 | F | N(CH₃)₂ |
| 9.44 | F | NPh₂ |
| 9.45 | F | CN |
| 9.46 | F | NO₂ |
| 9.47 | Cl | F |
| 9.48 | Cl | Cl |
| 9.49 | Cl | Br |
| 9.50 | Cl | CH₃ |
| 9.51 | Cl | C₂H₅ |
| 9.53 | Cl | nC₃H₉ |
| 9.54 | Cl | iC₃H₉ |
| 9.55 | Cl | nC₄H₉ |
| 9.56 | Cl | tC₄H₉ |
| 9.57 | Cl | Ph |
| 9.58 | Cl | OH |
| 9.59 | Cl | OCH₃ |
| 9.60 | Cl | OC₂H₅ |
| 9.61 | Cl | O(nC₃H₉) |
| 9.62 | Cl | O(iC₃H₉) |
| 9.63 | Cl | O(nC₄H₉) |
| 9.64 | Cl | O(tC₄H₉) |
| 9.65 | Cl | OPh |
| 9.66 | Cl | SH |

TABLE 3-continued

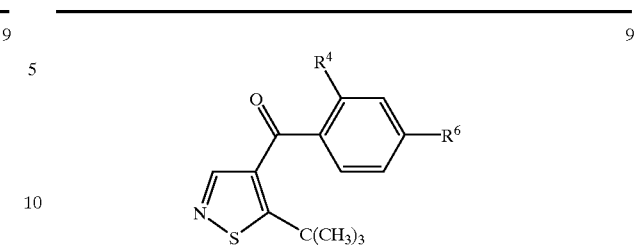

| No. | R⁴ | R⁶ |
|---|---|---|
| 9.67 | Cl | SCH₃ |
| 9.68 | Cl | SC₂H₅ |
| 9.69 | Cl | S(nC₃H₉) |
| 9.70 | Cl | S(iC₃H₉) |
| 9.71 | Cl | S(nC₄H₉) |
| 9.72 | Cl | S(tC₄H₉) |
| 9.73 | Cl | SPh |
| 9.74 | Cl | CCl₃ |
| 9.75 | Cl | CH₂F |
| 9.76 | Cl | CHF₂ |
| 9.77 | Cl | CF₃ |
| 9.78 | Cl | CF₂CHF₂ |
| 9.79 | Cl | SO₃H |
| 9.80 | Cl | SO₂CH₃ |
| 9.81 | Cl | SO₂C₂H₅ |
| 9.82 | Cl | SO₂(nC₃H₉) |
| 9.83 | Cl | SO₂(iC₃H₉) |
| 9.84 | Cl | SO₂(nC₄H₉) |
| 9.85 | Cl | SO₂(tC₄H₉) |
| 9.86 | Cl | SO₂Ph |
| 9.87 | Cl | NH₂ |
| 9.88 | Cl | NHCH₃ |
| 9.89 | Cl | NCH₃Ph |
| 9.90 | Cl | N(CH₃)₂ |
| 9.91 | Cl | NPh₂ |
| 9.92 | Cl | CN |
| 9.93 | Cl | NO₂ |
| 9.94 | CH₃ | F |
| 9.95 | CH₃ | Cl |
| 9.96 | CH₃ | Br |
| 9.97 | CH₃ | CH₃ |
| 9.98 | CH₃ | C₂H₅ |
| 9.99 | CH₃ | nC₃H₉ |
| 9.100 | CH₃ | iC₃H₉ |
| 9.101 | CH₃ | nC₄H₉ |
| 9.102 | CH₃ | tC₄H₉ |
| 9.102 | CH₃ | Ph |
| 9.103 | CH₃ | OH |
| 9.104 | CH₃ | OCH₃ |
| 9.105 | CH₃ | OC₂H₅ |
| 9.106 | CH₃ | O(nC₃H₉) |
| 9.107 | CH₃ | O(iC₃H₉) |
| 9.108 | CH₃ | O(nC₄H₉) |
| 9.109 | CH₃ | O(tC₄H₉) |
| 9.110 | CH₃ | OPh |
| 9.111 | CH₃ | SH |
| 9.112 | CH₃ | SCH₃ |
| 9.113 | CH₃ | SC₂H₅ |
| 9.114 | CH₃ | S(nC₃H₉) |
| 9.115 | CH₃ | S(iC₃H₉) |
| 9.116 | CH₃ | S(nC₄H₉) |
| 9.117 | CH₃ | S(tC₄H₉) |
| 9.118 | CH₃ | SPh |
| 9.119 | CH₃ | CCl₃ |
| 9.120 | CH₃ | CH₂F |
| 9.121 | CH₃ | CHF₂ |
| 9.122 | CH₃ | CF₃ |
| 9.123 | CH₃ | CF₂CHF₂ |
| 9.124 | CH₃ | SO₃H |
| 9.125 | CH₃ | SO₂CH₃ |
| 9.126 | CH₃ | SO₂C₂H₅ |
| 9.127 | CH₃ | SO₂(nC₃H₉) |
| 9.128 | CH₃ | SO₂(iC₃H₉) |
| 9.129 | CH₃ | SO₂(nC₄H₉) |
| 9.130 | CH₃ | SO₂(tC₄H₉) |

TABLE 3-continued

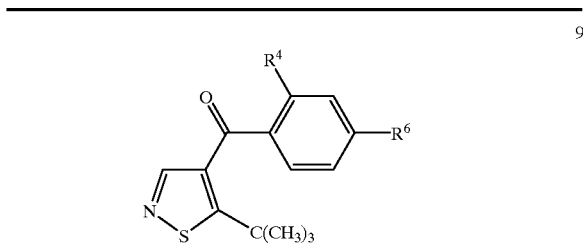

| No. | R⁴ | R⁶ |
|---|---|---|
| 9.131 | CH₃ | SO₂Ph |
| 9.132 | CH₃ | NH₂ |
| 9.133 | CH₃ | NHCH₃ |
| 9.134 | CH₃ | NCH₃Ph |
| 9.135 | CH₃ | N(CH₃)₂ |
| 9.136 | CH₃ | NPh₂ |
| 9.137 | CH₃ | CN |
| 9.138 | CH₃ | NO₂ |
| 9.139 | CF₃ | F |
| 9.140 | CF₃ | Cl |
| 9.141 | CF₃ | Br |
| 9.142 | CF₃ | CH₃ |
| 9.143 | CF₃ | C₂H₅ |
| 9.144 | CF₃ | nC₃H₉ |
| 9.145 | CF₃ | iC₃H₉ |
| 9.146 | CF₃ | nC₄H₉ |
| 9.147 | CF₃ | tC₄H₉ |
| 9.148 | CF₃ | Ph |
| 9.149 | CF₃ | OH |
| 9.150 | CF₃ | OCH₃ |
| 9.151 | CF₃ | OC₂H₅ |
| 9.152 | CF₃ | O(nC₃H₉) |
| 9.153 | CF₃ | O(iC₃H₉) |
| 9.154 | CF₃ | O(nC₄H₉) |
| 9.155 | CF₃ | O(tC₄H₉) |
| 9.156 | CF₃ | OPh |
| 9.157 | CF₃ | SH |
| 9.158 | CF₃ | SCH₃ |
| 9.159 | CF₃ | SC₂H₅ |
| 9.160 | CF₃ | S(nC₃H₉) |
| 9.161 | CF₃ | S(iC₃H₉) |
| 9.162 | CF₃ | S(nC₄H₉) |
| 9.163 | CF₃ | S(tC₄H₉) |
| 9.164 | CF₃ | SPh |
| 9.165 | CF₃ | CCl₃ |
| 9.166 | CF₃ | CH₂F |
| 9.167 | CF₃ | CHF₂ |
| 9.168 | CF₃ | CF₃ |
| 9.169 | CF₃ | CF₂CHF₂ |
| 9.170 | CF₃ | SO₃H |
| 9.171 | CF₃ | SO₂CH₃ |
| 9.172 | CF₃ | SO₂C₂H₅ |
| 9.173 | CF₃ | SO₂(nC₃H₉) |
| 9.174 | CF₃ | SO₂(iC₃H₉) |
| 9.175 | CF₃ | SO₂(nC₄H₉) |
| 9.176 | CF₃ | SO₂(tC₄H₉) |
| 9.177 | CF₃ | SO₂Ph |
| 9.178 | CF₃ | NH₂ |
| 9.179 | CF₃ | NHCH₃ |
| 9.180 | CF₃ | NCH₃Ph |
| 9.181 | CF₃ | N(CH₃)₂ |
| 9.182 | CF₃ | NPh₂ |
| 9.183 | CF₃ | CN |
| 9.184 | CF₃ | NO₂ |
| 9.185 | SO₂CH₃ | F |
| 9.186 | SO₂CH₃ | Cl |
| 9.187 | SO₂CH₃ | Br |
| 9.188 | SO₂CH₃ | CH₃ |
| 9.189 | SO₂CH₃ | C₂H₅ |
| 9.190 | SO₂CH₃ | nC₃H₉ |
| 9.191 | SO₂CH₃ | iC₃H₉ |
| 9.192 | SO₂CH₃ | nC₄H₉ |
| 9.193 | SO₂CH₃ | tC₄H₉ |
| 9.194 | SO₂CH₃ | Ph |
| 9.195 | SO₂CH₃ | OH |

TABLE 3-continued

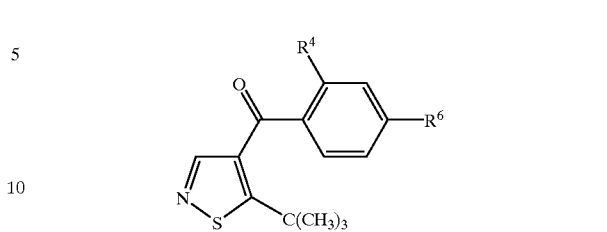

| No. | R⁴ | R⁶ |
|---|---|---|
| 9.196 | SO₂CH₃ | OCH₃ |
| 9.197 | SO₂CH₃ | OC₂H₅ |
| 9.198 | SO₂CH₃ | O(nC₃H₉) |
| 9.199 | SO₂CH₃ | O(iC₃H₉) |
| 9.200 | SO₂CH₃ | O(nC₄H₉) |
| 9.201 | SO₂CH₃ | O(tC₄H₉) |
| 9.202 | SO₂CH₃ | OPh |
| 9.203 | SO₂CH₃ | SH |
| 9.204 | SO₂CH₃ | SCH₃ |
| 9.205 | SO₂CH₃ | SC₂H₅ |
| 9.206 | SO₂CH₃ | S(nC₃H₉) |
| 9.207 | SO₂CH₃ | S(iC₃H₉) |
| 9.208 | SO₂CH₃ | S(nC₄H₉) |
| 9.209 | SO₂CH₃ | S(tC₄H₉) |
| 9.210 | SO₂CH₃ | SPh |
| 9.211 | SO₂CH₃ | CCl₃ |
| 9.212 | SO₂CH₃ | CH₂F |
| 9.213 | SO₂CH₃ | CHF₂ |
| 9.214 | SO₂CH₃ | CF₃ |
| 9.215 | SO₂CH₃ | CF₂CHF₂ |
| 9.216 | SO₂CH₃ | SO₃H |
| 9.217 | SO₂CH₃ | SO₂CH₃ |
| 9.218 | SO₂CH₃ | SO₂C₂H₅ |
| 9.219 | SO₂CH₃ | SO₂(nC₃H₉) |
| 9.220 | SO₂CH₃ | SO₂(iC₃H₉) |
| 9.221 | SO₂CH₃ | SO₂(nC₄H₉) |
| 9.222 | SO₂CH₃ | SO₂(tC₄H₉) |
| 9.223 | SO₂CH₃ | SO₂Ph |
| 9.224 | SO₂CH₃ | NH₂ |
| 9.225 | SO₂CH₃ | NHCH₃ |
| 9.226 | SO₂CH₃ | NCH₃Ph |
| 9.227 | SO₂CH₃ | N(CH₃)₂ |
| 9.228 | SO₂CH₃ | NPh₂ |
| 9.229 | SO₂CH₃ | CN |
| 9.230 | SO₂CH₃ | NO₂ |
| 9.231 | CN | F |
| 9.232 | CN | Cl |
| 9.233 | CN | Br |
| 9.234 | CN | CH₃ |
| 9.235 | CN | C₂H₅ |
| 9.236 | CN | nC₃H₉ |
| 9.237 | CN | iC₃H₉ |
| 9.238 | CN | nC₄H₉ |
| 9.239 | CN | tC₄H₉ |
| 9.240 | CN | Ph |
| 9.241 | CN | OH |
| 9.242 | CN | OCH₃ |
| 9.243 | CN | OC₂H₅ |
| 9.244 | CN | O(nC₃H₉) |
| 9.245 | CN | O(iC₃H₉) |
| 9.246 | CN | O(nC₄H₉) |
| 9.247 | CN | O(tC₄H₉) |
| 9.248 | CN | OPh |
| 9.249 | CN | SH |
| 9.250 | CN | SCH₃ |
| 9.251 | CN | SC₂H₅ |
| 9.252 | CN | S(nC₃H₉) |
| 9.253 | CN | S(iC₃H₉) |
| 9.254 | CN | S(nC₄H₉) |
| 9.255 | CN | S(tC₄H₉) |
| 9.256 | CN | SPh |
| 9.257 | CN | CCl₃ |
| 9.258 | CN | CH₂F |
| 9.259 | CN | CHF₂ |
| 9.260 | CN | CF₃ |

TABLE 3-continued

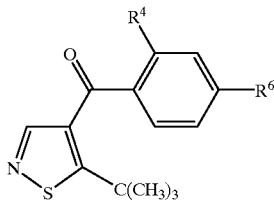

| No. | R⁴ | R⁶ |
|---|---|---|
| 9.261 | CN | CF$_2$CHF$_2$ |
| 9.262 | CN | SO$_3$H |
| 9.263 | CN | SO$_2$CH$_3$ |
| 9.264 | CN | SO$_2$C$_2$H$_5$ |
| 9.265 | CN | SO$_2$(nC$_3$H$_9$) |
| 9.266 | CN | SO$_2$(iC$_3$H$_9$) |
| 9.267 | CN | SO$_2$(nC$_4$H$_9$) |
| 9.268 | CN | SO$_2$(tC$_4$H$_9$) |
| 9.269 | CN | SO$_2$Ph |
| 9.270 | CN | NH$_2$ |
| 9.271 | CN | NHCH$_3$ |
| 9.272 | CN | NCH$_3$Ph |
| 9.273 | CN | N(CH$_3$)$_2$ |
| 9.274 | CN | NPh$_2$ |
| 9.275 | CN | CN |
| 9.276 | CN | NO$_2$ |

TABLE 4

| No. | R⁴ | R⁵ | R⁶ |
|---|---|---|---|
| 10.1 | F | OCH$_3$ | F |
| 10.2 | F | OCH$_3$ | Cl |
| 10.3 | F | OCH$_3$ | Br |
| 10.4 | F | OCH$_3$ | CH$_3$ |
| 10.5 | F | OCH$_3$ | C$_2$H$_5$ |
| 10.6 | F | OCH$_3$ | nC$_3$H$_7$ |
| 10.7 | F | OCH$_3$ | iC$_3$H$_7$ |
| 10.8 | F | OCH$_3$ | nC$_4$H$_9$ |
| 10.9 | F | OCH$_3$ | tC$_4$H$_9$ |
| 10.10 | F | OCH$_3$ | Ph |
| 10.11 | F | OCH$_3$ | OH |
| 10.12 | F | OCH$_3$ | OCH$_3$ |
| 10.13 | F | OCH$_3$ | OC$_2$H$_5$ |
| 10.14 | F | OCH$_3$ | O(nC$_3$H$_7$) |
| 10.15 | F | OCH$_3$ | O(iC$_3$H$_7$) |
| 10.16 | F | OCH$_3$ | O(nC$_4$H$_9$) |
| 10.17 | F | OCH$_3$ | O(tC$_4$H$_9$) |
| 10.18 | F | OCH$_3$ | OPh |
| 10.19 | F | OCH$_3$ | SH |
| 10.20 | F | OCH$_3$ | SCH$_3$ |
| 10.21 | F | OCH$_3$ | SC$_2$H$_5$ |
| 10.22 | F | OCH$_3$ | S(nC$_3$H$_7$) |
| 10.23 | F | OCH$_3$ | S(iC$_3$H$_7$) |
| 10.24 | F | OCH$_3$ | S(nC$_4$H$_9$) |
| 10.25 | F | OCH$_3$ | S(tC$_4$H$_9$) |
| 10.26 | F | OCH$_3$ | SPh |
| 10.27 | F | OCH$_3$ | CCl$_3$ |
| 10.28 | F | OCH$_3$ | CH$_2$F |
| 10.29 | F | OCH$_3$ | CHF$_2$ |
| 10.30 | F | OCH$_3$ | CF$_3$ |
| 10.31 | F | OCH$_3$ | CF$_2$CHF$_2$ |
| 10.32 | F | OCH$_3$ | SO$_3$H |
| 10.33 | F | OCH$_3$ | SO$_2$CH$_3$ |
| 10.34 | F | OCH$_3$ | SO$_2$C$_2$H$_5$ |
| 10.35 | F | OCH$_3$ | SO$_2$(nC$_3$H$_7$) |
| 10.36 | F | OCH$_3$ | SO$_2$(iC$_3$H$_7$) |
| 10.37 | F | OCH$_3$ | SO$_2$(nC$_4$H$_9$) |
| 10.38 | F | OCH$_3$ | SO$_2$(tC$_4$H$_9$) |
| 10.39 | F | OCH$_3$ | SO$_2$Ph |
| 10.40 | F | OCH$_3$ | NH$_2$ |
| 10.41 | F | OCH$_3$ | NHCH$_3$ |
| 10.42 | F | OCH$_3$ | NCH$_3$Ph |
| 10.43 | F | OCH$_3$ | N(CH$_3$)$_2$ |
| 10.44 | F | OCH$_3$ | NPh$_2$ |
| 10.45 | F | OCH$_3$ | CN |
| 10.46 | F | OCH$_3$ | NO$_2$ |
| 10.47 | Cl | OCH$_3$ | F |
| 10.48 | Cl | OCH$_3$ | Cl |
| 10.49 | Cl | OCH$_3$ | Br |
| 10.50 | Cl | OCH$_3$ | CH$_3$ |
| 10.51 | Cl | OCH$_3$ | C$_2$H$_5$ |
| 10.53 | Cl | OCH$_3$ | nC$_3$H$_7$ |
| 10.54 | Cl | OCH$_3$ | iC$_3$H$_7$ |
| 10.55 | Cl | OCH$_3$ | nC$_4$H$_9$ |
| 10.56 | Cl | OCH$_3$ | tC$_4$H$_9$ |
| 10.57 | Cl | OCH$_3$ | Ph |
| 10.58 | Cl | OCH$_3$ | OH |
| 10.59 | Cl | OCH$_3$ | OCH$_3$ |
| 10.60 | Cl | OCH$_3$ | OC$_2$H$_5$ |
| 10.61 | Cl | OCH$_3$ | O(nC$_3$H$_7$) |
| 10.62 | Cl | OCH$_3$ | O(iC$_3$H$_7$) |
| 10.63 | Cl | OCH$_3$ | O(nC$_4$H$_9$) |
| 10.64 | Cl | OCH$_3$ | O(tC$_4$H$_9$) |
| 10.65 | Cl | OCH$_3$ | OPh |
| 10.66 | Cl | OCH$_3$ | SH |
| 10.67 | Cl | OCH$_3$ | SCH$_3$ |
| 10.68 | Cl | OCH$_3$ | SC$_2$H$_5$ |
| 10.69 | Cl | OCH$_3$ | S(nC$_3$H$_7$) |
| 10.70 | Cl | OCH$_3$ | S(iC$_3$H$_7$) |
| 10.71 | Cl | OCH$_3$ | S(nC$_4$H$_9$) |
| 10.72 | Cl | OCH$_3$ | S(tC$_4$H$_9$) |
| 10.73 | Cl | OCH$_3$ | SPh |
| 10.74 | Cl | OCH$_3$ | CCl$_3$ |
| 10.75 | Cl | OCH$_3$ | CH$_2$F |
| 10.76 | Cl | OCH$_3$ | CHF$_2$ |
| 10.77 | Cl | OCH$_3$ | CF$_3$ |
| 10.78 | Cl | OCH$_3$ | CF$_2$CHF$_2$ |
| 10.79 | Cl | OCH$_3$ | SO$_3$H |
| 10.80 | Cl | OCH$_3$ | SO$_2$CH$_3$ |
| 10.81 | Cl | OCH$_3$ | SO$_2$C$_2$H$_5$ |
| 10.82 | Cl | OCH$_3$ | SO$_2$(nC$_3$H$_7$) |
| 10.83 | Cl | OCH$_3$ | SO$_2$(iC$_3$H$_7$) |
| 10.84 | Cl | OCH$_3$ | SO$_2$(nC$_4$H$_9$) |
| 10.85 | Cl | OCH$_3$ | SO$_2$(tC$_4$H$_9$) |
| 10.86 | Cl | OCH$_3$ | SO$_2$Ph |
| 10.87 | Cl | OCH$_3$ | NH$_2$ |
| 10.88 | Cl | OCH$_3$ | NHCH$_3$ |
| 10.89 | Cl | OCH$_3$ | NCH$_3$Ph |
| 10.90 | Cl | OCH$_3$ | N(CH$_3$)$_2$ |
| 10.91 | Cl | OCH$_3$ | NPh$_2$ |
| 10.92 | Cl | OCH$_3$ | CN |
| 10.93 | Cl | OCH$_3$ | NO$_2$ |
| 10.94 | CH$_3$ | OCH$_3$ | F |
| 10.95 | CH$_3$ | OCH$_3$ | Cl |

TABLE 4-continued

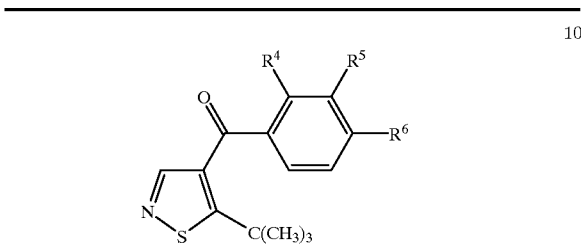

| No. | R⁴ | R⁵ | R⁶ |
|---|---|---|---|
| 10.96 | CH₃ | OCH₃ | Br |
| 10.97 | CH₃ | OCH₃ | CH₃ |
| 10.98 | CH₃ | OCH₃ | C₂H₅ |
| 10.99 | CH₃ | OCH₃ | nC₃H₇ |
| 10.100 | CH₃ | OCH₃ | iC₃H₇ |
| 10.101 | CH₃ | OCH₃ | nC₄H₉ |
| 10.102 | CH₃ | OCH₃ | tC₄H₉ |
| 10.102 | CH₃ | OCH₃ | Ph |
| 10.103 | CH₃ | OCH₃ | OH |
| 10.104 | CH₃ | OCH₃ | OCH₃ |
| 10.105 | CH₃ | OCH₃ | OC₂H₅ |
| 10.106 | CH₃ | OCH₃ | O(nC₃H₇) |
| 10.107 | CH₃ | OCH₃ | O(iC₃H₇) |
| 10.108 | CH₃ | OCH₃ | O(nC₄H₉) |
| 10.109 | CH₃ | OCH₃ | O(tC₄H₉) |
| 10.110 | CH₃ | OCH₃ | OPh |
| 10.111 | CH₃ | OCH₃ | SH |
| 10.112 | CH₃ | OCH₃ | SCH₃ |
| 10.113 | CH₃ | OCH₃ | SC₂H₅ |
| 10.114 | CH₃ | OCH₃ | S(nC₃H₇) |
| 10.115 | CH₃ | OCH₃ | S(iC₃H₇) |
| 10.116 | CH₃ | OCH₃ | S(nC₄H₉) |
| 10.117 | CH₃ | OCH₃ | S(tC₄H₉) |
| 10.118 | CH₃ | OCH₃ | SPh |
| 10.119 | CH₃ | OCH₃ | CCl₃ |
| 10.120 | CH₃ | OCH₃ | CH₂F |
| 10.121 | CH₃ | OCH₃ | CHF₂ |
| 10.122 | CH₃ | OCH₃ | CF₃ |
| 10.123 | CH₃ | OCH₃ | CF₂CHF₂ |
| 10.124 | CH₃ | OCH₃ | SO₃H |
| 10.125 | CH₃ | OCH₃ | SO₂CH₃ |
| 10.126 | CH₃ | OCH₃ | SO₂C₂H₅ |
| 10.127 | CH₃ | OCH₃ | SO₂(nC₃H₇) |
| 10.128 | CH₃ | OCH₃ | SO₂(iC₃H₇) |
| 10.129 | CH₃ | OCH₃ | SO₂(nC₄H₉) |
| 10.130 | CH₃ | OCH₃ | SO₂(tC₄H₉) |
| 10.131 | CH₃ | OCH₃ | SO₂Ph |
| 10.132 | CH₃ | OCH₃ | NH₂ |
| 10.133 | CH₃ | OCH₃ | NHCH₃ |
| 10.134 | CH₃ | OCH₃ | NCH₃Ph |
| 10.135 | CH₃ | OCH₃ | N(CH₃)₂ |
| 10.136 | CH₃ | OCH₃ | NPh₂ |
| 10.137 | CH₃ | OCH₃ | CN |
| 10.138 | CH₃ | OCH₃ | NO₂ |
| 10.139 | CF₃ | OCH₃ | F |
| 10.140 | CF₃ | OCH₃ | Cl |
| 10.141 | CF₃ | OCH₃ | Br |
| 10.142 | CF₃ | OCH₃ | CH₃ |
| 10.143 | CF₃ | OCH₃ | C₂H₅ |
| 10.144 | CF₃ | OCH₃ | nC₃H₇ |
| 10.145 | CF₃ | OCH₃ | iC₃H₇ |
| 10.146 | CF₃ | OCH₃ | nC₄H₉ |
| 10.147 | CF₃ | OCH₃ | tC₄H₉ |
| 10.148 | CF₃ | OCH₃ | Ph |
| 10.149 | CF₃ | OCH₃ | OH |
| 10.150 | CF₃ | OCH₃ | OCH₃ |
| 10.151 | CF₃ | OCH₃ | OC₂H₅ |
| 10.152 | CF₃ | OCH₃ | O(nC₃H₇) |
| 10.153 | CF₃ | OCH₃ | O(iC₃H₇) |
| 10.154 | CF₃ | OCH₃ | O(nC₄H₉) |
| 10.155 | CF₃ | OCH₃ | O(tC₄H₉) |
| 10.156 | CF₃ | OCH₃ | OPh |
| 10.157 | CF₃ | OCH₃ | SH |
| 10.158 | CF₃ | OCH₃ | SCH₃ |
| 10.159 | CF₃ | OCH₃ | SC₂H₅ |
| 10.160 | CF₃ | OCH₃ | S(nC₃H₇) |
| 10.161 | CF₃ | OCH₃ | S(iC₃H₇) |
| 10.162 | CF₃ | OCH₃ | S(nC₄H₉) |
| 10.163 | CF₃ | OCH₃ | S(tC₄H₉) |
| 10.164 | CF₃ | OCH₃ | SPh |
| 10.165 | CF₃ | OCH₃ | CCl₃ |
| 10.166 | CF₃ | OCH₃ | CH₂F |
| 10.167 | CF₃ | OCH₃ | CHF₂ |
| 10.168 | CF₃ | OCH₃ | CF₃ |
| 10.169 | CF₃ | OCH₃ | CF₂CHF₂ |
| 10.170 | CF₃ | OCH₃ | SO₃H |
| 10.171 | CF₃ | OCH₃ | SO₂CH₃ |
| 10.172 | CF₃ | OCH₃ | SO₂C₂H₅ |
| 10.173 | CF₃ | OCH₃ | SO₂(nC₃H₇) |
| 10.174 | CF₃ | OCH₃ | SO₂(iC₃H₇) |
| 10.175 | CF₃ | OCH₃ | SO₂(nC₄H₉) |
| 10.176 | CF₃ | OCH₃ | SO₂(tC₄H₉) |
| 10.177 | CF₃ | OCH₃ | SO₂Ph |
| 10.178 | CF₃ | OCH₃ | NH₂ |
| 10.179 | CF₃ | OCH₃ | NHCH₃ |
| 10.180 | CF₃ | OCH₃ | NCH₃Ph |
| 10.181 | CF₃ | OCH₃ | N(CH₃)₂ |
| 10.182 | CF₃ | OCH₃ | NPh₂ |
| 10.183 | CF₃ | OCH₃ | CN |
| 10.184 | CF₃ | OCH₃ | NO₂ |
| 10.185 | SO₂CH₃ | OCH₃ | F |
| 10.186 | SO₂CH₃ | OCH₃ | Cl |
| 10.187 | SO₂CH₃ | OCH₃ | Br |
| 10.188 | SO₂CH₃ | OCH₃ | CH₃ |
| 10.189 | SO₂CH₃ | OCH₃ | C₂H₅ |
| 10.190 | SO₂CH₃ | OCH₃ | nC₃H₇ |
| 10.191 | SO₂CH₃ | OCH₃ | iC₃H₇ |
| 10.192 | SO₂CH₃ | OCH₃ | nC₄H₉ |
| 10.193 | SO₂CH₃ | OCH₃ | tC₄H₉ |
| 10.194 | SO₂CH₃ | OCH₃ | Ph |
| 10.195 | SO₂CH₃ | OCH₃ | OH |
| 10.196 | SO₂CH₃ | OCH₃ | OCH₃ |
| 10.197 | SO₂CH₃ | OCH₃ | OC₂H₅ |
| 10.198 | SO₂CH₃ | OCH₃ | O(nC₃H₇) |
| 10.199 | SO₂CH₃ | OCH₃ | O(iC₃H₇) |
| 10.200 | SO₂CH₃ | OCH₃ | O(nC₄H₉) |
| 10.201 | SO₂CH₃ | OCH₃ | O(tC₄H₉) |
| 10.202 | SO₂CH₃ | OCH₃ | OPh |
| 10.203 | SO₂CH₃ | OCH₃ | SH |
| 10.204 | SO₂CH₃ | OCH₃ | SCH₃ |
| 10.205 | SO₂CH₃ | OCH₃ | SC₂H₅ |
| 10.206 | SO₂CH₃ | OCH₃ | S(nC₃H₇) |
| 10.207 | SO₂CH₃ | OCH₃ | S(iC₃H₇) |
| 10.208 | SO₂CH₃ | OCH₃ | S(nC₄H₉) |
| 10.209 | SO₂CH₃ | OCH₃ | S(tC₄H₉) |
| 10.210 | SO₂CH₃ | OCH₃ | SPh |
| 10.211 | SO₂CH₃ | OCH₃ | CCl₃ |
| 10.212 | SO₂CH₃ | OCH₃ | CH₂F |
| 10.213 | SO₂CH₃ | OCH₃ | CHF₂ |
| 10.214 | SO₂CH₃ | OCH₃ | CF₃ |
| 10.215 | SO₂CH₃ | OCH₃ | CF₂CHF₂ |
| 10.216 | SO₂CH₃ | OCH₃ | SO₃H |
| 10.217 | SO₂CH₃ | OCH₃ | SO₂CH₃ |
| 10.218 | SO₂CH₃ | OCH₃ | SO₂C₂H₅ |
| 10.219 | SO₂CH₃ | OCH₃ | SO₂(nC₃H₇) |
| 10.220 | SO₂CH₃ | OCH₃ | SO₂(iC₃H₇) |
| 10.221 | SO₂CH₃ | OCH₃ | SO₂(nC₄H₉) |
| 10.222 | SO₂CH₃ | OCH₃ | SO₂(tC₄H₉) |
| 10.223 | SO₂CH₃ | OCH₃ | SO₂Ph |
| 10.224 | SO₂CH₃ | OCH₃ | NH₂ |

TABLE 4-continued

[Structure: benzoyl-isothiazole with R4, R5, R6 substituents and C(CH3)3 on isothiazole]

| No. | R⁴ | R⁵ | R⁶ |
|---|---|---|---|
| 10.225 | SO₂CH₃ | OCH₃ | NHCH₃ |
| 10.226 | SO₂CH₃ | OCH₃ | NCH₃Ph |
| 10.227 | SO₂CH₃ | OCH₃ | N(CH₃)₂ |
| 10.228 | SO₂CH₃ | OCH₃ | NPh₂ |
| 10.229 | SO₂CH₃ | OCH₃ | CN |
| 10.230 | SO₂CH₃ | OCH₃ | NO₂ |
| 10.231 | CN | OCH₃ | F |
| 10.232 | CN | OCH₃ | Cl |
| 10.233 | CN | OCH₃ | Br |
| 10.234 | CN | OCH₃ | CH₃ |
| 10.235 | CN | OCH₃ | C₂H₅ |
| 10.236 | CN | OCH₃ | nC₃H₇ |
| 10.237 | CN | OCH₃ | iC₃H₇ |
| 10.238 | CN | OCH₃ | nC₄H₉ |
| 10.239 | CN | OCH₃ | tC₄H₉ |
| 10.240 | CN | OCH₃ | Ph |
| 10.241 | CN | OCH₃ | OH |
| 10.242 | CN | OCH₃ | OCH₃ |
| 10.243 | CN | OCH₃ | OC₂H₅ |
| 10.244 | CN | OCH₃ | O(nC₃H₇) |
| 10.245 | CN | OCH₃ | O(iC₃H₇) |
| 10.246 | CN | OCH₃ | O(nC₄H₉) |
| 10.247 | CN | OCH₃ | O(tC₄H₉) |
| 10.248 | CN | OCH₃ | OPh |
| 10.249 | CN | OCH₃ | SH |
| 10.250 | CN | OCH₃ | SCH₃ |
| 10.251 | CN | OCH₃ | SC₂H₅ |
| 10.252 | CN | OCH₃ | S(nC₃H₇) |
| 10.253 | CN | OCH₃ | S(iC₃H₇) |
| 10.254 | CN | OCH₃ | S(nC₄H₉) |
| 10.255 | CN | OCH₃ | S(tC₄H₉) |
| 10.256 | CN | OCH₃ | SPh |
| 10.257 | CN | OCH₃ | CCl₃ |
| 10.258 | CN | OCH₃ | CH₂F |
| 10.259 | CN | OCH₃ | CHF₂ |
| 10.260 | CN | OCH₃ | CF₃ |
| 10.261 | CN | OCH₃ | CF₂CHF₂ |
| 10.262 | CN | OCH₃ | SO₃H |
| 10.263 | CN | OCH₃ | SO₂CH₃ |
| 10.264 | CN | OCH₃ | SO₂C₂H₅ |
| 10.265 | CN | OCH₃ | SO₂(nC₃H₇) |
| 10.266 | CN | OCH₃ | SO₂(iC₃H₇) |
| 10.267 | CN | OCH₃ | SO₂(nC₄H₉) |
| 10.268 | CN | OCH₃ | SO₂(tC₄H₉) |
| 10.269 | CN | OCH₃ | SO₂Ph |
| 10.270 | CN | OCH₃ | NH₂ |
| 10.271 | CN | OCH₃ | NHCH₃ |
| 10.272 | CN | OCH₃ | NCH₃Ph |
| 10.273 | CN | OCH₃ | N(CH₃)₂ |
| 10.274 | CN | OCH₃ | NPh₂ |
| 10.275 | CN | OCH₃ | CN |
| 10.276 | CN | OCH₃ | NO₂ |

SYNTHESIS EXAMPLES

Example 1

Synthesis of 4-(2'-sulfonylmethyl-41-trifluoromethylbenzoyl)-5-cyclopropylisothiazole 7.214

The following operations are carried out with the exclusion of moisture. To 60 ml of a 1.4 M solution of (0.08 mol) of methylmagnesium bromide in toluene/tetrahydrofuran 3:1 (v/v) there are added 9.0 g (0.04 mol) of 4-iodo-5-cyclopropylisothiazole in 200 ml of tetrahydrofuran with ice-cooling in such a way that the reaction temperature does not exceed 5° C. The reaction mixture is treated with a solution of 20.4 g (0.08 mol) of 2-sulfonylmethyl-4-trifluoromethylbenzoyl chloride in 300 ml of tetrahydrofuran. After the exothermic reaction has subsided, residues of organometallic compounds are hydrolyzed with 100 ml of 10% strength hydrochloric acid. The reaction mixture is taken up in diethyl ether, worked up with water, dried with sodium sulfate, filtered and freed from solvent in vacuo. The crude product is purified on 250 g of silica gel using cyclohexane/ethyl acetate mixtures 10:1 to 4:1 (v/v). Yield 7.2 g (43%) of colorless amorphous solid, 270 MHz $^1$H NMR (CDCl₃), δ [ppm]: 1.0 (m, 2H), 1.3 (m, 2H), 2.8 (m, 1H), 3.4 (s, 3H), 7.2 (d, 1H), 8.0 (d, 1H), 8.3 (s, 1H), 8.4 (s, 1H).

Other active ingredients of the general formula 1 have been obtained analogously by reacting the haloisothiazole compounds of the general formula 3 with carboxylic acid derivatives of the general formula 4 using the protocol described in Example 1. The resulting active ingredients of the general formula 1 are compiled in Table 5.

TABLE 5

| No. | R² | R⁴ | R⁵ | R⁶ | 270 MHz ¹H NMR(CDCl₃), δ[ppm] |
|---|---|---|---|---|---|
| 7.80 | cyclopropyl | Cl | H | SO₂CH₃ | 1.0(m, 2H), 1.4(m, 2H), 2.9(m, 1H), 3.2(s, 3H), 7.7(d, 1H), 8.0(d, 1H), 8.1(s, 1H), 8.3(s, 1H) |
| 11 | cyclopropyl | Cl | OC₂H₅ | SO₂C₂H₅ | 0.9(m, 2H), 1.3(t, 3H), 1.4(m, 2H), 1.6(t, 3H), 3.0 (m, 1H), 3.5(q, 2H), 4.4(q, 2H), 7.3(d, 1H), 8.0 (d, 1H), 8.3(s, 1H) |
| 12 | CH₃ | Cl | H | SO₂CH₃ | 2.9(s, 3H), 3.2(s, 3H), 7.6(d, 1H), 8.0(d, 1H), 8.1 (s, 1H), 8.3(s, 1H) |
| 13 | CH₃ | F | H | F | 2.8(s, 3H), 7.0(m, 1H), 7.7(q, 1H), 8.5(s, 1H) |
| 14 | CH₃ | F | H | CF₃ | 2.9(s, 3H), 7.5(d, 1H), 7.6(d, 1H), 7.7(t, 1H), 8.5 (s, 1H) |
| 15 | CH₃ | H | CF₃ | H | 2.8(s, 3H), 7.7(t, 1H), 7.9(d, 1H), 8.0(d, 1H), 8.1 (s, 1H), 8.6(s, 1H) |
| 16 | iC₃H₇ | Cl | H | SO₂CH₃ | 1.5(d, 6H), 3.2(s, 3H), 4.1 (m, 1H), 7.6(d, 1H), 8.0 (d, 1H), 8.1(s, 1H), 8.3(s, 1H) |
| 9.80 | tC₄H₉ | Cl | H | SO₂CH₃ | 1.7(s, 9H), 3.2(s, 3H), 7.7(d, 1H), 8.0(d, 1H), 8.1 (s, 1H), 8.3(s, 1H) |
| 9.214 | tC₄H₉ | SO₂CH₃ | H | CF₃ | 1.6(s, 9H), 3.4(s, 3H), 7.6(d, 1H), 8.0(d, 1H), 8.2 (s, 1H), 8.5(s, 1H) |
| 17 | phenyl | Cl | OC₂H₅ | SO₂C₂H₅ | 1.2(t, 3H), 1.5(t, 3H), 3.5(q, 2H), 4.1(q, 2H), 7.2 (d, 1H), 7.3(m, 5H), 7.8(d, 1H), 8.9(s, 1H) |

TABLE 6

| No. | Formula | Physical Data |
|---|---|---|
| 6.1 | | IR-Wave numbers in cm⁻¹: 1660, 1511, 1325, 1251, 1202, 1169, 1129, 1072, 796, 699<br>1H-NMR(270 MHz; CDCl₃; in ppm): 0.9(d2H); 1.3(d, 2H); 2.7(m, 1H); 7.65(t, 1H); 7.85(d, 1H); 8.0(d1H); 8.1(s, 1H); 8.45(s, 1H) |
| 6.2 | | IR-Wave numbers in cm⁻¹: 1664, 1585, 1506, 1429, 1375, 1338, 1264, 1245, 857, 800<br>1H-NMR(270 MHz; CDCl₃; in ppm): 0.9(m, 2H); 1.3(m, 2H); 2.85(m, 1H); 7.35(s, 2H); 7.45(s, 1H); 8.3(s1, H) |
| 6.3 | | IR-Wave numbers in cm⁻¹: 1659, 1612, 1499, 1428, 1339, 1270, 1143, 1103, 973, 847<br>1H-NMR(270 MHz; CDCl₃; in ppm): 0.9(m, 2H); 1.3(d, 2H); 2.8(m, 1H); 7.0(m, 2H); 7.65(d, 1H); 8.4(s1, H) |

TABLE 6-continued

| No. | Formula | Physical Data |
|---|---|---|
| 6.4 | | IR-Wave numbers in cm$^{-1}$:<br>1662, 1508, 1425, 1330, 1215, 1176, 1135, 1077, 913, 835<br>1H-NMR(270 MHz; CDCl$_3$; in ppm):<br>0.9(m, 2H); 1.4(m, 2H); 2.9(m, 1H); 7.45(d, 1H); 7.55(d, 1H); 7.7(t, 1H)8.4 (s, 1H) |
| 6.5 | | IR-Wave numbers in cm$^{-1}$:<br>1664, 1525, 1507, 1350, 1340, 1263, 1246, 893, 835, 737<br>1H-NMR(270 MHz; CDCl$_3$; in ppm):<br>0.9(m, 2H); 1.3(m, 2H); 2.9(m, 2H); 7.6(d, 1H); 8.2(m, 2H); 8.35(s, 1H) |
| 6.6 | | IR-Wave numbers in cm$^{-1}$:<br>1666, 1528, 1508, 1430, 1383, 1340, 1279, 1262, 853, 816<br>1H-NMR(270 MHz; CDCl$_3$; in ppm):<br>0.9(m, 2H); 1.3(m, 2H); 2.6(s, 3H); 2.9(m, 1H); 7.4(d, 1H); 7.8(d, 1H); 8.25(s, 1H) |
| 6.7 | | 1H-NMR(270 MHz; CDCl$_3$; in ppm):<br>0.9(m, 2H); 1.3(m, 2H); 2.8(m, 1H); 7.15 (m, 1H); 7.65(d, 1H); 7.75(d, 1H) 8.65(s, 1H) |
| 6.8 | | 1H-NMR(270 MHz; CDCl$_3$; in ppm):<br>0.9(m, 2H); 1.3(m, 2H); 2.8(m, 1H); 3.35 (m, 3H); 7.65(d, 1H); 8.3(s, 1H), 8.55(d, 1H); 9(d1H) |
| 6.9 | | IR-Wave numbers in cm$^{-1}$:<br>1659, 1505, 1458, 1427, 1335, 1260, 1246, 763, 749<br>1H-NMR(270 MHz; CDCl$_3$; in ppm):<br>0.9(m, 2H); 1.3(m, 2H); 2.25(s, 3H); 2.35(s, 3H); 2.85(m, 3H); 7.15(m, 2H); 7.3(m, 3H); 8.3(s, 1H) |

TABLE 6-continued

| No. | Formula | Physical Data |
|---|---|---|
| 6.10 | | IR-Wave numbers in cm$^{-1}$:<br>1661, 1505, 1450, 1395, 1309, 1256, 1192, 1130, 965, 811<br>1H-NMR(270 MHz; CDCl$_3$; in ppm):<br>0.9(m, 2H); 1.3(m, 2H); 2.35(s, 3H); 2.9(m, 1H); 3.25(s, 3H); 4.0(s, 3H)7.25 (d, 1H); 7.9(d, 1H)8.2(s, 1H) |
| 6.11 | | IR-Wave numbers in cm$^{-1}$:<br>1649, 1602, 1586, 1502, 1489, 1280, 1245, 1164, 873<br>1H-NMR(270 MHz; CDCl$_3$; in ppm):<br>0.9(m, 2H); 1.3(m, 2H); 2.7(m, 1H); 7.15(m, 5H); 7.35(m, 2H); 7.8(d, 1H); 8.0 (d, 1H); 8.5(s, 1H) |
| 6.12 | | IR-Wave numbers in cm$^{-1}$:<br>1666, 1578, 1508, 1429, 1382, 1338, 1272, 1084, 988, 812<br>1H-NMR(270 MHz; CDCl$_3$; in ppm):<br>0.9(m, 2H); 1.3(m, 2H); 2.5(s, 3H); 2.85(m, 1H); 7.15(d, 1H); 7.4(d, 1H), 8.3 (s1H); |
| 6.13 | | IR-Wave numbers in cm$^{-1}$:<br>1662, 1590, 1527, 1506, 1453, 1429, 1356, 1339, 1258, 818<br>1H-NMR(270 MHz; CDCl$_3$; in ppm):<br>0.9(m, 2H); 1.4(m, 2H); 2.35(s, 3H); 2.85(m, 1H); 3.95(s, 3H); 7.2(d, 1H); 7.7 (d, 1H); 8.3(s, 1H); |
| 6.14 | | IR-Wave numbers in cm$^{-1}$:<br>1666, 1506, 1430, 1359, 1322, 1259, 1162, 1138, 804, 736<br>1H-NMR(270 MHz; CDCl$_3$; in ppm):<br>0.9(m, 2H); 1.25(m, 2H); 2.6(m, 1H); 3.9(s, 3H); 7.0(d, 2H); 7.85(d, 2H); 8.45(s, 1H) |

The compounds I and their salts which can be used in agriculture are suitable as herbicides, both as isomer mixtures and in the form of the pure isomers. The herbicidal compositions comprising I are highly capable of controlling vegetation on non-crop areas, especially at high rates of application. In crops such as wheat, rice, maize, soybeans and cotton, they act against broad-leaved weeds and grass weeds without damaging the crop plants to a considerable extent. This effect is observed mainly at low rates of application.

Depending on the application method in question, the compounds I or compositions comprising them can additionally be used in a large number of other crop plants for eliminating undesirable plants. Suitable crops are, for example, the following:

*Allium cepa, Ananas comosus, Arachis hypogaea, Asparagus officinalis, Beta vulgaris* ssp. *altissima, Beta vulagris* spp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max,* (*Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum*

*usitatissimum, Lycopersicon lycopersicum,* Malus spp., *Manihot esculenta, Medicago sativa,* Musa spp., *Nicotiana tabacum (N.rustica), Olea europaea, Oryza sativa, Phaseolus lunatus, Phaseolus vulgaris, Picea abies,* Pinus spp., *Pisum sativum, Prunus avium, Prunus persica, Pyrus communis, Ribes sylestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera, Zea mays.*

In addition, the compounds I can also be used in crops which tolerate the action of herbicides as a result of breeding, including genetic engineering methods.

Application of the herbicidal compositions, or of the active ingredients, can be effected pre- or post-emergence. If the active ingredients are less well compatible with certain crop plants, application techniques may be used in which the herbicidal compositions are sprayed, with the aid of the spraying equipment, in such a way that they come into as little contact as possible with the leaves of the sensitive crop plants while the active compounds reach the leaves of undesirable plants growing underneath, or the bare soil surface (post-directed, lay-by).

The compounds I, or the herbicidal compositions comprising them, can be applied for example in the form of directly sprayable aqueous solutions, powders, suspensions, also highly concentrated aqueous, oily or other suspensions or dispersions, emulsions, oil dispersions, pastes, dusts, materials for spreading, or granules, by means of spraying, atomizing, dusting, spreading or pouring. The use forms depend on the intended purposes; in any case, they should guarantee the finest possible distribution of the active ingredients according to the invention.

Suitable inert additives are essentially: mineral oil fractions of medium to high boiling point such as kerosene or diesel oil, furthermore coal tar oils and oils of vegetable or animal origin, aliphatic, cyclic and aromatic hydrocarbons, eg. paraffin, tetrahydronaphthalene, alkylated naphthalenes or their derivatives, alkylated benzenes or their derivatives, alcohols such as methanol, ethanol, propanol, butanol, cyclohexanol, ketones such as cyclohexanone, or strongly polar solvents, eg. amines such as N-methylpyrrolidone or water.

Aqueous use forms can be prepared from emulsion concentrates, suspensions, pastes, wettable powders or water-dispersible granules by adding water. To prepare emulsions, pastes or oil dispersions, the substances, as such or dissolved in an oil or solvent, can be homogenized in water by means of a wetting agent, tackifier, dispersant or emulsifier. Alternatively, it is possible to prepare concentrates comprising active substance, wetting agent, tackifier, dispersant or emulsifier and, if desired, solvent or oil, which are suitable for dilution with water.

Suitable surfactants (adjuvants) are the alkali metal salts, alkaline earth metal salts and ammonium salts of aromatic sulfonic acids, eg. ligno-, phenol-, naphthalene- and dibutylnaphthalenesulfonic acid, and of fatty acids, of alkyl- and alkylarylsulfonates, of alkyl lauryl ether sulfates and of fatty alcohol sulfates, salts of sulfated hexa-, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenyl ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or grinding the active substances together with a solid carrier.

Granules, eg. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nutshell meal, cellulose powders or other solid carriers.

The concentrations of the active ingredients I in the ready-to-use preparations can be varied within wide limits. In general, the formulations comprise from 0.001 to 98% by weight, preferably 0.01 to 95% by weight, of active ingredient. The active ingredients are employed in a purity of from 90% to 100%, preferably 95% to 100% (according to NMR spectrum).

For example, Compound 11 according to the invention can be formulated as follows:

I. 20 parts by weight of Compound No. 11 are dissolved in a mixture composed of 80 parts by weight of alkylated benzene, 10 parts by weight of the adduct of 8 to 10 mol of ethylene oxide and 1 mol of oleic acid N-monoethanolamide, 5 parts by weight of calcium dodecylbenzenesulfonate and 5 parts by weight of the adduct of 40 mol of ethylene oxide and 1 mol of castor oil. Pouring the solution into 100,000 parts by weight of water and finely distributing it therein gives an aqueous dispersion comprising 0.02% by weight of the active ingredient.

II. 20 parts by weight of Compound 11 are dissolved in a mixture composed of 40 parts by weight of cyclohexanone, 30 parts by weight of isobutanol, 20 parts by weight of the adduct of 40 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion comprising 0.02% by weight of the active ingredient.

III. 20 parts by weight of Active Ingredient 11 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide and 1 mol of castor oil. Pouring the solution into 100,000 parts by weight of water and finely distributing it therein gives an aqueous dispersion comprising 0.02% by weight of the active ingredient.

IV. 20 parts by weight of Active Ingredient 11 are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

V. 3 parts by weight of Active Ingredient 11 are mixed with 97 parts by weight of finely divided kaolin. This gives a dust which comprises 3% by weight of the active ingredient.

VI. 20 parts by weight of Active Ingredient 11 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of Compound 11 is dissolved in a mixture comprising 70 parts by weight of cyclohexanone, 20 parts by weight of ethoxylated isooctylphenol and 10 parts by weight of ethoxylated castor oil. This gives a stable emulsion concentrate.

VIII. 1 part by weight of Compound 11 is dissolved in a mixture composed of 80 parts by weight of cyclohexanone and 20 parts by weight of Emulphor EL (ethoxylated castor oil). This gives a stable emulsion concentrate.

To widen the spectrum of action and to achieve synergistic effects, the benzoylisothiazoles I can be mixed with a large number of representatives of other groups of herbicidally or growth-regulatory active ingredients and applied concomitantly. Components in mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-aroyl-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ether, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- or hetaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides, uracils.

It may furthermore be advantageous to apply the compounds I, alone or in combination with other herbicides, as a mixture with further crop protection agents, for example with pesticides or agents for controlling phytopathogenic fungi or bacteria. Also of interest is the miscibility with mineral salt solutions which are employed for treating nutritional and trace element deficiencies. Non-phytotoxic oils and oil concentrates may also be added.

The rates of application of active ingredient are from 0.001 to 3.0, preferably 0.01 to 1.0, kg/ha of active substance (a. S.) depending on the control target, the season, target plants and the growth stage.

USE EXAMPLES

The herbicidal activity of the benzoylisothiazoles of the formula I was demonstrated by greenhouse experiments:

The culture containers used were plastic flowerpots containing loamy sand with approximately 3.0% of humus as substrate. The seeds of the test plants were sown separately for each species.

In the pre-emergence treatment, the active ingredients, which were suspended or emulsified in water, were applied directly after sowing by means of finely distributing nozzles. The containers were irrigated slightly to promote germination and growth and subsequently covered with translucent plastic shrouds until the plants had rooted. This cover caused uniform germination of the test plants unless this was adversely affected by the active ingredients.

To carry out the post-emergence treatment, the test plants were first grown to a plant height of 3 to 15 cm, depending on the plant habit, and only then treated with the active ingredients which had been suspended or emulsified in water. For this purpose, the test plants are either sown directly and grown in the same containers, or they are first grown separately as seedlings and transplanted into the test containers a few days prior to treatment.

The rate of application for the post-emergence treatment was 0.5, or 0.25, kg/ha of a.s.

Depending on the species, the plants were kept at 10–25° C. or 20–35° C. The test period extended over 2 to 4 weeks. During this time, the plants were tended, and their response to the individual treatments was evaluated.

Evaluation was carried out using a scale of from 0 to 100. 100 means no emergence of the plants, or complete destruction of at least the aerial parts, and 0 means no damage, or normal course of growth.

The plants used in the greenhouse experiments belonged to the following species:

| Scientific Name | Common Name |
| --- | --- |
| Triticum aestivum | wheat |
| Abutilon theophrasti | velvetleaf |
| Chenopodium album | lamsbquarters (goosefoot) |
| Solanum nigrum | black nightshade |

TABLE 6

Selective herbicidal activity when applied post-emergence in the greenhouse

11

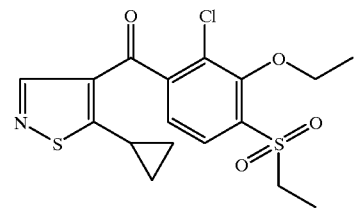

| | Rate of application (kg/ha of a.s.) | |
| --- | --- | --- |
| | 0.5 | 0.25 |
| Test plants | Damage in % | |
| TRZAW | 0 | 0 |
| ABUTH | 80 | 80 |
| CHEAL | 90 | 90 |
| SOLNI | 90 | 80 |

We claim:
1. A 4-benzoylisothiazole of the formula 1

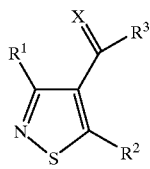

where the substituents have the following meanings:
X is oxygen or sulfur;
$R^1$ is hydrogen, alkyl, alkenyl, alkynyl; unsubstituted or substituted alkoxycarbonyl;
  unsubstituted or substituted aryl, unsubstituted or substituted heterocyclyl or unsubstituted or substituted hetaryl;
$R^2$ is hydrogen, alkyl, alkenyl, alkynyl, cycloalkyl or cycloalkenyl, it being possible for these radicals to have attached to them one or more of the following groups: halogen, alkyl, alkenyl or alkynyl;
  aryl, it being possible for this radical to have attached to it one or more of the following groups: alkyl, alkenyl, alkynyl, alkoxy, alkenyloxy, alkynyloxy, alkylthio or alkenylthio, it being possible for these radicals to be partially or fully halogenated or to have attached to them one or more of the following groups: alkoxy, alkenyloxy, aryloxy, alkylsulfonyl, alkenylsulfonyl or arylsulfonyl;
  alkylsulfonyl or alkoxycarbonyl;
  unsubstituted or substituted aryloxy or unsubstituted or substituted arylthio;
  unsubstituted or substituted mono- or dialkylamino, unsubstituted or substituted mono- or diarylamino or unsubstituted or substituted N-alkyl-N-arylamino, it being possible for alkyl and aryl to be identical or different;
  halogen, cyano or nitro;
  hetaryl or heterocyclyl, it being possible for these radicals to be partially or fully halogenated or to have attached to them one or more of the following groups: alkyl, alkoxy or aryl, it being possible in the case of heterocyclyl for a nitrogen ring member to have attached to it one of the following groups: alkyl, alkenyl, alkynyl, cycloalkyl, haloalkyl, alkoxy, alkenyloxy, alkynyloxy, cycloalkoxy, haloalkoxy, unsubstituted or substituted aryl or unsubstituted or substituted aryloxy;
$R^3$ is a radical of the formula 2

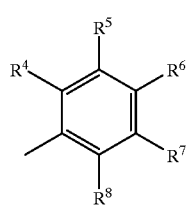

where the substituents have the following meanings:
$R^4$–$R^8$ are identical or different and independently of one another are hydrogen, alkyl, alkenyl, alkynyl, cycloalkyl, cycloalkenyl, cycloalkylalkyl, cycloalkylalkenyl, cycloalkylalkynyl, aryl, arylalkyl, arylalkenyl, arylalkynyl, hydroxyl, alkoxy, alkenyloxy, alkynyloxy, cycloalkoxy, cycloalkylalkoxy, cycloalkylalkenyloxy, cycloalkylalkynyloxy, cycloalkenyloxy, aryloxy, arylalkoxy, arylalkenyloxy, arylalkynyloxy, thio, alkylthio, alkenylthio, alkynylthio, cycloalkylthio, cycloalkylalkylthio, cycloalkylalkenylthio, cycloalkylalkynylthio, cycloalkenylthio, arylthio, arylalkylthio, arylalkenylthio, arylalkynylthio, amino, unsubstituted or substituted mono- or dialkylamino, unsubstituted or substituted mono- or diarylamino, unsubstituted or substituted N-alkyl-N-arylamino, it being possible for alkyl and aryl to be identical or different, alkenylamino, alkynylamino, cycloalkylamino, cycloalkenylamino, sulfonyl, alkylsulfonyl, alkenylsulfonyl, alkynylsulfonyl, cycloalkylsulfonyl, cycloalkylalkylsulfonyl, cycloalkylalkenylsulfonyl, cycloalkylalkynylsulfonyl, arylsulfonyl, arylalkylsulfonyl, arylalkenylsulfonyl, arylalkynylsulfonyl, sulfoxyl, alkylsulfoxyl, alkenylsulfoxyl, alkynylsulfoxyl, cycloalkylsulfoxyl, cycloalkylalkylsulfoxyl, cycloalkylalkenylsulfoxyl, cycloalkylalkynylsulfoxyl, arylsulfoxyl, arylalkylsulfoxyl, arylalkenylsulfoxyl, arylalkynylsulfoxyl, aminosulfonyl, unsubstituted or substituted mono- or dialkylaminosulfonyl, unsubstituted or substituted diarylaminosulfonyl, unsubstituted or substituted N-alkyl-N-arylaminosulfonyl, it being possible for alkyl and aryl to be identical or different, alkylcarbonyl, alkenylcarbonyl, alkynylcarbonyl, cycloalkylcarbonyl, cycloalkylalkylcarbonyl, cycloalkylalkenylcarbonyl, cycloalkylalkynylcarbonyl, arylcarbonyl, arylalkylcarbonyl, arylalkenylcarbonyl, arylalkynylcarbonyl, carboxyl, alkoxycarbonyl, alkenyloxycarbonyl, alkynyloxycarbonyl, cycloalkoxycarbonyl, cycloalkylalkoxycarbonyl, cycloalkylalkenyloxycarbonyl, cycloalkylalkynyloxycarbonyl, aryloxycarbonyl, arylalkoxycarbonyl, arylalkenyloxycarbonyl, arylalkynyloxycarbonyl, aminocarbonyl, unsubstituted or substituted mono- or dialkylaminocarbonyl, unsubstituted or substituted mono- or diarylaminocarbonyl, unsubstituted or substituted N-alkyl-N-arylaminocarbonyl, it being possible for alkyl and aryl to be identical or different, unsubstituted or substituted mono- or dialkylcarbonylamino, unsubstituted or substituted mono- or diarylcarbonylamino, unsubstituted or substituted N-alkyl-N-arylcarbonylamino, it being possible for alkyl and aryl to be identical or different; alkoxyaminocarbonyl, alkenyloxyaminocarbonyl, alkynyloxycarbonylamino, cycloalkoxycarbonylamino, cycloalkylalkoxycarbonylamino, cycloalkylalkenyloxycarbonylamino, cycloalkylalkynyloxycarbonylamino, aryloxycarbonylamino, arylalkoxycarbonylamino, arylalkenyloxycarbonylamino, arylalkynyloxycarbonylamino, halogen, haloalkyl, haloalkenyl, haloalkynyl, haloalkoxy, haloalkenyloxy, haloalkynyloxy, haloalkylthio, haloalkenylthio, haloalkynylthio, haloalkylamino, haloalkenylamino, haloalkynylamino, haloalkylsulfonyl, haloalkenylsulfonyl, haloalkynylsulfonyl, haloalkylsulfoxyl, haloalkenylsulfoxyl, haloalkynylsulfoxyl, haloalkylcarbonyl, haloalkenylcarbonyl, haloalkynylcarbonyl, haloalkoxycarbonyl, haloalkenyloxycarbonyl, haloalkynyloxycarbonyl, haloalkylaminocarbonyl, haloalkenylaminocarbonyl, haloalkynylaminocarbonyl, haloalkoxycarbonylamino, haloalkenyloxycarbonylamino, haloalkynyloxycarbonylamino; cyano or nitro or one of the following groups:

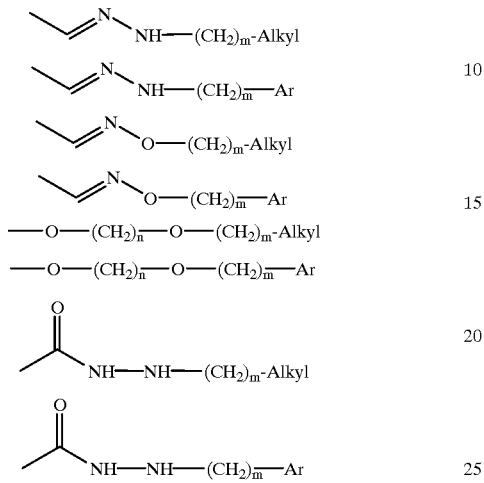

$n = 1,2,3;$
$m = 0,1,2,3$ or $R^4, R^5$ together form a five- or six-membered, saturated or unsaturated, aromatic or non-aromatic, unsubstituted or substituted alkylene, alkenylene or alkdienylene chain; or $R^5, R^6$ together form a five- or six-membered, saturated or unsaturated, aromatic or non-aromatic, unsubstituted or substituted alkylene, alkenylene or alkdienylene chain;

with the exception of 4-benzoyl-3-phenylisothiazole, 4-(4'-chlorobenzoyl)-3-methylisothiazole, 4-benzoyl-3,5-dimethylisothiazole, 4-(4'-hydroxymethylcarbonylaminobenzoyl)-isothiazole and 4-(3',5'-tertiary-butyl-4'-hydroxybenzoyl)-isothiazole;

or a salt of the 4-benzoylisothiazole of the formula 1 which is conventionally used in agriculture.

2. The 4-benzoylisothiazole of the formula 1 defined in claim 1 where X is oxygen.

3. The 4-benzoylisothiazole of the formula 1 defined in claim 1 where $R^1$ is hydrogen or unsubstituted or substituted alkoxycarbonyl.

4. The 4-benzoylisothiazole of the formula 1 defined in claim 1 where $R^2$ is alkyl, cycloalkyl, aryl which is unsubstituted or mono- or polysubstituted by halogen or haloalkyl, or hetaryl which is unsubstituted or mono- or polysubstituted by halogen.

5. The 4-benzoylisothiazole of the formula 1 defined in claim 1 where $R^2$ is methyl, ethyl, isopropyl, tert-butyl, cyclopropyl, 1-methylcyclopropyl, 3-trifluoromethylaryl, 2,4-difluoroaryl, 1,3-benzodioxolyl, 2,2-difluoro-1,3-benzodioxolyl, 1,3-benzoxathiolyl, 3,3-dioxo-1,3-benzoxathiolyl, benzoxazolyl, pyrazolyl or thienyl.

6. The 4-benzoylisothiazole of the formula 1 defined in claim 1 where $R^4$–$R^8$ are identical or different and independently of one another are hydrogen, alkyl, cycloalkyl, aryl, hydroxyl, alkoxy, cycloalkoxy, aryloxy, thio, alkylthio, cycloalkylthio, arylthio, amino, in each case unsubstituted or substituted mono- or dialkylamino or mono- or diarylamino or N-alkyl-N-arylamino, it being possible for alkyl and aryl to be identical or different, cycloalkylamino, sulfonyl, alkylsulfonyl, cycloalkylsulfonyl, arylsulfonyl, sulfoxyl, alkylsulfoxyl, cycloalkylsulfoxyl, arylsulfoxyl, alkylcarbonyl, cycloalkylcarbonyl, arylcarbonyl, carboxyl, alkoxycarbonyl, cycloalkoxycarbonyl, aryloxycarbonyl, aminocarbonyl, in each case unsubstituted or substituted mono- or dialkylaminocarbonyl or mono- or diarylaminocarbonyl or N-alkyl-N-arylaminocarbonyl, it being possible for alkyl and aryl to be identical or different, alkoxyaminocarbonyl, cycloalkoxycarbonylamino, aryloxycarbonylamino, halogen, haloalkyl, haloalkoxy, haloalkylthio, haloalkylamino, haloalkylsulfonyl, haloalkylsulfoxyl, haloalkylcarbonyl, haloalkoxycarbonyl, haloalkylaminocarbonyl, haloalkoxycarbonylamino; cyano or nitro; or $R^4, R^5$ together form a five- or six-membered, saturated or unsaturated, aromatic or non-aromatic, unsubstituted or substituted alkylene, alkenylene or alkdienylene chain; or $R^5, R^6$ together form a five- or six-membered, saturated or unsaturated, aromatic or non-aromatic, unsubstituted or substituted alkylene, alkenylene or alkdienylene chain.

7. The 4-benzoylisothiazole of the formula 1 defined in claim 1 where $R^3$ is a radical of the formula 2a–g

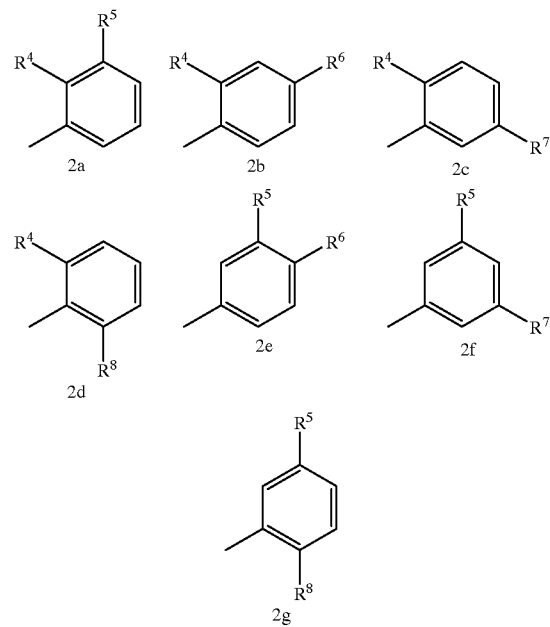

where the substituents have the following meanings:

$R^4$–$R^8$ are identical or different and independently of one another are alkyl, alkenyl, alkynyl, cycloalkyl, cycloalkylalkyl, cycloalkylalkenyl, cycloalkylalkynyl, aryl, arylalkyl, arylalkenyl, arylalkynyl, hydroxyl, alkoxy, alkenyloxy, alkynyloxy, cycloalkoxy, cycloalkylalkoxy, cycloalkylalkenyloxy, cycloalkylalkynyloxy, aryloxy, arylalkoxy, arylalkenyloxy, arylalkynyloxy, thio, alkylthio, alkenylthio, alkynylthio, cycloalkylthio, cycloalkylalkylthio, cycloalkylalkenylthio, cycloalkylalkynylthio, arylthio, arylalkylthio, arylalkenylthio, arylalkynylthio, amino, unsubstituted or substituted mono- or dialkylamino, unsubstituted or substituted mono- or diarylamino, unsubstituted or substituted N-alkyl-N-arylamino, it being possible for alkyl and aryl to be identical or different, sulfonyl, alkylsulfonyl, cycloalkylsulfonyl, cycloalkylalkylsulfonyl, cycloalkylalkenylsulfonyl, cycloalkylalkynylsulfonyl, arylsulfonyl, arylalkylsulfonyl, arylalkenylsulfonyl, arylalkynylsulfonyl, sulfoxyl, alkylsulfoxyl, alkenylsulfoxyl, alkynylsulfoxyl, cycloalkylsulfoxyl, cycloalkylalkylsulfoxyl, cycloalkylalkenylsulfoxyl, cycloalkylalkynylsulfoxyl, arylsulfoxyl, arylalkylsulfoxyl, arylalkenylsulfoxyl, arylalkynylsulfoxyl, aminosulfonyl, unsubstituted or substituted mono- or dialkylaminosulfonyl, unsubstituted or substituted diarylaminosulfonyl, unsubstituted or substituted N-alkyl-N-arylaminosulfonyl, it being possible for alkyl and aryl to be identical or different, alkylcarbonyl, alkenylcarbonyl, alkynylcarbonyl, cycloalkylcarbonyl, cycloalkylalkylcarbonyl, cycloalkylalkenylcarbonyl, cycloalkylalkynylcarbonyl, arylcarbonyl, arylalkylcarbonyl, arylalkenylcarbonyl, arylalkynylcarbonyl, carboxyl, alkoxycarbonyl, alkenyloxycarbonyl, alkynyloxycarbonyl, cycloalkoxycarbonyl, cycloalkylalkoxycarbonyl, cycloalkylalkenyloxycarbonyl, cycloalkylalkynyloxycarbonyl, aryloxycarbonyl, arylalkoxycarbonyl, arylalkenyloxycarbonyl, arylalkynyloxycarbonyl, aminocarbonyl, unsubstituted or substituted mono- or dialkylaminocarbonyl, unsubstituted or substituted mono- or diarylaminocarbonyl, unsubstituted or substituted N-alkyl-N-arylaminocarbonyl, it being possible for alkyl and aryl to be identical or different, unsubstituted or substituted mono- or dialkylcarbonylamino, unsubstituted or substituted mono- or diarylcarbonylamino, unsubstituted or substituted N-alkyl-N-arylcarbonylamino, it being possible for alkyl and aryl to be identical or different; alkoxyaminocarbonyl, alkenyloxyaminocarbonyl, alkynyloxycarbonylamino, cycloalkoxycarbonylamino, cycloalkylalkoxycarbonylamino, cycloalkylalkenyloxycarbonylamino, cycloalkylalkynyloxycarbonylamino, aryloxycarbonylamino, arylalkoxycarbonylamino, arylalkenyloxycarbonylamino, arylalkynyloxycarbonylamino, halogen, haloalkyl, haloalkenyl, haloalkynyl, haloalkoxy, haloalkenyloxy, haloalkynyloxy, haloalkylthio, haloalkenylthio, haloalkynylthio, haloalkylamino, haloalkenylamino, haloalkynylamino, haloalkylsulfonyl, haloalkenylsulfonyl, haloalkynylsulfonyl, haloalkylcarbonyl, haloalkenylcarbonyl, haloalkynylcarbonyl, haloalkoxycarbonyl, haloalkenyloxycarbonyl, haloalkynyloxycarbonyl, haloalkylaminocarbonyl, haloalkenylaminocarbonyl, haloalkynylaminocarbonyl, haloalkoxycarbonylamino, haloalkenyloxycarbonylamino, haloalkynyloxycarbonylamino; cyano or nitro.

8. The 4-benzoylisothiazole of the formula 1 defined in claim 1 where $R^3$ is a radical of the formula 2h–l

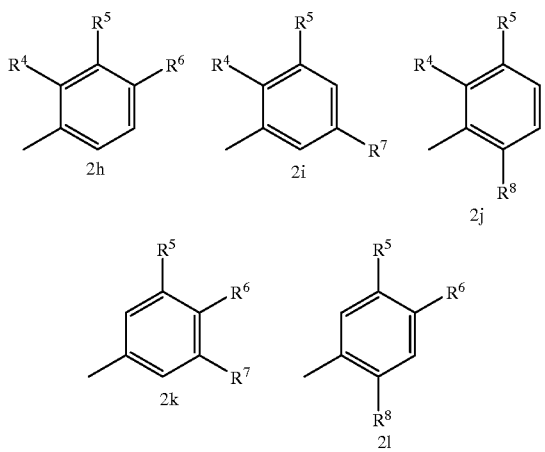

where the substituents have the following meanings:
$R^4$–$R^8$ are identical or different and independently of one another are a low-molecular radical selected from the group consisting of alkyl, alkenyl, alkynyl, cycloalkyl, cycloalkylalkyl, cycloalkylalkenyl, cycloalkylalkynyl, aryl, arylalkyl, arylalkenyl, arylalkynyl, hydroxyl, alkoxy, alkenyloxy, alkynyloxy, cycloalkoxy, cycloalkylalkoxy, cycloalkylalkenyloxy, cycloalkylalkynyloxy, aryloxy, arylalkoxy, arylalkenyloxy, arylalkynyloxy, thio, alkylthio, alkenylthio, alkynylthio, cycloalkylthio, cycloalkylalkylthio, cycloalkylalkenylthio, cycloalkylalkynylthio, arylthio, arylalkylthio, arylalkenylthio, arylalkynylthio, amino, unsubstituted or substituted mono- or dialkylamino, unsubstituted or substituted mono- or diarylamino, unsubstituted or substituted N-alkyl-N-arylamino, it being possible for alkyl and aryl to be identical or different, sulfonyl, alkylsulfonyl, cycloalkylsulfonyl, cycloalkylalkylsulfonyl, cycloalkylalkenylsulfonyl, cycloalkylalkynylsulfonyl, arylsulfonyl, arylalkylsulfonyl, arylalkenylsulfonyl, arylalkynylsulfonyl, sulfoxyl, alkylsulfoxyl, alkenylsulfoxyl, alkynylsulfoxyl, cycloalkylsulfoxyl, cycloalkylalkylsulfoxyl, cycloalkylalkenylsulfoxyl, cycloalkylalkynylsulfoxyl, arylsulfoxyl, arylalkylsulfoxyl, arylalkenylsulfoxyl, arylalkynylsulfoxyl, aminosulfonyl, unsubstituted or substituted mono- or dialkylaminosulfonyl, unsubstituted or substituted diarylaminosulfonyl, unsubstituted or substituted N-alkyl-N-arylaminosulfonyl, it being possible for alkyl and aryl to be identical or different, alkylcarbonyl, alkenylcarbonyl, alkynylcarbonyl, cycloalkylcarbonyl, cycloalkylalkylcarbonyl, cycloalkylalkenylcarbonyl, cycloalkylalkynylcarbonyl, arylcarbonyl, arylalkylcarbonyl, arylalkenylcarbonyl, arylalkynylcarbonyl, carboxyl, alkoxycarbonyl, alkenyloxycarbonyl, alkynyloxycarbonyl, cycloalkoxycarbonyl, cycloalkylalkoxycarbonyl, cycloalkylalkenyloxycarbonyl, cycloalkylalkynyloxycarbonyl, aryloxycarbonyl, arylalkoxycarbonyl, arylalkenyloxycarbonyl, arylalkynyloxycarbonyl, aminocarbonyl, unsubstituted or substituted mono- or dialkylaminocarbonyl, unsubstituted or substituted mono- or diarylaminocarbonyl, unsubstituted or substituted N-alkyl-N-arylaminocarbonyl, it being possible for alkyl and aryl to be identical or different, unsubstituted or substituted mono- or dialkylcarbonylamino, unsubstituted or substituted mono- or diarylcarbonylamino, unsubstituted or substituted N-alkyl-N-arylcarbonylamino, it being possible for alkyl and aryl to be identical or different, alkoxyaminocarbonyl, alkenyloxyaminocarbonyl, alkynyloxycarbonylamino, cycloalkoxycarbonylamino, cycloalkylalkoxycarbonylamino, cycloalkylalkenyloxycarbonylamino, cycloalkylalkynyloxycarbonylamino, aryloxycarbonylamino, arylalkoxycarbonylamino, arylalkenyloxycarbonylamino, arylalkynyloxycarbonylamino, halogen, haloalkyl, haloalkenyl, haloalkynyl, haloalkoxy, haloalkenyloxy, haloalkynyloxy, haloalkylthio, haloalkenylthio, haloalkynylthio, haloalkylamino, haloalkenylamino, haloalkynylamino, haloalkylsulfonyl, haloalkenylsulfonyl, haloalkynylsulfonyl, haloalkylcarbonyl, haloalkenylcarbonyl, haloalkynylcarbonyl, haloalkoxycarbonyl, haloalkenyloxycarbonyl, haloalkynyloxycarbonyl, haloalkylaminocarbonyl, haloalkenylaminocarbonyl, haloalkynylaminocarbonyl, haloalkoxycarbonylamino, haloalkenyloxycarbonylamino, haloalkynyloxycarbonylamino; cyano or nitro, or $R^4$, $R^5$ together form a five- or six-membered, saturated or unsaturated, aromatic or non-aromatic, unsubstituted or substituted alkylene, alkenylene or alkdienylene chain; or $R^5$, $R^6$ together form a five- or six-membered, saturated or unsaturated, aromatic or non-aromatic, unsubstituted or substituted alkylene, alkenylene or alkdienylene chain.

9. The 4-benzoylisothiazole of the formula 1 defined in claim 1 where $R^3$ is a radical of the formula 2b

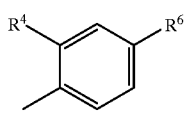

2b and $R^4$ and $R^6$ are identical or different and independently of one another are alkyl, alkoxy, aryloxy, alkylsulfonyl, halogen or haloalkyl.

10. The 4-benzoylisothiazole of the formula 1 defined in claim 9 where
$R^4$ and $R^6$ are identical or different and independently of one another are methylsulfonyl, ethylsulfonyl, difluoromethyl, trifluoromethyl, tetrafluoroethyl or trichloromethyl.

11. The 4-benzoylisothiazole of the formula 1 defined in claim 1 where $R^3$ is a radical of the formula 2h

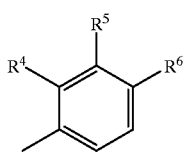

2h and $R^4$, $R^5$ and $R^6$ are identical or different and independently of one another are alkyl, alkoxy, aryloxy, alkylsulfonyl, halogen or haloalkyl.

12. The 4-benzoylisothiazole of the formula 1 defined in claim 11 where
$R^4$, $R^5$ and $R^6$ are identical or different and independently of one another are a low-molecular radical selected from the group consisting of methyl, ethyl, methoxy, ethoxy, phenoxy, methylsulfonyl, ethylsulfonyl, fluorine, bromine, iodine, difluoromethyl, trifluoromethyl, tetrafluoroethyl or trichloromethyl.

13. The 4-benzoylisothiazole of the formula 1 defined in claim 1 where $R^3$ is 2-chloro-4-methylsulfonylphenyl.

14. The 4-benzoylisothiazole of the formula 1 defined in claim 1 where $R^3$ is 2-methylsulfonyl-4-trifluoromethylphenyl.

15. The 4-benzoylisothiazole of the formula 1 defined in claim 1 where $R^3$ is 2-chloro-3-methoxy-4-methylphenyl or 2-chloro-3-ethoxy-4-ethylphenyl.

16. A 4-benzoylisothiazole of the formula 1

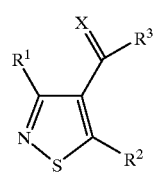

1 where the substituents have the following meanings:

X is oxygen or sulfur;

$R^1$ is hydrogen, alkyl, alkenyl, alkynyl; unsubstituted or substituted alkoxycarbonyl;
unsubstituted or substituted aryl, unsubstituted or substituted heterocyclyl or unsubstituted or substituted hetaryl;

$R^2$ is hydrogen, alkyl, alkenyl, alkynyl, cycloalkyl or cycloalkenyl, it being possible for these radicals to have attached to them one or more of the following groups: halogen, alkyl, alkenyl or alkynyl;
aryl, it being possible for this radical to have attached to it one or more of the following groups: alkyl, alkenyl, alkynyl, alkoxy, alkenyloxy, alkynyloxy, alkylthio or alkenylthio, it being possible for these radicals to be partially or fully halogenated or to have attached to them one or more of the following groups: alkoxy, alkenyloxy, aryloxy, alkylsulfonyl, alkenylsulfonyl or arylsulfonyl;
alkylsulfonyl or alkoxycarbonyl;
unsubstituted or substituted aryloxy or unsubstituted or substituted arylthio;
unsubstituted or substituted mono- or dialkylamino, unsubstituted or substituted mono- or diarylamino or unsubstituted or substituted N-alkyl-N-arylamino, it being possible for alkyl and aryl to be identical or different;
halogen, cyano or nitro;
hetaryl or heterocyclyl, it being possible for these radicals to be partially or fully halogenated or to have attached to them one or more of the following groups: alkyl, alkoxy or aryl, it being possible in the case of heterocyclyl for a nitrogen ring member to have attached to it one of the following groups: alkyl, alkenyl, alkynyl, cycloalkyl, haloalkyl, alkoxy, alkenyloxy, alkynyloxy, cycloalkoxy, haloalkoxy, unsubstituted or substituted aryl or unsubstituted or substituted aryloxy;

R³ is a radical of the formula 2

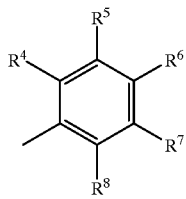

wherein R⁴ to R⁸ are independently of one another hydrogen, alkyl, alkenyl, alkynyl, cycloalkyl, cycloalkenyl, cycloalkylalkyl, cycloalkylalkenyl, cycloalkylalkynyl, aryl, arylalkyl, arylalkenyl, arylalkynyl, hydroxyl, alkoxy, alkenyloxy, alkynyloxy, cycloalkoxy, cycloalkylalkoxy, cycloalkylalkenyloxy, cycloalkylalkynyloxy, cycloalkenyloxy, aryloxy, arylalkoxy, arylalkenyloxy, arylalkynyloxy, thio, alkylthio, alkenylthio, alkynylthio, cycloalkylthio, cycloalkylalkylthio, cycloalkylalkenylthio, cycloalkylalkynylthio, cycloalkenylthio, arylthio, arylalkylthio, arylalkenylthio, arylalkynylthio, amino, unsubstituted or substituted mono- or dialkylamino, unsubstituted or substituted mono- or diarylamino, unsubstituted or substituted N-alkyl-N-arylamino, it being possible for alkyl and aryl to be identical or different, alkenylamino, alkynylamino, cycloalkylamino, cycloalkenylamino, sulfonyl, alkylsulfonyl, alkenylsulfonyl, alkynylsulfonyl, cycloalkylsulfonyl, cycloalkylalkylsulfonyl, cycloalkylalkenylsulfonyl, cycloalkylalkynylsulfonyl, arylsulfonyl, arylalkylsulfonyl, arylalkenylsulfonyl, arylalkynylsulfonyl, sulfoxyl, alkylsulfoxyl, alkenylsulfoxyl, alkynylsulfoxyl, cycloalkylsulfoxyl, cycloalkylalkylsulfoxyl, cycloalkylalkenylsulfoxyl, cycloalkylalkynylsulfoxyl, arylsulfoxyl, arylalkylsulfoxyl, arylalkenylsulfoxyl, arylalkynylsulfoxyl, aminosulfonyl, unsubstituted or substituted mono- or dialkylaminosulfonyl, unsubstituted or substituted diarylaminosulfonyl, unsubstituted or substituted N-alkyl-N-arylaminosulfonyl, it being possible for alkyl and aryl to be identical or different, alkylcarbonyl, alkenylcarbonyl, alkynylcarbonyl, cycloalkylcarbonyl, cycloalkylalkylcarbonyl, cycloalkylalkenylcarbonyl, cycloalkylalkynylcarbonyl, arylcarbonyl, arylalkylcarbonyl, arylalkenylcarbonyl, arylalkynylcarbonyl, carboxyl, alkoxycarbonyl, alkenyloxycarbonyl, alkynyloxycarbonyl, cycloalkoxycarbonyl, cycloalkylalkoxycarbonyl, cycloalkylalkenyloxycarbonyl, cycloalkylalkynyloxycarbonyl, aryloxycarbonyl, arylalkoxycarbonyl, arylalkenyloxycarbonyl, arylalkynyloxycarbonyl, aminocarbonyl, unsubstituted or substituted mono- or dialkylaminocarbonyl, unsubstituted or substituted mono- or diarylaminocarbonyl, unsubstituted or substituted N-alkyl-N-arylaminocarbonyl, it being possible for alkyl and aryl to be identical or different, unsubstituted or substituted mono- or dialkylcarbonylamino, unsubstituted or substituted mono- or diarylcarbonylamino, unsubstituted or substituted N-alkyl-N-arylcarbonylamino, it being possible for alkyl and aryl to be identical or different; alkoxyaminocarbonyl, alkenyloxyaminocarbonyl, alkynyloxycarbonylamino, cycloalkoxycarbonylamino, cycloalkylalkoxycarbonylamino, cycloalkylalkenyloxycarbonylamino, cycloalkylalkynyloxycarbonylamino, aryloxycarbonylamino, arylalkoxycarbonylamino, arylalkenyloxycarbonylamino, arylalkynyloxycarbonylamino, halogen, haloalkyl, haloalkenyl, haloalkynyl, haloalkoxy, haloalkenyloxy, haloalkynyloxy, haloalkylthio, haloalkenylthio, haloalkynylthio, haloalkylamino, haloalkenylamino, haloalkynylamino, haloalkylsulfonyl, haloalkenylsulfonyl, haloalkynylsulfonyl, haloalkylsulfoxyl, haloalkenylsulfoxyl, haloalkynylsulfoxyl, haloalkylcarbonyl, haloalkenylcarbonyl, haloalkynylcarbonyl, haloalkoxycarbonyl, haloalkenyloxycarbonyl, haloalkynyloxycarbonyl, haloalkylaminocarbonyl, haloalkenylaminocarbonyl, haloalkynylaminocarbonyl, haloalkoxycarbonylamino, haloalkenyloxycarbonylamino, haloalkynyloxycarbonylamino; cyano or nitro or one of the following groups:

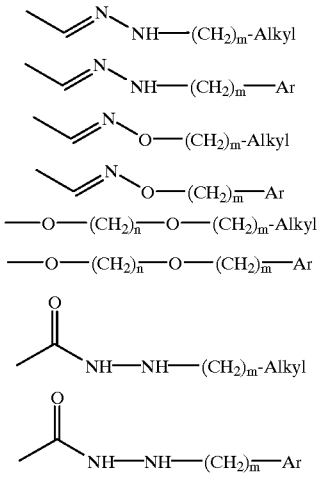

$n = 1, 2, 3; m = 0, 1, 2, 3$ or

R⁴, R⁵ together form a five- or six-membered, saturated or unsaturated, aromatic or non-aromatic, unsubstituted or substituted alkylene, alkenylene or alkdienylene chain; or R⁵, R⁶ together form a five- or six-membered, saturated or unsaturated, aromatic or non-aromatic, unsubstituted or substituted alkylene, alkenylene or alkdienylene chain; wherein at least one of R⁴ to R⁸ is other than hydrogen, and with the exception of 4-(4'-chlorobenzoyl)-3-methylisothiazole, 4-(4'-hydroxymethylcarbonylaminobenzoyl)-isothiazole and 4-(3',5'-tertiary-butyl-4'-hydroxybenzoyl)-isothiazole; or a salt of the 4-benzoylisothiazole of the formula 1 which is conventionally used in agriculture.

17. The 4-benzoylisothiazole of the formula 1 defined in claim 16, wherein R⁴ to R⁸ are independently of one another hydrogen, alkyl, alkenyl, alkynyl, cycloalkyl, cycloalkenyl, cycloalkylalkyl, cycloalkylalkenyl, cycloalkylalkynyl, aryl, arylalkyl, arylalkenyl, arylalkynyl, alkoxy, alkenyloxy, alkynyloxy, cycloalkoxy, cycloalkylalkoxy, cycloalkylalkenyloxy, cycloalkylalkynyloxy, cycloalkenyloxy, aryloxy, arylalkoxy, arylalkenyloxy, arylalkynyloxy, thio, alkylthio, alkenylthio, alkynylthio, cycloalkylthio, cycloalkylalkylthio, cycloalkylalkenylthio, cycloalkylalkynylthio, cycloalkenylthio, arylthio, arylalkylthio, arylalkenylthio, arylalkynylthio, amino, unsubstituted or substituted mono- or dialkylamino, unsubstituted or substituted mono- or diarylamino, unsubstituted or substituted N-alkyl-N-arylamino, it being possible for alkyl and aryl to be identical or different, alkenylamino, alkynylamino, cycloalkylamino, cycloalkenylamino, sulfonyl, alkylsulfonyl, alkenylsulfonyl, alkynylsulfonyl, cycloalkylsulfonyl, cycloalkylalkylsulfonyl, cycloalkylalkenylsulfonyl, cycloalkylalkynylsulfonyl, arylsulfonyl, arylalkylsulfonyl, arylalkenylsulfonyl, arylalkynylsulfonyl, sulfoxyl, alkylsulfoxyl, alkenylsulfoxyl, alkynylsulfoxyl, cycloalkylsulfoxyl, cycloalkylalkylsulfoxyl, cycloalkylalkenylsulfoxyl, cycloalkylalkynylsulfoxyl, arylsulfoxyl, arylalkylsulfoxyl, arylalkenylsulfoxyl, arylalkynylsulfoxyl, aminosulfonyl, unsubstituted or substituted mono- or dialkylaminosulfonyl, unsubstituted or substituted diarylaminosulfonyl, unsubstituted or substituted N-alkyl-N-arylaminosulfonyl, it being possible for alkyl and aryl to be identical or different, alkylcarbonyl, alkenylcarbonyl, alkynylcarbonyl, cycloalkylcarbonyl, cycloalkylalkylcarbonyl, cycloalkylalkenylcarbonyl, cycloalkylalkynylcarbonyl, arylcarbonyl, arylalkylcarbonyl, arylalkenylcarbonyl, arylalkynylcarbonyl, carboxyl, alkoxycarbonyl, alkenyloxycarbonyl, alkynyloxycarbonyl, cycloalkoxycarbonyl, cycloalkylalkoxycarbonyl, cycloalkylalkenyloxycarbonyl, cycloalkylalkynyloxycarbonyl, aryloxycarbonyl, arylalkoxycarbonyl, arylalkenyloxycarbonyl, arylalkynyloxycarbonyl, aminocarbonyl, unsubstituted or substituted mono- or dialkylaminocarbonyl, unsubstituted or substituted mono- or diarylaminocarbonyl, unsubstituted or substituted N-alkyl-N-arylaminocarbonyl, it being possible for alkyl and aryl to be identical or different, unsubstituted or substituted mono- or dialkylcarbonylamino, unsubstituted or substituted mono- or diarylcarbonylamino, unsubstituted or substituted N-alkyl-N-arylcarbonylamino, it being possible for alkyl and aryl to be identical or different; alkoxyaminocarbonyl, alkenyloxyaminocarbonyl, alkynyloxycarbonylamino, cycloalkoxycarbonylamino, cycloalkylalkoxycarbonylamino, cycloalkylalkenyloxycarbonylamino, cycloalkylalkynyloxycarbonylamino, aryloxycarbonylamino, arylalkoxycarbonylamino, arylalkenyloxycarbonylamino, arylalkynyloxycarbonylamino, halogen, haloalkyl, haloalkenyl, haloalkynyl, haloalkoxy, haloalkenyloxy, haloalkynyloxy, haloalkylthio, haloalkenylthio, haloalkynylthio, haloalkylamino, haloalkenylamino, haloalkynylamino, haloalkylsulfonyl, haloalkenylsulfonyl, haloalkynylsulfonyl, haloalkylsulfoxyl, haloalkenylsulfoxyl, haloalkynylsulfoxyl, haloalkylcarbonyl, haloalkenylcarbonyl, haloalkynylcarbonyl, haloalkoxycarbonyl, haloalkenyloxycarbonyl, haloalkynyloxycarbonyl, haloalkylaminocarbonyl, haloalkenylaminocarbonyl, haloalkynylaminocarbonyl, haloalkoxycarbonylamino, haloalkenyloxycarbonylamino, haloalkynyloxycarbonylamino; cyano or nitro or one of the following groups:

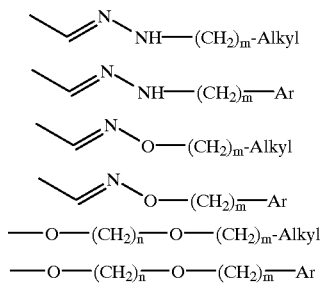

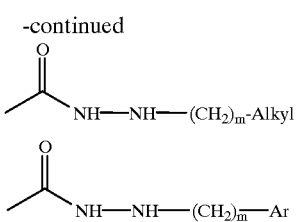

$n = 1,2,3;$
$m = 0,1,2,3$ or

R$^4$, R$^5$ together form a five- or six-membered, saturated or unsaturated, aromatic or non-aromatic, unsubstituted or substituted alkylene, alkenylene or alkdienylene chain; or R$^5$, R$^6$ together form a five- or six-membered, saturated or unsaturated, aromatic or non-aromatic, unsubstituted or substituted alkylene, alkenylene or alkdienylene chain;

and wherein at least one of R$^4$ to R$^8$ is other than hydrogen.

18. The 4-benzoylisothiazole of the formula 1 defined in claim 16, wherein one, two or three of R$^4$ to R$^8$ are other than hydrogen.

19. The 4-benzoylisothiazole of the formula 1 defined in claim 17, wherein one, two or three of R$^4$ to RB are other than hydrogen.

20. A herbicidal composition comprising a 4-benzoylisothiazole of the formula 1 defined in claim 1 and inert additives.

21. A method of controlling undesirable vegetation which comprises treating the undesired plants and/or their habitat with a herbicidally active amount of a 4-benzoylisothiazole of the formula 1 defined in claim 1.

22. A process for the preparation of the 4-benzoylisothiazole of the formula 1 defined in claim 1 which comprises reacting a haloisothiazole compound of the formula 3

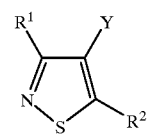

3 where Y is halogen with elemental magnesium, an organomagnesium or an organolithium compound and with a carboxylic acid of the formula 4

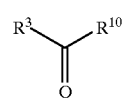

4 where R$^{10}$ is halogen, N-alkoxy-N-alkylamino or cyano in a temperature range of from −78° C. to 111° C. in the presence of an inert solvent.

23. A process for the preparation of the 4-benzoylisothiazole of the formula 1 defined in claim 1 which comprises reacting a halobenzene of the formula 5

$$R^3\text{---}Y \quad\quad 5$$

where Y is halogen with elemental magnesium, an organomagnesium or an organolithium compound and with a isothiazolecarboxylic acid of the formula 6a or 6b

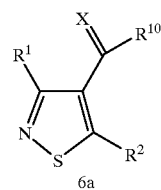
6a

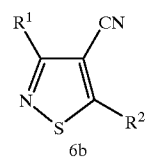
6b where $R^{10}$ is halogen or N-alkoxy-N-alkylamino in a temperature range of from −78° C. to 111° C. in the presence of an inert solvent.

* * * * *

UNITED STATES PATENT AND TRADEMARK OFFICE
CERTIFICATE OF CORRECTION

PATENT NO.: 6,083,879

DATED: July 4, 2000

INVENTOR(S): ENGEL et al.

It is certified that error appears in the above-identified patent and that said Letters Patent is hereby corrected as shown below:

In the abstract, line 2 after the formula, "x" should be --X--.

Col. 62, claim 19, line 30, "RB" should be --$R^8$--.

Signed and Sealed this

Twenty-fourth Day of April, 2001

*Attest:*

NICHOLAS P. GODICI

*Attesting Officer*     *Acting Director of the United States Patent and Trademark Office*